US012655193B2

(12) United States Patent　　　　(10) Patent No.: US 12,655,193 B2
Levin et al.　　　　　　　　　　　　　(45) Date of Patent: Jun. 16, 2026

(54) HLA CLASS II-RESTRICTED DRB T CELL RECEPTORS AGAINST RAS WITH G12D MUTATION

(71) Applicant: The United States of America, as represented by the Secretary, Department of Health and Human Services, Bethesda, MD (US)

(72) Inventors: Noam Levin, Rockville, MD (US); Rami Yoseph, Gaithersburg, MD (US); Gal Cafri, Kibbutz Nir David (IL); Steven A. Rosenberg, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 696 days.

(21) Appl. No.: 18/015,776

(22) PCT Filed: Jul. 13, 2021

(86) PCT No.: PCT/US2021/041375
§ 371 (c)(1),
(2) Date: Jan. 12, 2023

(87) PCT Pub. No.: WO2022/015694
PCT Pub. Date: Jan. 20, 2022

(65) Prior Publication Data
US 2023/0272038 A1　　Aug. 31, 2023

Related U.S. Application Data

(60) Provisional application No. 63/050,931, filed on Jul. 13, 2020.

(51) Int. Cl.
*C07K 14/725*　　　(2006.01)
*A61K 40/11*　　　　(2025.01)
　　　　　　(Continued)

(52) U.S. Cl.
CPC .......... *C07K 14/7051* (2013.01); *A61K 40/11* (2025.01); *A61K 40/32* (2025.01); *A61K 40/4253* (2025.01); *G01N 33/57575* (2026.01)

(58) Field of Classification Search
CPC .... C07K 14/7051; A61K 40/11; A61K 40/32; A61K 40/4253; A61K 38/00;
　　　　　　(Continued)

(56) References Cited

U.S. PATENT DOCUMENTS

| 8,034,334 B2 | 10/2011 | Dudley et al. |
| 8,383,099 B2 | 2/2013 | Dudley et al. |
| 2012/0244133 A1 | 9/2012 | Rosenberg et al. |

FOREIGN PATENT DOCUMENTS

| CA | 2397741 A1 * | 7/2001 | .......... C07K 14/005 |
| CN | 108395479 A | 8/2018 | |

(Continued)

OTHER PUBLICATIONS

Wojtczak, A. (2002) Glossary of Medical Education Terms Medical Teacher 24(4): 357; 1-25 (Year: 2002).*

(Continued)

*Primary Examiner* — Scarlett Y Goon
*Assistant Examiner* — Audrey L Buttice
(74) *Attorney, Agent, or Firm* — Leydig, Voit & Mayer

(57)　　　　ABSTRACT

Disclosed is an isolated or purified T cell receptor (TCR), wherein the TCR has antigenic specificity for a mutated human RAS amino acid sequence with a substitution of glycine at position 12 with aspartic acid. The TCRs may recognize G12D RAS presented by an HLA-DR heterodimer. Related polypeptides and proteins, as well as related (Continued)

Figure 1A:
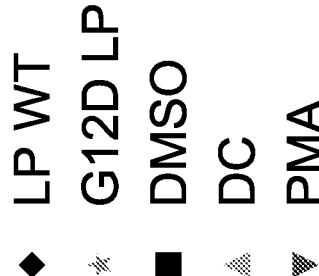
Figure 1A:
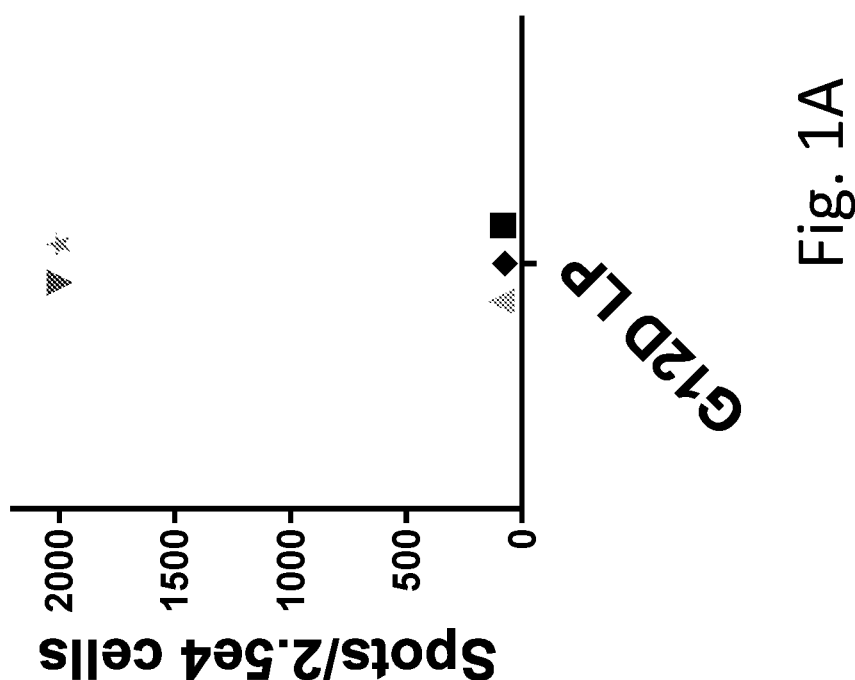

IFN-γ ELISPOT nucleic acids, recombinant expression vectors, host cells, populations of cells, and pharmaceutical compositions are also provided. Also disclosed are methods of detecting the presence of cancer in a mammal and methods of treating or preventing cancer in a mammal.

38 Claims, 9 Drawing Sheets

Specification includes a Sequence Listing.

(51) Int. Cl.
    *A61K 40/32*    (2025.01)
    *A61K 40/42*    (2025.01)
    *C07K 14/705*   (2006.01)
    *G01N 33/575*   (2026.01)

(58) Field of Classification Search
    CPC .. A61K 35/17; G01N 33/5748; G01N 33/574; A61P 35/00; C12N 5/0636; C12N 2510/00
    See application file for complete search history.

(56)                References Cited

FOREIGN PATENT DOCUMENTS

| | | |
|---|---|---|
| WO | WO 2018/026691 A1 | 2/2018 |
| WO | WO 2019/060349 A1 | 3/2019 |

OTHER PUBLICATIONS

Lewandowska, A.M., et al (2017) Environmental risk factors for cancer—review paper Ann. Agric. Environ. Med. 26(1); 1-7 (Year: 2017).*

Cuzick, J. (2017) Preventive therapy for cancer Lancet Oncol 18; e472-e482 (Year: 2017).*

DeCensi, A., et al (2015) Barriers to preventative therapy for breast and other major cancers and strategies to improve uptake ecancer 9(595); 1-12 (Year: 2015).*

Wong, W.K., et al (2019) Comparative analysis of the CDR loops of antigen receptors Frontiers in immunology 10(2454); 1-11 (Year: 2019).*

Jokinen, E., et al (2021) Predicting recognition between T cell receptors and epitopes within TCRGP PLOS Computational Biology 17(3); e1008814; 1-27 (Year: 2021).*

Sim et al., "High-affinity oligoclonal TCRs define effective adoptive T cell therapy targeting mutant KRAS-G12D", PNAS, 117(23): 12826-12835 (2020).

Murphy et al., eds., *Janeway's Immunobiology*, 7th Ed., New York: Garland Science (2008), pp. 157-158 (Section 4-10).

Cafri et al. "Memory T cells targeting oncogenic mutations detected in peripheral blood of epithelial cancer patients." *Nature Communications,* 10: 449, pp. 1-9.

Cafri et al., "mRNA vaccine-induced neoantigen-specific T cell immunity in patients with gastrointestinal cancer", *The Journal of Clinical Investigation,* 130(11): 5976-5988 (2020).

Cohen et al., "Enhanced Antitumor Activity of Murine-Human Hybrid T-Cell Receptor (TCR) in Human Lymphocytes Is Associated With Improving Pairing and TCR/CD3 Stability", *Cancer Research,* 66(17): 8878-8886 (2006).

Cohen et al., "Enhanced antitumor activity of T cells engineered to express T-cell receptors with a second disulfide bond", *Cancer Research,* 67(8): 3898-3903 (2007).

Cox et al. "Drugging the undruggable RAS: Mission possible?" *Nature Reviews. Drug* Discovery 13(11): 828-851 (2014).

Dudley et al., "Generation of Tumor-Infiltrating Lymphocyte Cultures for Use in Adoptive Transfer Therapy for Melanoma Patients", *Journal of Immunotherapy,* 26(4):332-342 (2003).

Haga-Friedman et al., "Incorporation of transmembrane hydrophobic mutations in the TCR enhance its surface expression and T cell functional avidity", *Journal of Immunology,* 188(11): 5538-5546 (2012).

Iiizumi et al., "Identification of Novel HLA Class II-Restricted Neoantigens Derived from Driver Mutations", *Cancers,* 11(226): 1-14 (2019).

International Searching Authority, International Search Report and Written Opinion issued in PCT/US2021/041375, mailed on Oct. 25, 2021.

Levin et al., "Identification and Validation of T-cell Receptors Targeting RAS Hotspot Mutations in Human Cancers for Use in Cell-based Immunotherapy", *Clinical Cancer Research,* 27(18): 5084-5095 (2021).

Riddell et al., "The use of anti-CD3 and anti-CD28 monoclonal antibodies to clone and expand human antigen-specific T cells", *Journal of Immunological Methods,* 128(2): 189-201 (1990).

Szymczak et al., "Correction of multi-gene deficiency in vivo using a single 'self-cleaving' 2A peptide-based retroviral vector", *Nature Biotechnology,* 22(5): 589-594 (2004).

Tran et al. "Cancer Immunotherapy Based on Mutation-Specific CD4+ T Cells in a Patient with Epithelial Cancer", *Science* 344(6184): 641-645 (2014).

Tran et al. "T-Cell Transfer Therapy Targeting Mutant KRAS in Cancer", *New England Journal of Medicine,* 375(23): 2255-2262 (2016).

Wang et. al. "Identification of T-cell Receptors Targeting KRAS-Mutated Human Tumors", *Cancer Immunology Research,* 4(3):204-14 (2016).

"TRA T-cell receptor alpha locus [*Homo sapiens* (human)]," Gene ID: 6955, (updated Oct. 9, 2016), Entrez Gene (ncbi.nlm.nih.gov/gene), printed on Dec. 8, 2016.

"TRB T cell receptor beta locus [*Homo sapiens* (human)]," Gene ID: 6957, (updated Oct. 9, 2016), Entrez Gene (ncbi.nlm.nih.gov/gene), printed on Dec. 8, 2016.

* cited by examiner

HLA CLASS II-RESTRICTED DRB T CELL RECEPTORS AGAINST RAS WITH G12D MUTATION

CROSS-REFERENCE TO RELATED APPLICATIONS

This patent application is the U.S. national stage of International Patent Application No. PCT/US2021/041375, filed Jul. 13, 2021, which claims the benefit of U.S. Provisional Patent Application No. 63/050,931, filed Jul. 13, 2020, each of which is incorporated by reference in its entirety herein.

STATEMENT REGARDING FEDERALLY SPONSORED RESEARCH OR DEVELOPMENT

This invention was made with Government support under project number ZIABC010984 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 161,018 Byte ASCII (Text) file named "766529_SeqLis_ST25.txt," dated Nov. 18, 2025.

BACKGROUND OF THE INVENTION

Some cancers may have very limited treatment options, particularly when the cancer becomes metastatic and unresectable. Despite advances in treatments such as, for example, surgery, chemotherapy, and radiation therapy, the prognosis for many cancers, such as, for example, pancreatic, colorectal, lung, endometrial, ovarian, and prostate cancers, may be poor. Accordingly, there exists an unmet need for additional treatments for cancer.

BRIEF SUMMARY OF THE INVENTION

An embodiment of the invention provides an isolated or purified T-cell receptor (TCR) comprising the amino acid sequences of: (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, or (l) all of SEQ ID NOs: 31-36, wherein the TCR has antigenic specificity for a mutated human RAS amino acid sequence with a substitution of glycine at position 12 with aspartic acid, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and wherein position 12 is defined by reference to the wild-type human KRAS, wild-type human HRAS, or wild-type human NRAS protein, respectively.

Another embodiment of the invention provides an isolated or purified polypeptide comprising a functional portion of the inventive TCR, wherein the functional portion comprises the amino acid sequences of: (a) all of SEQ ID NOs: 1-3, (b)

all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, or (l) all of SEQ ID NOs: 31-36.

Still another embodiment of the invention provides an isolated or purified protein, comprising: (a) a first polypeptide chain comprising the amino acid sequences of SEQ ID NOs: 1-3 and a second polypeptide chain comprising the amino acid sequences of SEQ ID NOs: 4-6; (b) a first polypeptide chain comprising the amino acid sequences of SEQ ID NOs: 11-13 and a second polypeptide chain comprising the amino acid sequences of SEQ ID NOs: 14-16; (c) a first polypeptide chain comprising the amino acid sequences of SEQ ID NOs: 21-23 and a second polypeptide chain comprising the amino acid sequences of SEQ ID NOs: 24-26; or (d) a first polypeptide chain comprising the amino acid sequences of SEQ ID NOs: 31-33 and a second polypeptide chain comprising the amino acid sequences of SEQ ID NOs: 34-36.

Embodiments of the invention further provide nucleic acids, recombinant expression vectors, host cells, populations of cells, and pharmaceutical compositions relating to the inventive TCRs, polypeptides, and proteins.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 7 and 8; 8 and 7; 9 and 10; 10 and 9; 17 and 18; 18 and 17; 19 and 20; 20 and 19; 27 and 28; 28 and 27; 29 and 30; 30 and 29; 37 and 38; 38 and 37; 39 and 40; 40 and 39; 55 and 56; 56 and 55; 57 and 58; 58 and 57; 59 and 60; 60 and 59; 61 and 62; 62 and 61; 63 and 64; 64 and 63; 65 and 66; 66 and 65; 67 and 68; 68 and 67; 69 and 70; 70 and 69; 71 and 72; 72 and 71; 73 and 74; 74 and 73; 75 and 76; 76 and 75; 77 and 78; 78 and 77; 79 and 80; 80 and 79; 81 and 82; 82 and 81; 83 and 84; 84 and 83; 85 and 86; or 86 and 85.

Methods of detecting the presence of cancer in a mammal, methods of treating or preventing cancer in a mammal, methods of inducing an immune response against a cancer in a mammal, methods of producing a host cell expressing a TCR that has antigenic specificity for the peptide of MTEYKLVVVGADGVGKSALTIQLI (SEQ ID NO: 88), and methods of producing the inventive TCRs, polypeptides, and proteins, are further provided by embodiments of the invention.

BRIEF DESCRIPTION OF THE SEVERAL VIEWS OF THE DRAWING(S)

Figure 1B:
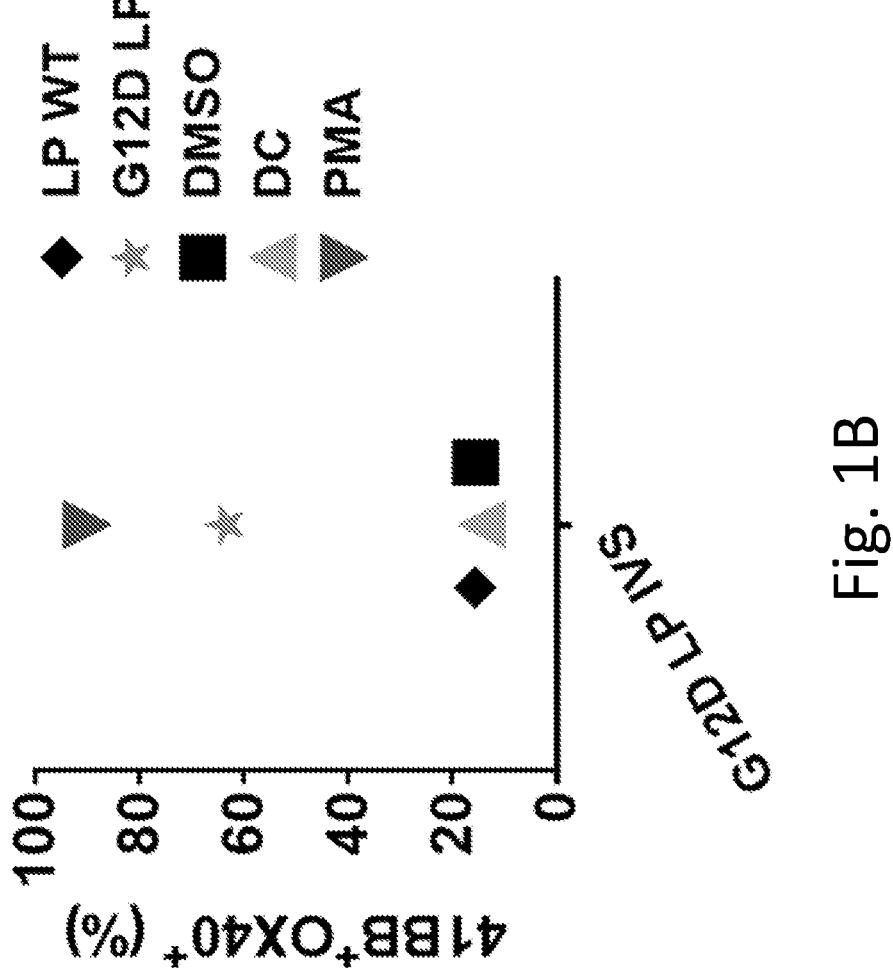

FIGS. 1A-1B show the reactivity results of PBL from colorectal cancer patient 4271 following in vitro stimulation (IVS) with DC pulsed with the G12D 24-mer peptide (G12D LP). These cells were tested by co-culturing with DC which had been pulsed with the G12D 24-mer peptide (star) or the corresponding WT 24-mer peptide (diamond). Co-culturing with DC treated with DMSO (square) and co-culturing with DC alone (▲) served as negative controls. PBL cultured in the presence of PMA (▼) served as a positive control. FIG. 1A is a graph showing the reactivity as measured by an IFN-γ ELISPOT assay (spots/2.5e4 cells). FIG. 1B is a graph showing the reactivity as measured by the percentage of 4-1BB$^+$ and/or OX40$^+$ cells detected in a flow cytometry assay (FACS).

Figure 1C:
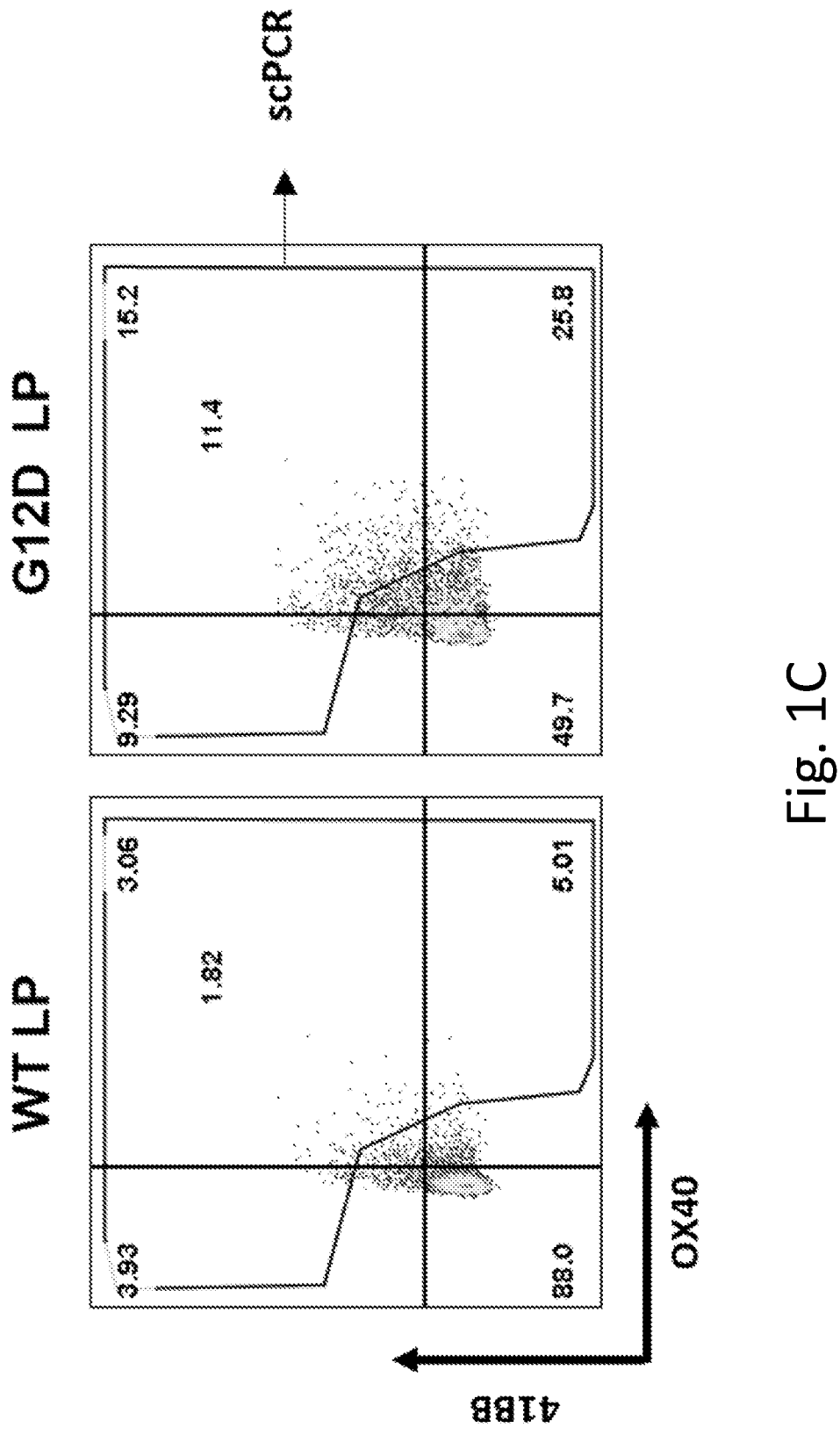
Figure 2A:
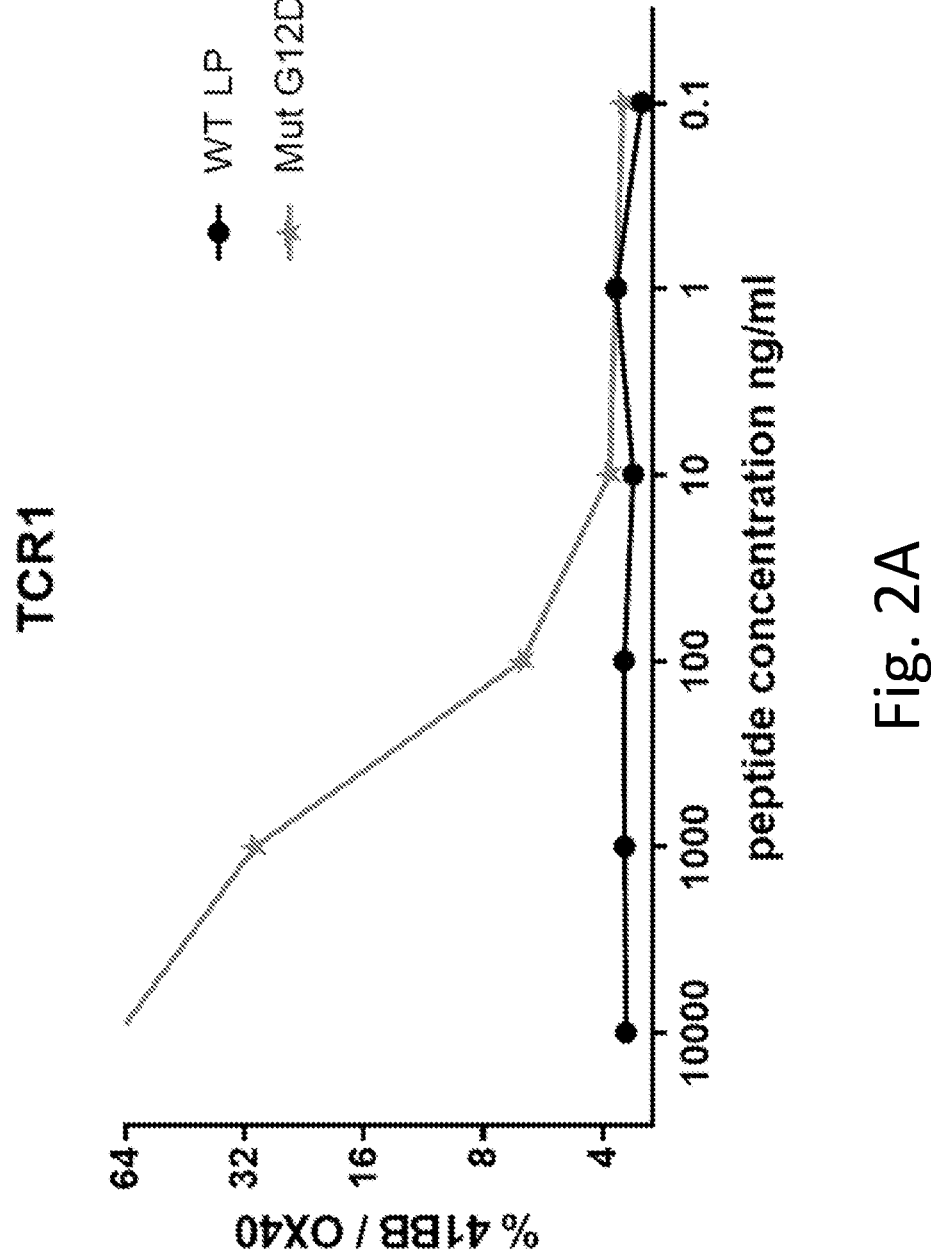
Figure 2B:
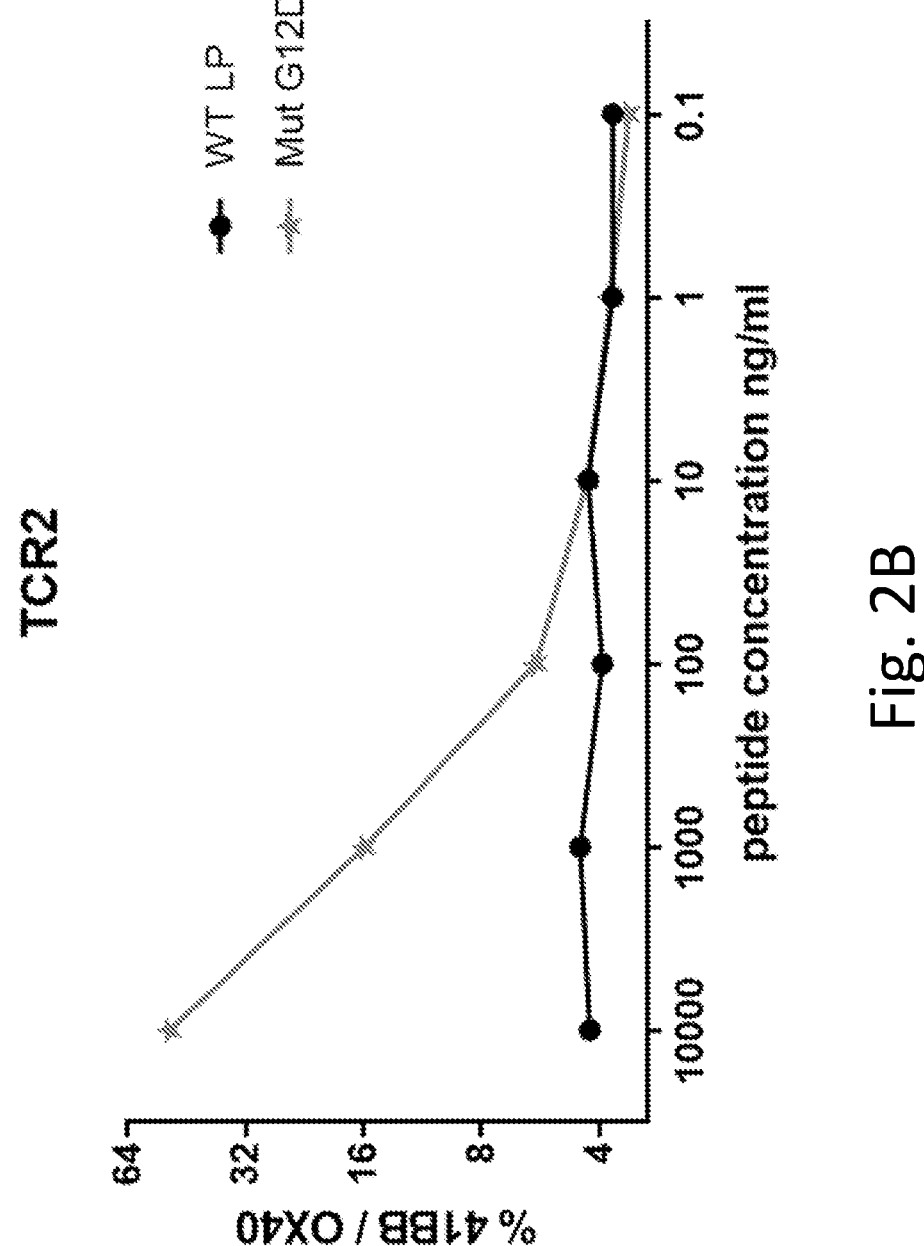
Figure 2C:
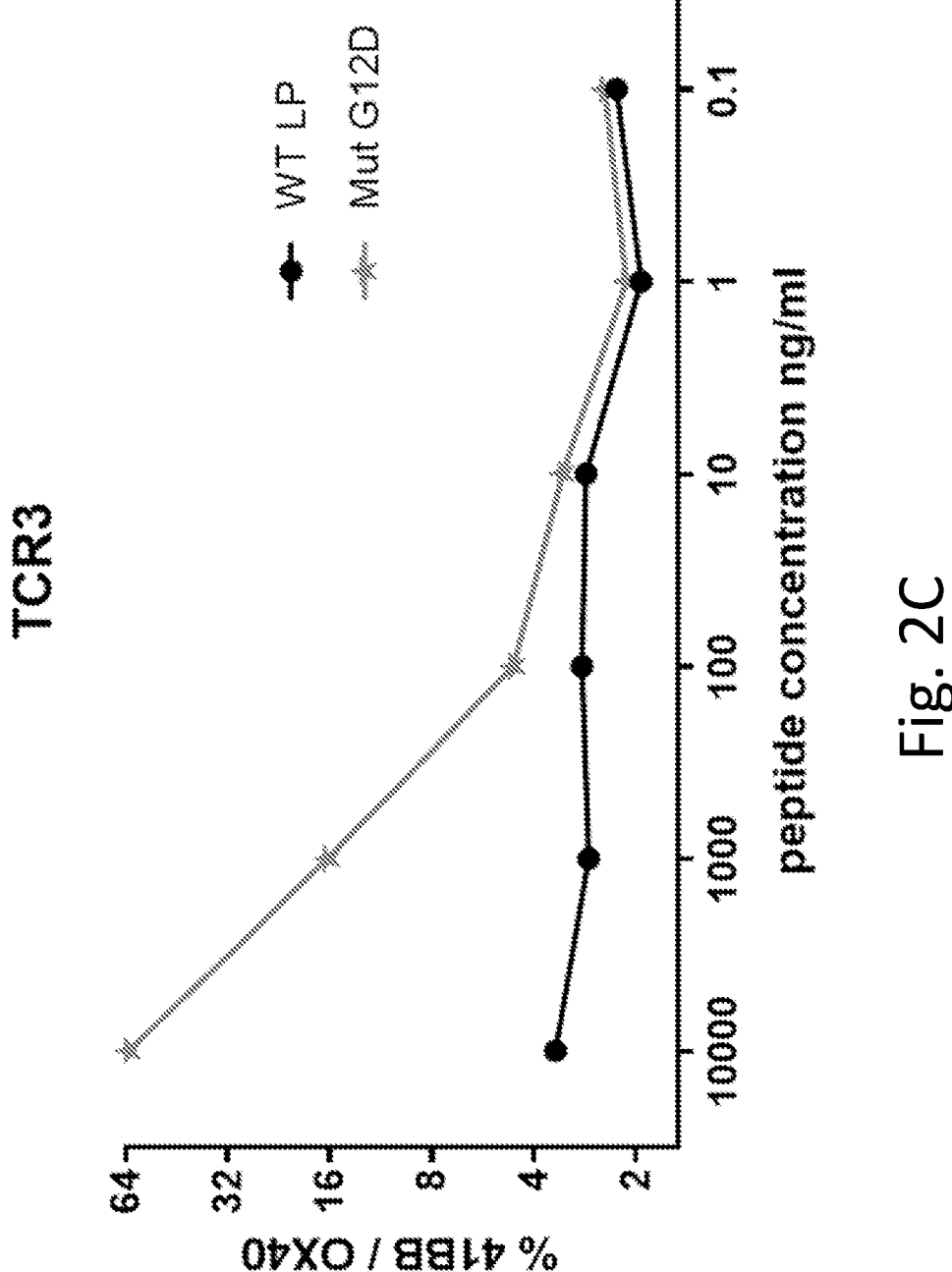
Figure 2D:
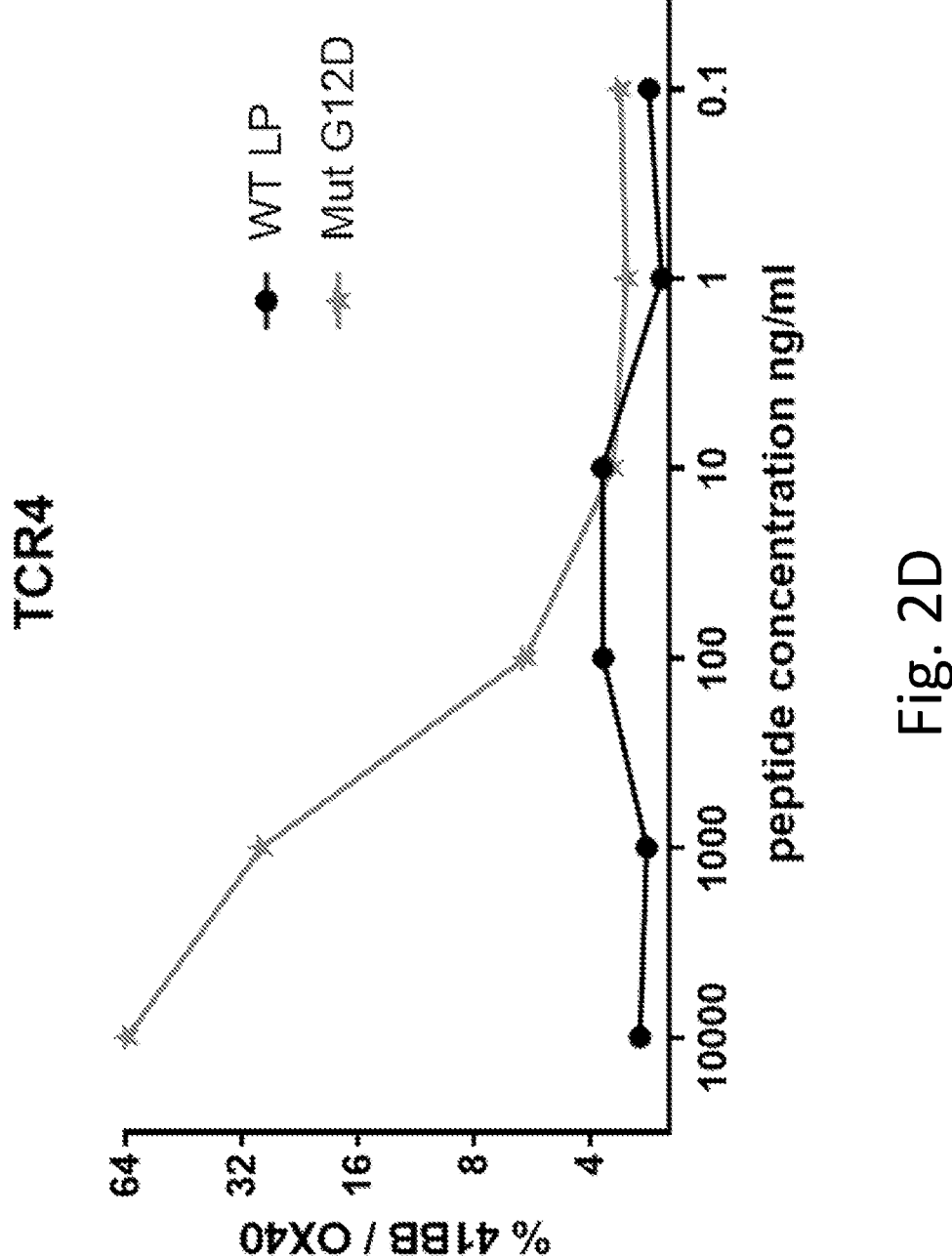

FIG. 1C shows the results of a FACS analysis for 4-1BB and/or OX40 expression following IVS of PBL from colorectal cancer patient 4271 with DC which had been pulsed with the G12D 24-mer peptide, tested by co-culturing with autologous DC pulsed with the G12D 24-mer peptide or the corresponding WT 24-mer peptide. The arrow indicates that those cells which upregulated 4-1BB and/or OX40 expression following IVS with G12D 24-mer peptide and restimulated with G12D 24-mer underwent single cell polymerase chain reaction (scPCR) to determine the TCR sequence.

FIGS. 2A-2D are graphs showing the percentages of 4-1BB⁺ and/or OX40⁺ cells measured following co-culture of effector cells with target cells. Effector cells were autologous PBL independently transduced with 4271 TCR1 (2A), 4271 TCR2 (2B), 4271 TCR3 (2C), or 4271 TCR4 (2D). Target cells were autologous DCs pulsed with the indicated concentrations (ng/ml) of G12D 24-mer peptide (stars) or the corresponding WT 24-mer peptide (circles).

Figure 3A:
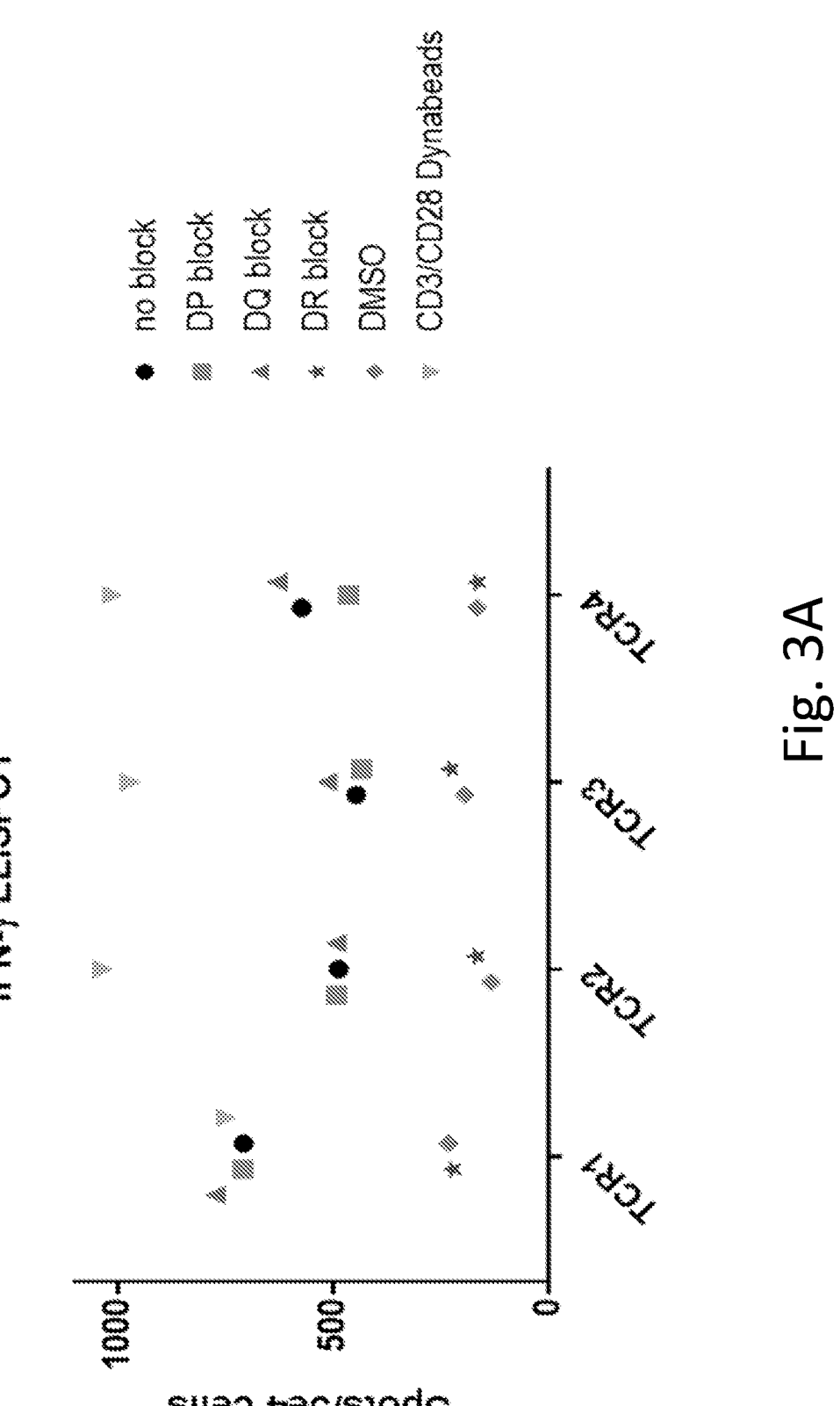

FIG. 3A is a graph showing reactivity as measured by IFN-γ ELISPOT assay (number of spots/3e4 cells) measured following co-culture of target cells with effector cells. The effector cells were T cells independently transduced with 4271 TCR1, 4271 TCR2, 4271 TCR3, or 4271 TCR4. Effector cells were co-cultured with autologous DC pulsed with the G12D 24-mer peptide after MHC blocking with anti-HLA DP (squares), anti-HLA DQ (▲), or anti-HLA DR (stars) blocking antibodies or with no antibodies (circles). Effector cells co-cultured with DMSO treated DC (diamonds) served as a negative control. Effector cells cultured in the presence of anti-CD3/anti-CD28 Dynabeads (▼) served as a positive control.

Figure 3B:
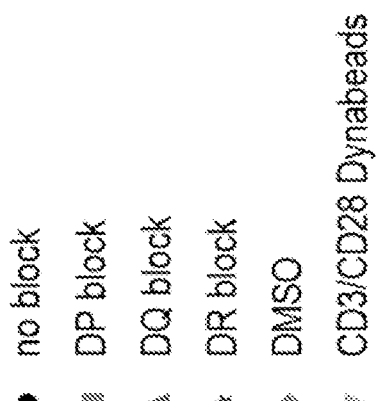
Figure 3B:
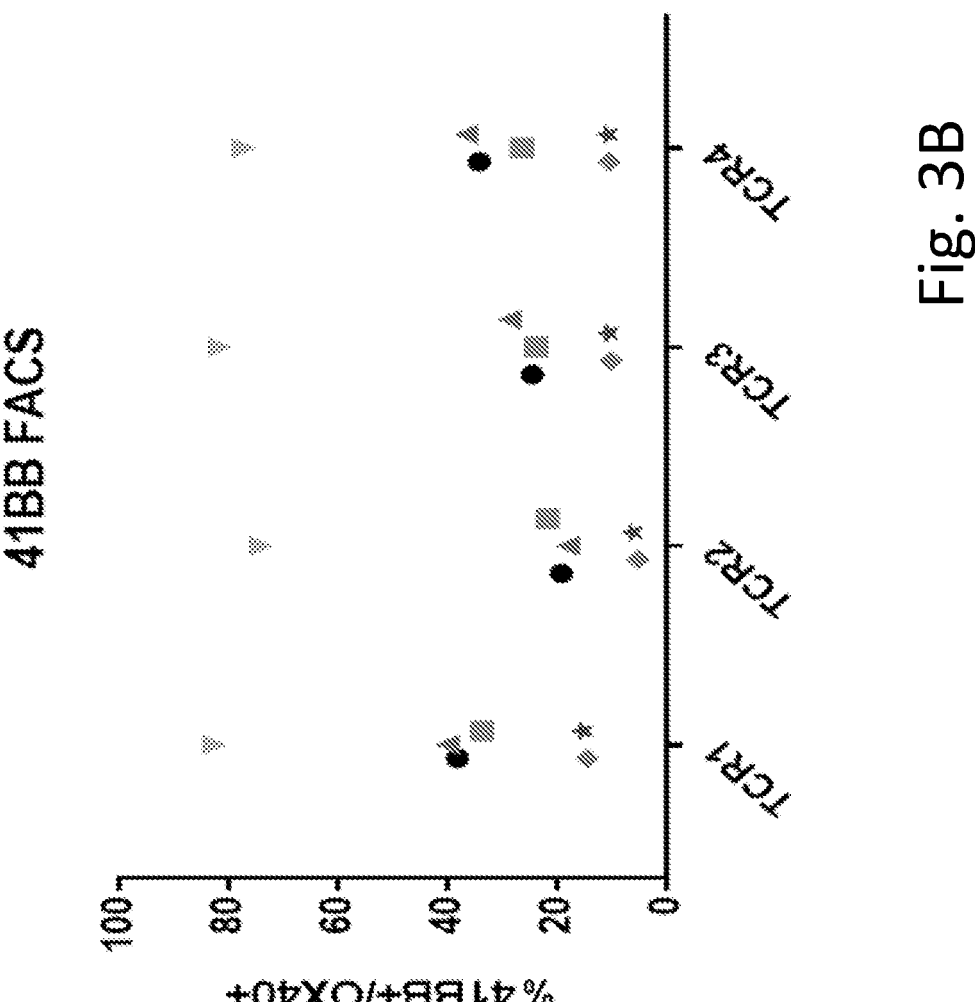

FIG. 3B is a graph showing the percentage of 4-1BB⁺ and/or OX40⁺ cells in the CD3⁺/CD4⁺ population measured following co-culture of target cells with effector cells. The effector cells were T cells independently transduced with 4271 TCR1, 4271 TCR2, 4271 TCR3, or 4271 TCR4. Effector cells were co-cultured with autologous DC pulsed with the G12D 24-mer peptide after MHC blocking with anti-HLA DP (squares), anti-HLA DQ (▲), or anti-HLA DR (stars) antibodies or with no blocking antibodies (circles). Effector cells co-cultured with DMSO treated DC (diamonds) served as a negative control. Effector cells cultured in the presence of anti-CD3/anti-CD28 Dynabeads (▼) served as a positive control.

DETAILED DESCRIPTION OF THE INVENTION

RAS family proteins belong to the large family of small GTPases. Without being bound to a particular theory or mechanism, it is believed that, when mutated, RAS proteins may be involved in signal transduction early in the oncogenesis of many human cancers. A single amino acid substitution may activate the protein. The mutated RAS protein product may be constitutively activated. Mutated RAS proteins may be expressed in any of a variety of human cancers such as, for example, pancreatic (e.g., pancreatic carcinoma), colorectal, lung (e.g., lung adenocarcinoma), endometrial, ovarian (e.g., epithelial ovarian cancer), and prostate cancers. The human RAS family proteins include KRAS, HRAS, and NRAS.

KRAS is also referred to as GTPase KRas, V-Ki-Ras2 Kirsten rat sarcoma viral oncogene, or KRAS2. There are two transcript variants of KRAS: KRAS variant A and KRAS variant B. Wild-type (WT) KRAS variant A has the amino acid sequence of SEQ ID NO: 41. WT KRAS variant B has the amino acid sequence of SEQ ID NO: 42. Hereinafter, references to "KRAS" (mutated or unmutated (WT)) refer to both variant A and variant B, unless specified otherwise. When activated, mutated KRAS binds to guanosine-5'-triphosphate (GTP) and converts GTP to guanosine 5'-diphosphate (GDP).

HRAS is another member of the RAS protein family. HRAS is also referred to as Harvey Rat Sarcoma Viral Oncoprotein, V-Ha-Ras Harvey Rat Sarcoma Viral Oncogene Homolog, or Ras Family Small GTP Binding Protein H-Ras. WT HRAS has the amino acid sequence of SEQ ID NO: 43.

NRAS is still another member of the RAS protein family. NRAS is also referred to as GTPase NRas, V-Ras Neuroblastoma RAS Viral Oncogene Homolog, or NRAS1. WT NRAS has the amino acid sequence of SEQ ID NO: 44.

An embodiment of the invention provides an isolated or purified TCR, wherein the TCR has antigenic specificity for a mutated human RAS amino acid sequence with a substitution of glycine at position 12 with aspartic acid, wherein the mutated human RAS amino acid sequence is a mutated human KRAS, a mutated human HRAS, or a mutated human NRAS amino acid sequence, and wherein position 12 is defined by reference to the WT human KRAS, WT human HRAS, or WT human NRAS protein, respectively. Hereinafter, references to a "TCR" also refer to functional portions and functional variants of the TCR, unless specified otherwise.

The mutated human RAS amino acid sequence may be a mutated human KRAS amino acid sequence, a mutated human HRAS amino acid sequence, or a mutated human NRAS amino acid sequence. The amino acid sequences of WT human KRAS, NRAS, and HRAS protein each have a length of 188 or 189 amino acid residues and have a high degree of identity to one another. For example, the amino acid sequence of the WT human NRAS protein is 86.8% identical to that of the WT human KRAS protein. Amino acid residues 1-86 of the WT human NRAS protein and the WT human KRAS protein are 100% identical. The amino acid sequence of the WT human HRAS protein is 86.3% identical to that of the WT human KRAS protein. Amino acid residues 1-94 of the WT human HRAS protein and the WT human KRAS protein are 100% identical. Hereinafter, references to "RAS" (mutated or unmutated (WT)) collectively refer to KRAS, HRAS, and NRAS, unless specified otherwise.

In an embodiment of the invention, the mutated human RAS amino acid sequence comprises a human RAS amino acid sequence with a substitution of glycine at position 12 with aspartic acid, wherein position 12 is defined by reference to the corresponding WT RAS protein. The WT RAS protein may be any one of WT KRAS protein (SEQ ID NO: 41 or 42), WT HRAS protein (SEQ ID NO: 43), or WT NRAS protein (SEQ ID NO: 44) because, as explained above, amino acid residues 1-86 of the WT human NRAS protein and the WT human KRAS protein are 100% identical, and amino acid residues 1-94 of the WT human HRAS protein and the WT human KRAS protein are 100% identical. Accordingly, the amino acid residue at position 12 of each of WT KRAS, WT HRAS, and WT NRAS protein is the same, namely, glycine.

The mutated human RAS amino acid sequence has a substitution of glycine at position 12 with aspartic acid. In this regard, embodiments of the invention provide TCRs with antigenic specificity for any human RAS protein, polypeptide or peptide amino acid sequence with a G12D mutation.

Mutations and substitutions of RAS are defined herein by reference to the amino acid sequence of the corresponding WT RAS protein. Thus, mutations and substitutions of RAS are described herein by reference to the amino acid residue present at a particular position in WT RAS protein (namely, position 12), followed by the position number, followed by the amino acid residue with which that residue has been replaced in the particular mutation or substitution under discussion. A RAS amino acid sequence (e.g., a RAS peptide) may comprise fewer than all of the amino acid residues of the full-length, WT RAS protein. Accordingly, position 12 is defined herein by reference to the WT full-length RAS protein (namely, any one of SEQ ID NOs: 41-44) with the understanding that the actual position of the corresponding residue in a particular example of a RAS amino acid sequence may be different. When the positions are as defined by any one of SEQ ID NOs: 41-44, the term "G12" refers to the glycine normally present at position 12 of any one of SEQ ID NOs: 41-44, and "G12D" indicates that the glycine normally present at position 12 of any one of SEQ ID NOs: 41-44 is replaced by aspartic acid. For example, when a particular example of a RAS amino acid sequence is, e.g., TEYKLVVVGA̲GGVGKSALTIQLI (SEQ ID NO: 90) (an exemplary WT KRAS peptide corresponding to contiguous amino acid residues 2 to 24 of SEQ ID NO: 41), "G12D" refers to a substitution of the underlined glycine in SEQ ID NO: 90 with aspartic acid, even though the actual position of the underlined glycine in SEQ ID NO: 90 is 11. Human RAS amino acid sequences with the G12D mutation are hereinafter referred to as "G12D RAS".

Examples of full-length RAS proteins with the G12D mutation are set forth in Table 1 below.

TABLE 1

| Mutated Full-Length RAS Protein | SEQ ID NO: |
| --- | --- |
| G12D KRAS variant A | 45 |
| G12D KRAS variant B | 46 |
| G12D HRAS | 47 |
| G12D NRAS | 48 |

In an embodiment of the invention, the TCR has antigenic specificity for a RAS peptide with the G12D mutation described above, wherein the G12D RAS peptide has any length. In an embodiment of the invention, the G12D RAS peptide has any length suitable for binding to any of the HLA Class II molecules described herein. For example, the TCR may have antigenic specificity for a RAS peptide with the G12D mutation, the RAS peptide having a length of about 11 to about 30 amino acid residues, about 12 to about 24 amino acid residues, or about 18 to about 20 amino acid residues. The G12D RAS peptide may comprise any contiguous amino acid residues of mutated RAS protein which include the G12D mutation. In an embodiment of the invention, the TCR may have antigenic specificity for a RAS peptide with the G12D mutation, the mutated RAS peptide having a length of about 30 amino acid residues, about 29 amino acid residues, about 28 amino acid residues, about 27 amino acid residues, about 26 amino acid residues, about 25 amino acid residues, about 24 amino acid residues, about 23 amino acid residues, about 22 amino acid residues, about 21 amino acid residues, about 20 amino acid residues, about 19 amino acid residues, about 18 amino acid residues, about 17 amino acid residues, about 16 amino acid residues, about 15 amino acid residues, about 14 amino acid residues, about 13 amino acid residues, about 12 amino acid residues, about 11 amino acid residues, or a range of any two of the foregoing values. An example of a specific peptide with the G12D mutation, which may be recognized by the inventive TCRs, is MTEYKLVVVGADGVGKSALTIQLI (SEQ ID NO: 88). In an embodiment of the invention, the TCR has antigenic specificity for the mutated human RAS amino acid sequence of SEQ ID NO: 88. In an embodiment of the invention, the TCR does not have antigenic specificity for the wild-type human RAS amino acid sequence of MTEYKLVVVGAGGVGKSALTIQLI (SEQ ID NO: 89).

In an embodiment of the invention, the inventive TCRs are able to recognize G12D RAS presented by an HLA Class II molecule. In this regard, the TCR may elicit an immune response upon binding to G12D RAS within the context of an HLA Class II molecule. The inventive TCRs are able to recognize G12D RAS that is presented by an HLA Class II molecule and may bind to the HLA Class II molecule in addition to G12D RAS.

In an embodiment of the invention, the HLA Class II molecule is an HLA-DR heterodimer. The HLA-DR heterodimer is a cell surface receptor including an α chain and a β chain. The HLA-DR α chain is encoded by the HLA-DRA gene. The HLA-DR β chain is encoded by the HLA-DRB1 gene, the HLA-DRB3 gene, HLA-DRB4 gene, or the HLA-DRB5 gene. Examples of molecules encoded by the HLA-DRB1 gene may include, but are not limited to, HLA-DR1, HLA-DR2, HLA-DR3, HLA-DR4, HLA-DR5, HLA-DR6, HLA-DR7, HLA-DR8, HLA-DR9, HLA-DR10, HLA-DR11, HLA-DR12, HLA-DR13, HLA-DR14, HLA-DR15, HLA-DR16, and HLA-DR17. The HLA-DRB3 gene encodes HLA-DR52. The HLA-DRB4 gene encodes HLA-DR53. The HLA-DRB5 gene encodes HLA-DR51. In an embodiment of the invention, the HLA Class II molecule comprises a HLA-DR α chain in combination with a HLA-DR β chain encoded by any one of the HLA-DRB1 gene, the HLA-DRB3 gene, or the HLA-DRB4 gene. In an especially preferred embodiment, the HLA Class II molecule is an HLA-DRB1*03:HLA-DRA*01 heterodimer, an HLA-DRB1*11:HLA-DRA*01 heterodimer, an HLA-DRB3*01:HLA-DRA*01 heterodimer, an HLA-DRB3*03:HLA-DRA*01 heterodimer, an HLA-DRB4*03:HLA-DRA*01 heterodimer, or an HLA-DRB4*01:HLA-DRA*01 heterodimer (namely, expressed by the HLA-DRB1*03:HLA-DRA*01, HLA-DRB1*11:HLA-DRA*01, HLA-DRB3*01:HLA-DRA*01, HLA-DRB3*03:HLA-DRA*01, HLA-DRB4*03:HLA-DRA*01, or HLA-DRB4*01:HLA-DRA*01 alleles). In an embodiment, the HLA-DR β chain is encoded by the HLA-DRB1*03:01, HLA-DRB1*11:01, HLA-DRB3*01:01:02, HLA-DRB3*03:01:01, HLA-DRB4*01:01, or HLA-DRB4*03:01 alleles.

The TCRs of the invention may provide any one or more of a variety of advantages, including when expressed by cells used for adoptive cell transfer. G12D RAS is expressed by cancer cells and is not expressed by normal, noncancerous cells. Without being bound to a particular theory or mechanism, it is believed that the inventive TCRs advantageously target the destruction of cancer cells while minimizing or eliminating the destruction of normal, non-cancerous cells, thereby reducing, for example, by minimizing or eliminating, toxicity. Moreover, because the G12D mutation is likely to occur in the early stages of tumorigenesis, the G12D RAS mutation may be expressed on substantially all of a patient's cancer cells. The inventive TCRs may, advantageously, successfully treat or prevent G12D RAS-positive cancers that do not respond to other types of treatment such as, for example, chemotherapy, surgery, or radiation. Additionally, the inventive TCRs may provide highly avid recognition of G12D RAS, which may provide the ability to recognize unmanipulated tumor cells (e.g., tumor cells that have not been treated with interferon (IFN)-γ, transfected with a vector encoding one or both of G12D RAS and and any of the HLA-DR heterodimers described herein, pulsed with a G12D RAS peptide, or a combination thereof). KRAS mutations are found in about 70% of pancreatic cancer, 36% of colorectal cancer and 20% of lung cancer. Most commonly, mutations occur in the codon 12 (encoding glycine, G). The G12D RAS mutation is found in about 40% and about 12% of patients with pancreatic and colorectal cancers, respectively. Moreover, the HLA-DRB1*03, HLA-DRB1*11, HLA-DRB3*01, HLA-DRB3*03, HLA-DRB4*01, and HLA-DRB4*03 alleles are common. These alleles are expressed by more than 10% of humans with Caucasian ethnicity in the United States and are also commonly expressed by humans of other ethnicities. Accordingly, the inventive TCRs may increase the number of immunotherapy-eligible cancer patients to include those patients that express the HLA-DRB1*03, HLA-DRB1*11, HLA-DRB3*01, HLA-DRB3*03, HLA-DRB4*01, or HLA-DRB4*03 allele who may not be eligible for immunotherapy using TCRs that recognize RAS presented by other MHC molecules. Moreover, the inventive TCRs, polypeptides and proteins comprise human CDR and variable region amino acid sequences, which may reduce the risk of rejection by the human immune system as compared to, e.g., TCRs, polypeptides and proteins comprising mouse CDR and variable region amino acid sequences.

The phrase "antigenic specificity," as used herein, means that the TCR can specifically bind to and immunologically recognize G12D RAS with high avidity. For example, a TCR may be considered to have "antigenic specificity" for G12D RAS if about $1\times10^4$ to about $1\times10^5$ T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, 20,000 pg/mL or more, or a range defined by any two of the foregoing values) of IFN-γ upon co-culture with (a) antigen-negative, HLA Class II molecule positive target cells pulsed with a low concentration of G12D RAS peptide (e.g., about 0.05 ng/mL to about 10 ng/mL, 1 ng/mL, 2 ng/mL, 5 ng/mL, 8 ng/mL, 10 ng/mL, or a range defined by any two of the foregoing values) or (b) antigen-negative, HLA Class II molecule positive target cells into which a nucleotide sequence encoding G12D RAS has been introduced such that the target cell expresses G12D RAS. Cells expressing the inventive TCRs may also secrete IFN-γ upon co-culture with antigen-negative, HLA Class II molecule positive target cells pulsed with higher concentrations of G12D RAS peptide. The HLA Class II molecule may be any of the HLA Class II molecules described herein.

Alternatively or additionally, a TCR may be considered to have "antigenic specificity" for G12D RAS if T cells expressing the TCR secrete at least twice (e.g., five times) as much IFN-γ upon co-culture with (a) antigen-negative, HLA Class II molecule positive target cells pulsed with a low concentration of G12D RAS peptide or (b) antigen-negative, HLA Class II molecule positive target cells into which a nucleotide sequence encoding G12D RAS has been introduced such that the target cell expresses G12D RAS as compared to the amount of IFN-γ expressed by a negative control. The negative control may be, for example, (i) T cells expressing the TCR, co-cultured with (a) antigen-negative, HLA Class II molecule positive target cells pulsed with the same concentration of an irrelevant peptide (e.g., some other peptide with a different sequence from the G12D RAS peptide) or (b) antigen-negative, HLA Class II molecule positive target cells into which a nucleotide sequence encoding an irrelevant peptide has been introduced such that the target cell expresses the irrelevant peptide, or (ii) untransduced T cells (e.g., derived from PBMC, which do not express the TCR) co-cultured with (a) antigen-negative, HLA Class II molecule positive target cells pulsed with the same concentration of G12D RAS peptide or (b) antigen-negative, HLA Class II molecule positive target cells into which a nucleotide sequence encoding G12D RAS has been introduced such that the target cell expresses G12D RAS. The HLA Class II molecule expressed by the target cells of the negative control would be the same HLA Class II molecule expressed by the target cells that are co-cultured with the T cells being tested. The HLA Class II molecule may be any of the HLA Class II molecules described herein. IFN-γ secretion may be measured by methods known in the art such as, for example, enzyme-linked immunosorbent assay (ELISA).

Alternatively or additionally, a TCR may be considered to have "antigenic specificity" for G12D RAS if at least twice (e.g., five times) as many of the numbers of T cells expressing the TCR secrete IFN-γ upon co-culture with (a) antigen-negative, HLA Class II molecule positive target cells pulsed with a low concentration of G12D RAS peptide or (b) antigen-negative, HLA Class II molecule positive target cells into which a nucleotide sequence encoding G12D RAS has been introduced such that the target cell expresses G12D RAS as compared to the numbers of negative control T cells that secrete IFN-γ. The HLA Class II molecule, concentration of peptide, and the negative control may be as described herein with respect to other aspects of the invention. The numbers of cells secreting IFN-γ may be measured by methods known in the art such as, for example, ELISPOT.

Alternatively or additionally, a TCR may be considered to have "antigenic specificity" for G12D RAS if T cells expressing the TCR upregulate expression of one or more T-cell activation markers as measured by, for example, flow cytometry after stimulation with target cells expressing G12D RAS. Examples of T-cell activation markers include 4-1BB, OX40, CD107a, CD69, and cytokines that are upregulated upon antigen stimulation (e.g., tumor necrosis factor (TNF), interleukin (IL)-2, etc.).

An embodiment of the invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. The polypeptides of the inventive TCR can comprise any amino acid sequence, provided that the TCR has antigenic specificity for G12D RAS. In some embodiments, the TCR is non-naturally occurring.

In an embodiment of the invention, the TCR comprises two polypeptide chains, each of which comprises a variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 1 (CDR1 of α chain of 4271 TCR1), a CDR2 comprising the amino acid sequence of SEQ ID NO: 2 (CDR2 of α chain of 4271 TCR1), and a CDR3 comprising the amino acid sequence of SEQ ID NO: 3 (CDR3 of α chain of 4271 TCR1), and a second polypeptide chain comprising a CDR1 comprising the amino acid sequence of SEQ ID NO: 4 (CDR1 of β chain of 4271 TCR1), a CDR2 comprising the amino acid sequence of SEQ ID NO: 5 (CDR2 of β chain of 4271 TCR1), and a CDR3 comprising the amino acid sequence of SEQ ID NO: 6 (CDR3 of β chain of 4271 TCR1).

In another embodiment of the invention, the TCR comprises a first polypeptide chain comprising a CDR1 comprising the amino acid sequence of SEQ ID NO: 11 (CDR1 of α chain of 4271 TCR2), a CDR2 comprising the amino acid sequence of SEQ ID NO: 12 (CDR2 of α chain of 4271 TCR2), and a CDR3 comprising the amino acid sequence of SEQ ID NO: 13 (CDR3 of α chain of 4271 TCR2), and a second polypeptide chain comprising a CDR1 comprising the amino acid sequence of SEQ ID NO: 14 (CDR1 of β chain of 4271 TCR2), a CDR2 comprising the amino acid sequence of SEQ ID NO: 15 (CDR2 of β chain of 4271 TCR2), and a CDR3 comprising the amino acid sequence of SEQ ID NO: 16 (CDR3 of β chain of 4271 TCR2).

In another embodiment of the invention, the TCR comprises a first polypeptide chain comprising a CDR1 comprising the amino acid sequence of SEQ ID NO: 21 (CDR1 of α chain of 4271 TCR3), a CDR2 comprising the amino acid sequence of SEQ ID NO: 22 (CDR2 of α chain of 4271 TCR3), and a CDR3 comprising the amino acid sequence of SEQ ID NO: 23 (CDR3 of α chain of 4271 TCR3), and a second polypeptide chain comprising a CDR1 comprising the amino acid sequence of SEQ ID NO: 24 (CDR1 of β chain of 4271 TCR3), a CDR2 comprising the amino acid sequence of SEQ ID NO: 25 (CDR2 of β chain of 4271 TCR3), and a CDR3 comprising the amino acid sequence of SEQ ID NO: 26 (CDR3 of β chain of 4271 TCR3).

In another embodiment of the invention, the TCR comprises a first polypeptide chain comprising a CDR1 comprising the amino acid sequence of SEQ ID NO: 31 (CDR1 of α chain of 4271 TCR4), a CDR2 comprising the amino acid sequence of SEQ ID NO: 32 (CDR2 of α chain of 4271 TCR4), and a CDR3 comprising the amino acid sequence of SEQ ID NO: 33 (CDR3 of α chain of 4271 TCR4), and a second polypeptide chain comprising a CDR1 comprising the amino acid sequence of SEQ ID NO: 34 (CDR1 of β chain of 4271 TCR4), a CDR2 comprising the amino acid sequence of SEQ ID NO: 35 (CDR2 of β chain of 4271 TCR4), and a CDR3 comprising the amino acid sequence of SEQ ID NO: 36 (CDR3 of β chain of 4271 TCR4).

In this regard, the inventive TCR can comprise any one or more of the amino acid sequences selected from the group consisting of SEQ ID NOs: 1-6, 11-16, 21-26, and 31-36. In an embodiment of the invention, the TCR comprises the amino acid sequences of: (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, or (l) all of SEQ ID NOs: 31-36. In an especially preferred embodiment, the TCR comprises the amino acid sequences of: (a) all of SEQ ID NOs: 1-6, (b) all of SEQ ID NOs: 11-16, (c) all of SEQ ID NOs: 21-26, or (d) all of SEQ ID NOs: 31-36.

In an embodiment of the invention, the TCR comprises an amino acid sequence of a variable region of a TCR comprising the CDRs set forth above. In this regard, the TCR can comprise the amino acid sequence of: (i) SEQ ID NO: 7 (predicted sequence of variable region of α chain of 4271 TCR1 without N-terminal signal peptide); (ii) SEQ ID NO: 8 (predicted sequence of variable region of β chain of 4271 TCR1 without N-terminal signal peptide); (iii) SEQ ID NO: 9 (variable region of α chain of 4271 TCR1 with N-terminal signal peptide); (iv) SEQ ID NO: 10 (variable region of β chain of 4271 TCR1 with N-terminal signal peptide); (v) SEQ ID NO: 17 (predicted sequence of variable region of α chain of 4271 TCR2 without N-terminal signal peptide); (vi) SEQ ID NO: 18 (predicted sequence of variable region of β chain of 4271 TCR2 without N-terminal signal peptide); (vii) SEQ ID NO: 19 (variable region of α chain of 4271 TCR2 with N-terminal signal peptide); (viii) SEQ ID NO: 20 (variable region of β chain of 4271 TCR2 with N-terminal signal peptide); (ix) SEQ ID NO: 27 (predicted sequence of variable region of α chain of 4271 TCR3 without N-terminal signal peptide); (x) SEQ ID NO: 28 (predicted sequence of variable region of β chain of 4271 TCR3 without N-terminal signal peptide); (xi) SEQ ID NO: 29 (variable region of α chain of 4271 TCR3 with N-terminal signal peptide); (xii) SEQ ID NO: 30 (variable region of β chain of 4271 TCR3 with N-terminal signal peptide); (xiii) SEQ ID NO: 37 (predicted sequence of variable region of α chain of 4271 TCR4 without N-terminal signal peptide); (xiv) SEQ ID NO: 38 (predicted sequence of variable region of β chain of 4271 TCR4 without N-terminal signal peptide); (xv) SEQ ID NO: 39 (variable region of α chain of 4271 TCR4 with N-terminal signal peptide); (xvi) SEQ ID NO: 40 (variable region of β chain of 4271 TCR4 with N-terminal signal peptide); (xvii) both of SEQ ID NOs: 7 and 8; (xviii) both of SEQ ID NOs: 9 and 10; (xix) both of SEQ ID NOs: 17 and 18; (xx) both of SEQ ID NOs: 19 and 20; (xxi) both of SEQ ID NOs: 27 and 28; (xxii) both of SEQ ID NOs: 29 and 30; (xxiii) both of SEQ ID NOs: 37 and 38; or (xxiv) both of SEQ ID NOs: 39 and 40. Preferably, the TCR comprises the amino acid sequences of (i) both of SEQ ID NOs: 7 and 8, (ii) both of SEQ ID NOs: 9 and 10, (iii) both of SEQ ID NOs: 17 and 18, (iv) both of SEQ ID NOs: 19 and 20, (v) both of SEQ ID NOs: 27 and 28, (vi) both of SEQ ID NOs: 29 and 30, (vii) both of SEQ ID NOs: 37 and 38, or (viii) both of SEQ ID NOs: 39 and 40.

The inventive TCRs may further comprise an α chain constant region and a β chain constant region. The constant region may be derived from any suitable species such as, e.g., human or mouse. In an embodiment of the invention, the TCRs further comprise murine α and β chain constant regions or human α and β chain constant regions. As used herein, the term "murine" or "human," when referring to a TCR or any component of a TCR described herein (e.g., CDR, variable region, constant region, α chain, and/or β chain), means a TCR (or component thereof) which is derived from a mouse or a human, respectively, i.e., a TCR (or component thereof) that originated from or was, at one time, expressed by a mouse T cell or a human T cell, respectively.

An embodiment of the invention provides a chimeric TCR comprising a human variable region and a murine constant region, wherein the TCR has antigenic specificity for a mutated human RAS amino acid sequence with a substitution of glycine at position 12 with aspartic acid. The murine constant region may provide any one or more advantages. For example, the murine constant region may diminish mispairing of the inventive TCR with the endogenous TCRs of the host cell into which the inventive TCR is introduced. Alternatively or additionally, the murine constant region may increase expression of the inventive TCR as compared to the same TCR with a human constant region. The chimeric TCR may comprise the amino acid sequence of SEQ ID NO: 53 (WT murine α chain constant region), SEQ ID NO: 54 (WT murine β chain constant region), or both SEQ ID NOs: 53 and 54. Preferably, the inventive TCR comprises the amino acid sequences of both of SEQ ID NOs: 53 and 54. The chimeric TCR may comprise any of the murine constant regions described herein in combination with any of the CDR regions as described herein with respect to other aspects of the invention. In this regard, the TCR may comprise the amino acid sequences of: (a) all of SEQ ID NOs: 1-3 and 53, (b) all of SEQ ID NOs: 4-6 and 54, (c) all of SEQ ID NOs: 1-6 and 53-54, (d) all of SEQ ID NOs: 11-13 and 53, (e) all of SEQ ID NOs: 14-16 and 54, (f) all of SEQ ID NOs: 11-16 and 53-54, (g) all of SEQ ID NOs: 21-23 and 53, (h) all of SEQ ID NOs: 24-26 and 54, (i) all of SEQ ID NOs: 21-26 and 53-54, (j) all of SEQ ID NOs: 31-33 and 53, (k) all of SEQ ID NOs: 34-36 and 54, or (l) all of SEQ ID NOs: 31-36 and 53-54. In another embodiment of the invention, the chimeric TCR may comprise any of the murine constant regions described herein in combination with any of the variable regions described herein with respect to other aspects of the invention. In this regard, the TCR may comprise the amino acid sequences of: (i) both of SEQ ID NOs: 7 and 53, (ii) both of SEQ ID NOs: 8 and 54, (iii) both of SEQ ID NOs: 9 and 53, (iv) both of SEQ ID NOs: 10 and 54, (v) both of SEQ ID NOs: 17 and 53, (vi) both of SEQ ID NOs: 18 and 54, (vii) both of SEQ ID NOs: 19 and 53, (viii) both of SEQ ID NOs: 20 and 54, (ix) both of SEQ ID NOs: 27 and 53, (x) both of SEQ ID NOs: 28 and 54, (xi) both of SEQ ID NOs: 29 and 53, (xii) both of SEQ ID NOs: 30 and 54, (xiii) both of SEQ ID NOs: 37 and 53, (xiv) both of SEQ ID NOs: 38 and 54, (xv) both of SEQ ID NOs: 39 and 53, (xvi) both of SEQ ID NOs: 40 and 54, (xvii) all of SEQ ID NOs: 7-8 and 53-54, (xviii) all of SEQ ID NOs: 9-10 and 53-54, (xix) all of SEQ ID NOs: 17-18 and 53-54, (xx) all of SEQ ID NOs: 19-20 and 53-54, (xxi) all of SEQ ID NOs: 27-28 and 53-54, (xxii) all of SEQ ID NOs: 29-30 and 53-54, (xxiii) all of SEQ ID NOs: 37-38 and 53-54, or (xxiv) all of SEQ ID NOs: 39-40 and 53-54.

In an embodiment of the invention, the TCR comprises a substituted constant region. In this regard, the TCR may comprise the amino acid sequence of any of the TCRs described herein with one, two, three, or four amino acid substitution(s) in the constant region of one or both of the α and β chain. Preferably, the TCR comprises a murine constant region with one, two, three, or four amino acid substitution(s) in the murine constant region of one or both of the α and β chains. In an especially preferred embodiment, the TCR comprises a murine constant region with one, two, three, or four amino acid substitution(s) in the murine constant region of the α chain and one amino acid substitution in the murine constant region of the β chain. In some embodiments, the TCRs comprising the substituted constant region advantageously provide one or more of increased recognition of G12D RAS' targets, increased expression by a host cell, diminished mispairing with endogenous TCRs, and increased anti-tumor activity as compared to the parent TCR comprising an unsubstituted (wild-type) constant region. In general, the substituted amino acid sequences of the murine constant regions of the TCR α and β chains, SEQ ID NOs: 49 and 50, respectively, correspond with all or portions of the unsubstituted murine constant region amino acid sequences SEQ ID NOs: 53 and 54, respectively, with SEQ ID NO: 49 having one, two, three, or four amino acid substitution(s) when compared to SEQ ID NO: 53 and SEQ ID NO: 50 having one amino acid substitution when compared to SEQ ID NO: 54. In this regard, an embodiment of the invention provides a TCR comprising the amino acid sequences of (a) SEQ ID NO: 49 (constant region of α chain), wherein (i) X at position 48 is Thr or Cys; (ii) X at position 112 is Ser, Ala, Val, Leu, Ile, Pro, Phe, Met, or Trp; (iii) X at position 114 is Met, Ala, Val, Leu, Ile, Pro, Phe, or Trp; and (iv) X at position 115 is Gly, Ala, Val, Leu, Ile, Pro, Phe, Met, or Trp; (b) SEQ ID NO: 50 (constant region of β chain), wherein X at position 57 is Ser or Cys; or (c) both of SEQ ID NOs: 49 and 50. In an embodiment of the invention, the TCR comprising SEQ ID NO: 49 does not comprise SEQ ID NO: 53 (unsubstituted murine constant region of α chain). In an embodiment of the invention, the TCR comprising SEQ ID NO: 50 does not comprise SEQ ID NO: 54 (unsubstituted murine constant region of β chain).

In an embodiment of the invention, the TCR comprises an α chain comprising a variable region and a constant region and a β chain comprising a variable region and a constant region. In this regard, the TCR may comprise (a) an α chain comprising the amino acid sequence of SEQ ID NO: 55 (α chain of 4271 TCR1 with N-terminal signal peptide), wherein: (i) X at position 184 of SEQ ID NO: 55 is Thr or Cys: (ii) X at position 248 of SEQ ID NO: 55 is Ser, Ala, Val, Leu, Ile, Pro, Phe, Met, or Trp; (iii) X at position 250 of SEQ ID NO: 55 is Met, Ala, Val, Leu, Ile, Pro, Phe, or Trp; and (iv) X at position 251 of SEQ ID NO: 55 is Gly, Ala, Val, Leu, Ile, Pro, Phe, Met, or Trp; (b) a β chain comprising the amino acid sequence of SEQ ID NO: 56 (β chain of 4271 TCR1 with N-terminal signal peptide), wherein X at position 199 of SEQ ID NO: 56 is Ser or Cys; (c) both of SEQ ID NOs: 55 and 56; (d) an α chain comprising the amino acid sequence of SEQ ID NO: 57 (predicted sequence of α chain of 4271 TCR1 without N-terminal signal peptide), wherein: (i) X at position 165 of SEQ ID NO: 57 is Thr or Cys; (ii) X at position 229 of SEQ ID NO: 57 is Ser, Ala, Val, Leu, Ile, Pro, Phe, Met, or Trp; (iii) X at position 231 of SEQ ID NO: 57 is Met, Ala, Val, Leu, Ile, Pro, Phe, or Trp; and (iv) X at position 232 of SEQ ID NO: 57 is Gly, Ala, Val, Leu, Ile, Pro, Phe, Met, or Trp; (e) a β chain comprising the amino acid sequence of SEQ ID NO: 58 (predicted sequence of chain of 4271 TCR1 without N-terminal signal peptide), wherein X at position 175 of SEQ ID NO: 58 is Ser or Cys; (f) both of SEQ ID NOs: 57 and 58; (g) SEQ ID NO: 59 (α chain of cysteine-substituted, LVL-modified 4271 TCR1 with N-terminal signal sequence); (h) SEQ ID NO: 60 (β chain of cysteine-substituted, LVL-modified 4271 TCR1 with N-terminal signal sequence); (i) SEQ ID NO: 61 (predicted sequence of α chain of cysteine-substituted, LVL-modified 4271 TCR1 without N-terminal signal sequence); (j) SEQ ID NO: 62 (predicted sequence of β chain of cysteine-substituted, LVL-modified 4271 TCR1 without N-terminal signal sequence); (k) both of SEQ ID NOs: 59 and 60; (l) both of SEQ ID NOs: 61 and 62; (m) an α chain comprising the amino acid sequence of SEQ ID NO: 63 (α chain of 4271 TCR2 with N-terminal signal peptide), wherein: (i) X at position 182 of SEQ ID NO: 63 is Thr or Cys: (ii) X at position 246 of SEQ ID NO: 63 is Ser, Ala, Val, Leu, Ile, Pro, Phe, Met, or Trp; (iii) X at position 248 of SEQ ID NO: 63 is Met, Ala, Val, Leu, Ile, Pro, Phe, or Trp; and (iv) X at position 249 of SEQ ID NO: 63 is Gly, Ala, Val, Leu, Ile, Pro, Phe, Met, or Trp; (n) a β chain comprising the amino acid sequence of SEQ ID NO: 64 (β chain of 4271 TCR2 with N-terminal signal peptide), wherein X at position 197 of SEQ ID NO: 64 is Ser or Cys; (o) both of SEQ ID NOs: 63 and 64; (p) an α chain comprising the amino acid sequence of SEQ ID NO: 65 (predicted sequence of α chain of 4271 TCR2 without N-terminal signal peptide), wherein: (i) X at position 164 of SEQ ID NO: 65 is Thr or Cys: (ii) X at position 228 of SEQ ID NO: 65 is Ser, Ala, Val, Leu, Ile, Pro, Phe, Met, or Trp; (iii) X at position 230 of SEQ ID NO: 65 is Met, Ala, Val, Leu, Ile, Pro, Phe, or Trp; and (iv) X at position 231 of SEQ ID NO: 65 is Gly, Ala, Val, Leu, Ile, Pro, Phe, Met, or Trp; (q) a β chain comprising the amino acid sequence of SEQ ID NO: 66 (predicted sequence of β chain of 4271 TCR2 without N-terminal signal peptide), wherein X at position 173 of SEQ ID NO: 66 is Ser or Cys; (r) both of SEQ ID NOs: 65 and 66; (s) SEQ ID NO: 67 (α chain of cysteine-substituted, LVL-modified 4271 TCR2 with N-terminal signal sequence); (t) SEQ ID NO: 68 (β chain of cysteine-substituted, LVL-modified 4271 TCR2 with N-terminal signal sequence); (u) SEQ ID NO: 69 (predicted sequence of α chain of cysteine-substituted, LVL-modified 4271 TCR2 without N-terminal signal sequence); (v) SEQ ID NO: 70 (predicted sequence of β chain of cysteine-substituted, LVL-modified 4271 TCR2 without N-terminal signal sequence); (w) both of SEQ ID NOs: 67 and 68; (x) both of SEQ ID NOs: 69 and 70; (y) an α chain comprising the amino acid sequence of SEQ ID NO: 71 (α chain of 4271 TCR3 with N-terminal signal peptide), wherein: (i) X at position 187 of SEQ ID NO: 71 is Thr or Cys: (ii) X at position 251 of SEQ ID NO: 71 is Ser, Ala, Val, Leu, Ile, Pro, Phe, Met, or Trp: (iii) X at position 253 of SEQ ID NO: 71 is Met, Ala, Val, Leu, Ile, Pro, Phe, or Trp; and (iv) X at position 254 of SEQ ID NO: 71 is Gly, Ala, Val, Leu, Ile, Pro, Phe, Met, or Trp; (z) a β chain comprising the amino acid sequence of SEQ ID NO: 72 (β chain of 4271 TCR3 with N-terminal signal peptide), wherein X at position 191 of SEQ ID NO: 72 is Ser or Cys; (aa) both of SEQ ID NOs: 71 and 72; (bb) an α chain comprising the amino acid sequence of SEQ ID NO: 73 (predicted sequence of α chain of 4271 TCR3 without N-terminal signal peptide), wherein: (i) X at position 168 of SEQ ID NO: 73 is Thr or Cys: (ii) X at position 232 of SEQ ID NO: 73 is Ser, Ala, Val, Leu, Ile, Pro, Phe, Met, or Trp: (iii) X at position 234 of SEQ ID NO: 73 is Met, Ala, Val, Leu, Ile, Pro, Phe, or Trp; and (iv) X at position 235 of SEQ ID NO: 73 is Gly, Ala, Val, Leu, Ile, Pro, Phe, Met, or Trp; (cc) a β chain comprising the amino acid sequence of SEQ ID NO: 74 (predicted sequence of β chain of 4271 TCR3 without N-terminal signal peptide), wherein X at position 173 of SEQ ID NO: 74 is Ser or Cys; (dd) both of SEQ ID NOs: 73 and 74; (ee) SEQ ID NO: 75 (α chain of cysteine-substituted, LVL-modified 4271 TCR3 with N-terminal signal sequence); (ff) SEQ ID NO: 76 (β chain of cysteine-substituted, LVL-modified 4271 TCR3 with N-terminal signal sequence); (gg) SEQ ID NO: 77 (predicted sequence of α chain of cysteine-substituted, LVL-modified 4271 TCR3 without N-terminal signal sequence); (hh) SEQ ID NO: 78 (predicted sequence of β chain of cysteine-substituted, LVL-modified 4271 TCR3 without N-terminal signal sequence); (ii) both of SEQ ID NOs: 75 and 76; (jj) both of SEQ ID NOs: 77 and 78; (kk) an α chain comprising the amino acid sequence of SEQ ID NO: 79 (α chain of 4271 TCR4 with N-terminal signal peptide), wherein: (i) X at position 175 of SEQ ID NO: 79 is Thr or Cys: (ii) X at position 239 of SEQ ID NO: 79 is Ser, Ala, Val, Leu, Ile, Pro, Phe, Met, or Trp: (iii) X at position 241 of SEQ ID NO: 79 is Met, Ala, Val, Leu, Ile, Pro, Phe, or Trp; and (iv) X at position 242 of SEQ ID NO: 79 is Gly, Ala, Val, Leu, Ile, Pro, Phe, Met, or Trp; (ll) a β chain comprising the amino acid sequence of SEQ ID NO: 80 (β chain of 4271 TCR4 with N-terminal signal peptide), wherein X at position 190 of SEQ ID NO: 80 is Ser or Cys; (mm) both of SEQ ID NOs: 79 and 80; (nn) an α chain comprising the amino acid sequence of SEQ ID NO: 81 (predicted sequence of α chain of 4271 TCR4 without N-terminal signal peptide), wherein: (i) X at position 159 of SEQ ID NO: 81 is Thr or Cys: (ii) X at position 223 of SEQ ID NO: 81 is Ser, Ala, Val, Leu, Ile, Pro, Phe, Met, or Trp: (iii) X at position 225 of SEQ ID NO: 81 is Met, Ala, Val, Leu, Ile, Pro, Phe, or Trp; and (iv) X at position 226 of SEQ ID NO: 81 is Gly, Ala, Val, Leu, Ile, Pro, Phe, Met, or Trp; (oo) a β chain comprising the amino acid sequence of SEQ ID NO: 82 (predicted sequence of β chain of 4271 TCR4 without N-terminal signal peptide), wherein X at position 172 of SEQ ID NO: 82 is Ser or Cys; (pp) both of SEQ ID NOs: 81 and 82; (qq) SEQ ID NO: 83 (α chain of cysteine-substituted, LVL-modified 4271 TCR4 with N-terminal signal sequence); (rr) SEQ ID NO: 84 (β chain of cysteine-substituted, LVL-modified 4271 TCR4 with N-terminal signal sequence); (ss) SEQ ID NO: 85 (predicted sequence of α chain of cysteine-substituted, LVL-modified 4271 TCR4 without N-terminal signal sequence); (tt) SEQ ID NO: 86 (predicted sequence of β chain of cysteine-substituted, LVL-modified 4271 TCR4 without N-terminal signal sequence); (uu) both of SEQ ID NOs: 83 and 84; or (vv) both of SEQ ID NOs: 85 and 86.

In an embodiment of the invention, the substituted constant region includes cysteine substitutions in the constant region of one or both of the α and β chains to provide a cysteine-substituted TCR. Opposing cysteines in the α and the β chains provide a disulfide bond that links the constant regions of the α and the β chains of the substituted TCR to one another and which is not present in a TCR comprising the unsubstituted murine constant regions. In this regard, the TCR may be a cysteine-substituted TCR in which one or both of the native Thr at position 48 (Thr48) of SEQ ID NO: 53 and the native Ser at position 57 (Ser57) of SEQ ID NO: 54 may be substituted with Cys. Preferably, both of the native Thr48 of SEQ ID NO: 53 and the native Ser57 of SEQ ID NO: 54 are substituted with Cys. Examples of cysteine-substituted TCR constant regions sequences are set forth in Table 2. In an embodiment of the invention, the cysteine-substituted TCR comprises (i) SEQ ID NO: 49, (ii) SEQ ID NO: 50, or (iii) both of SEQ ID NOs: 49 and 50, wherein both of SEQ ID NOs: 49 and 50 are as defined in Table 2. The cysteine-substituted TCRs of the invention may include the substituted constant region in addition to any of the CDRs or variable regions described herein.

In an embodiment of the invention, the cysteine-substituted, chimeric TCR comprises a full length α chain and a full-length β chain. Examples of cysteine-substituted, chimeric TCR α chain and β chain sequences are set forth in Table 2. In an embodiment of the invention, the TCR comprises: (i) SEQ ID NO: 49, (ii) SEQ ID NO: 50, (iii) SEQ ID NO: 55, (iv) SEQ ID NO: 56, (v) SEQ ID NO: 57, (vi) SEQ ID NO: 58, (vii) SEQ ID NO: 63, (viii) SEQ ID NO: 64, (ix) SEQ ID NO: 65, (x) SEQ ID NO: 66, (xi) SEQ ID NO: 71, (xii) SEQ ID NO: 72, (xiii) SEQ ID NO: 73, (xiv) SEQ ID NO: 74, (xv) SEQ ID NO: 79, (xvi) SEQ ID NO: 80, (xvii) SEQ ID NO: 81, (xviii) SEQ ID NO: 82, (xix) both of SEQ ID NOs: 49 and 50, (xx) both of SEQ ID NOs: 55 and 56, (xxi) both of SEQ ID NOs: 57 and 58, (xxii) both of SEQ ID NOs: 63 and 64, (xxiii) both of SEQ ID NOs: 65 and 66, (xxiv) both of SEQ ID NOs: 71 and 72, (xxv) both of SEQ ID NOs: 73 and 74, (xxvi) both of SEQ ID NOs: 79 and 80, or (xxvii) both of SEQ ID NOs: 81 and 82, wherein all of SEQ ID NOs: 49-50, 55-58, 63-66, 71-74, and 79-82 are as defined in Table 2.

TABLE 2

| SEQ ID NO: | Definitions of "X" |
| --- | --- |
| SEQ ID NO: 49 (constant region α chain) | X at position 48 is Cys, X at position 112 is Ser, X at position 114 is Met, and X at position 115 is Gly. |
| SEQ ID NO: 50 (constant region β chain) | X at position 57 is Cys |

TABLE 2-continued

| SEQ ID NO: | Definitions of "X" |
|---|---|
| SEQ ID NO: 55 (4271 TCR1 α chain with N-terminal signal peptide) | X at position 184 is Cys, X at position 248 is Ser, X at position 250 is Met, and X at position 251 is Gly. |
| SEQ ID NO: 56 (4271 TCR1 β chain with N-terminal signal peptide) | X at position 199 is Cys |
| SEQ ID NO: 57 (4271 TCR1 α chain predicted sequence without N-terminal signal peptide) | X at position 165 is Cys, X at position 229 is Ser, X at position 231 is Met, and X at position 232 is Gly. |
| SEQ ID NO: 58 (4271 TCR1 β chain predicted sequence without N-terminal signal peptide) | X at position 175 is Cys |
| SEQ ID NO: 63 (4271 TCR2 α chain with N-terminal signal peptide) | X at position 182 is Cys, X at position 246 is Ser, X at position 248 is Met, and X at position 249 is Gly. |
| SEQ ID NO: 64 (4271 TCR2 β chain with N-terminal signal peptide) | X at position 197 is Cys |
| SEQ ID NO: 65 (4271 TCR2 α chain predicted sequence without N-terminal signal peptide) | X at position 164 is Cys, X at position 228 is Ser, X at position 230 is Met, and X at position 231 is Gly. |
| SEQ ID NO: 66 (4271 TCR2 β chain predicted sequence without N-terminal signal peptide) | X at position 173 is Cys |
| SEQ ID NO: 71 (4271 TCR3 α chain with N-terminal signal peptide) | X at position 187 is Cys, X at position 251 is Ser, X at position 253 is Met, and X at position 254 is Gly. |
| SEQ ID NO: 72 (4271 TCR3 β chain with N-terminal signal peptide) | X at position 191 is Cys |
| SEQ ID NO: 73 (4271 TCR3 α chain predicted sequence without N-terminal signal peptide) | X at position 168 is Cys, X at position 232 is Ser, X at position 234 is Met, and X at position 235 is Gly. |
| SEQ ID NO: 74 (4271 TCR3 β chain predicted sequence without N-terminal signal peptide) | X at position 173 is Cys |
| SEQ ID NO: 79 (4271 TCR4 α chain with N-terminal signal peptide) | X at position 175 is Cys, X at position 239 is Ser, X at position 241 is Met, and X at position 242 is Gly. |
| SEQ ID NO: 80 (4271 TCR4 β chain with N-terminal signal peptide) | X at position 190 is Cys |
| SEQ ID NO: 81 (4271 TCR4 α chain predicted sequence without N-terminal signal peptide) | X at position 159 is Cys, X at position 223 is Ser, X at position 225 is Met, and X at position 226 is Gly. |

TABLE 2-continued

| SEQ ID NO: | Definitions of "X" |
|---|---|
| SEQ ID NO: 82 (4271 TCR4 β chain predicted sequence without N-terminal signal peptide) | X at position 172 is Cys |

In an embodiment of the invention, the substituted amino acid sequence includes substitutions of one, two, or three amino acids in the transmembrane (TM) domain of the constant region of the α chain with a hydrophobic amino acid to provide a hydrophobic amino acid-substituted TCR (also referred to herein as an "LVL-modified TCR"). The hydrophobic amino acid substitution(s) in the TM domain of the TCR may increase the hydrophobicity of the TM domain of the TCR as compared to a TCR that lacks the hydrophobic amino acid substitution(s) in the TM domain. In this regard, the TCR is an LVL-modified TCR in which one, two, or three of the native Ser112, Met114, and Gly115 of SEQ ID NO: 53 may, independently, be substituted with Ala, Val, Leu, Ile, Pro, Phe, Met, or Trp; preferably with Leu, Ile, or Val. Preferably, all three of the native Ser112, Met114, and Gly115 of SEQ ID NO: 53 may, independently, be substituted with Ala, Val, Leu, Ile, Pro, Phe, Met, or Trp; preferably with Leu, Ile, or Val. In an embodiment of the invention, the LVL-modified TCR comprises (i) SEQ ID NO: 49, (ii) SEQ ID NO: 50, or (iii) both of SEQ ID NOs: 49 and 50, wherein both of SEQ ID NOs: 49 and 50 are as defined in Table 3. The LVL-modified TCRs of the invention may include the substituted constant region in addition to any of the CDRs or variable regions described herein.

In an embodiment of the invention, the LVL-modified TCR comprises a full length α chain and a full-length β chain. Examples of LVL-modified TCR α chain and β chain sequences are set forth in Table 3. In an embodiment of the invention, the TCR comprises: (i) SEQ ID NO: 49, (ii) SEQ ID NO: 50, (iii) SEQ ID NO: 55, (iv) SEQ ID NO: 56, (v) SEQ ID NO: 57, (vi) SEQ ID NO: 58, (vii) SEQ ID NO: 63, (viii) SEQ ID NO: 64, (ix) SEQ ID NO: 65, (x) SEQ ID NO: 66, (xi) SEQ ID NO: 71, (xii) SEQ ID NO: 72, (xiii) SEQ ID NO: 73, (xiv) SEQ ID NO: 74, (xv) SEQ ID NO: 79, (xvi) SEQ ID NO: 80, (xvii) SEQ ID NO: 81, (xviii) SEQ ID NO: 82, (xix) both of SEQ ID NOs: 49 and 50, (xx) both of SEQ ID NOs: 55 and 56, (xxi) both of SEQ ID NOs: 57 and 58, (xxii) both of SEQ ID NOs: 63 and 64, (xxiii) both of SEQ ID NOs: 65 and 66, (xxiv) both of SEQ ID NOs: 71 and 72, (xxv) both of SEQ ID NOs: 73 and 74, (xxvi) both of SEQ ID NOs: 79 and 80, (xxvii) both of SEQ ID NOs: 81 and 82, wherein all of SEQ ID NOs: 49-50, 55-58, 63-66, 71-74, and 79-82 are as defined in Table 3.

TABLE 3

| SEQ ID NO: | Definitions of "X" |
|---|---|
| SEQ ID NO: 49 (constant region α chain) | X at position 48 is Thr; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; especially preferably wherein X at position 115 is Val; wherein SEQ ID NO: 49 does not comprise SEQ ID NO: 53 (unsubstituted α chain constant region) |

TABLE 3-continued

| SEQ ID NO: | Definitions of "X" |
|---|---|
| SEQ ID NO: 50 (constant region β chain) | X at position 57 is Ser |
| SEQ ID NO: 55 (4271 TCR1 α chain) (with N-terminal signal peptide) | X at position 184 is Thr;<br>X at position 248 is Ser, Ala, Val, Leu, Ile, Pro, Phe, Met, or Trp;<br>preferably wherein X at position 248 is Leu, Ile, or Val;<br>especially preferably wherein X at position 248 is Leu;<br>X at position 250 is Met, Ala, Val, Leu, Ile, Pro, Phe, or Trp;<br>preferably wherein X at position 250 is Leu, Ile, or Val;<br>especially preferably wherein X at position 250 is Ile; and<br>X at position 251 is Gly, Ala, Val, Leu, Ile, Pro, Phe, Met, or Trp;<br>preferably wherein X at position 251 is Leu, Ile, or Val;<br>especially preferably wherein X at position 251 is Val,<br>wherein SEQ ID NO: 55 does not comprise SEQ ID NO: 53 (unsubstituted α chain constant region) |
| SEQ ID NO: 56 (4271 TCR1 β chain) (with N-terminal signal peptide) | X at position 199 is Ser |
| SEQ ID NO: 57 (4271 TCR1 α chain) (predicted sequence without N-terminal signal peptide) | X at position 165 is Thr;<br>X at position 229 is Ser, Ala, Val, Leu, Ile, Pro, Phe, Met, or Trp;<br>preferably wherein X at position 229 is Leu, Ile, or Val;<br>especially preferably wherein X at position 229 is Leu;<br>X at position 231 is Met, Ala, Val, Leu, Ile, Pro, Phe, or Trp;<br>preferably wherein X at position 231 is Leu, Ile, or Val;<br>especially preferably wherein X at position 231 is Ile; and<br>X at position 232 is Gly, Ala, Val, Leu, Ile, Pro, Phe, Met, or Trp;<br>preferably wherein X at position 232 is Leu, Ile, or Val;<br>especially preferably wherein X at position 232 is Val,<br>wherein SEQ ID NO: 57 does not comprise SEQ ID NO: 53 (unsubstituted α chain constant region) |
| SEQ ID NO: 58 (4271 TCR1 β chain) (predicted sequence without N-terminal signal peptide) | X at position 175 is Ser |
| SEQ ID NO: 63 (4271 TCR2 α chain with N-terminal signal peptide) | X at position 182 is Thr;<br>X at position 246 is Ser, Ala, Val, Leu, Ile, Pro, Phe, Met, or Trp;<br>preferably wherein X at position 246 is Leu, Ile, or Val;<br>especially preferably wherein X at position 246 is Leu;<br>X at position 248 is Met, Ala, Val, Leu, Ile, Pro, Phe, or Trp;<br>preferably wherein X at position 248 is Leu, Ile, or Val;<br>especially preferably wherein X at position 248 is Ile; and<br>X at position 249 is Gly, Ala, Val, Leu, Ile, Pro, Phe, Met, or Trp;<br>preferably wherein X at position 249 is Leu, Ile, or Val;<br>especially preferably wherein X at position 249 is Val,<br>wherein SEQ ID NO: 63 does not comprise SEQ ID NO: 53 (unsubstituted α chain constant region) |
| SEQ ID NO: 64 (4271 TCR2 β chain with N-terminal signal peptide) | X at position 197 is Ser |
| SEQ ID NO: 65 (4271 TCR2 α chain predicted sequence without N-terminal signal peptide) | X at position 164 is Thr;<br>X at position 228 is Ser, Ala, Val, Leu, Ile, Pro, Phe, Met, or Trp;<br>preferably wherein X at position 228 is Leu, Ile, or Val;<br>especially preferably wherein X at position 228 is Leu;<br>X at position 230 is Met, Ala, Val, Leu, Ile, Pro, Phe, or Trp;<br>preferably wherein X at position 230 is Leu, Ile, or Val;<br>especially preferably wherein X at position 230 is Ile; and<br>X at position 231 is Gly, Ala, Val, Leu, Ile, Pro, Phe, Met, or Trp;<br>preferably wherein X at position 231 is Leu, Ile, or Val;<br>especially preferably wherein X at position 231 is Val,<br>wherein SEQ ID NO: 65 does not comprise SEQ ID NO: 53 (unsubstituted α chain constant region) |
| SEQ ID NO: 66 (4271 TCR2 β chain predicted sequence without N-terminal signal peptide) | X at position 173 is Ser |
| SEQ ID NO: 71 (4271 TCR3 α chain with N-terminal signal peptide) | X at position 187 is Thr;<br>X at position 251 is Ser, Ala, Val, Leu, Ile, Pro, Phe, Met, or Trp;<br>preferably wherein X at position 251 is Leu, Ile, or Val;<br>especially preferably wherein X at position 251 is Leu;<br>X at position 253 is Met, Ala, Val, Leu, Ile, Pro, Phe, or Trp;<br>preferably wherein X at position 253 is Leu, Ile, or Val;<br>especially preferably wherein X at position 253 is Ile; and |

TABLE 3-continued

| SEQ ID NO: | Definitions of "X" |
|---|---|
| | X at position 254 is Gly, Ala, Val, Leu, Ile, Pro, Phe, Met, or Trp; preferably wherein X at position 254 is Leu, Ile, or Val; especially preferably wherein X at position 254 is Val, wherein SEQ ID NO: 71 does not comprise SEQ ID NO: 53 (unsubstituted α chain constant region) |
| SEQ ID NO: 72 (4271 TCR3 β chain with N-terminal signal peptide) | X at position 191 is Ser |
| SEQ ID NO: 73 (4271 TCR3 α chain predicted sequence without N-terminal signal peptide) | X at position 168 is Thr; X at position 232 is Ser, Ala, Val, Leu, Ile, Pro, Phe, Met, or Trp; preferably wherein X at position 232 is Leu, Ile, or Val; especially preferably wherein X at position 232 is Leu; X at position 234 is Met, Ala, Val, Leu, Ile, Pro, Phe, or Trp; preferably wherein X at position 234 is Leu, Ile, or Val; especially preferably wherein X at position 234 is Ile; and X at position 235 is Gly, Ala, Val, Leu, Ile, Pro, Phe, Met, or Trp; preferably wherein X at position 235 is Leu, Ile, or Val; especially preferably wherein X at position 235 is Val, wherein SEQ ID NO: 73 does not comprise SEQ ID NO: 53 (unsubstituted α chain constant region) |
| SEQ ID NO: 74 (4271 TCR3 β chain predicted sequence without N-terminal signal peptide) | X at position 173 is Ser |
| SEQ ID NO: 79 (4271 TCR4 α chain with N-terminal signal peptide) | X at position 175 is Thr; X at position 239 is Ser, Ala, Val, Leu, Ile, Pro, Phe, Met, or Trp; preferably wherein X at position 239 is Leu, Ile, or Val; especially preferably wherein X at position 239 is Leu; X at position 241 is Met, Ala, Val, Leu, Ile, Pro, Phe, or Trp; preferably wherein X at position 241 is Leu, Ile, or Val; especially preferably wherein X at position 241 is Ile; and X at position 242 is Gly, Ala, Val, Leu, Ile, Pro, Phe, Met, or Trp; preferably wherein X at position 242 is Leu, Ile, or Val; especially preferably wherein X at position 242 is Val, wherein SEQ ID NO: 79 does not comprise SEQ ID NO: 53 (unsubstituted α chain constant region) |
| SEQ ID NO: 80 (4271 TCR4 β chain with N-terminal signal peptide) | X at position 190 is Ser |
| SEQ ID NO: 81 (4271 TCR4 α chain predicted sequence without N-terminal signal peptide) | X at position 159 is Thr; X at position 223 is Ser, Ala, Val, Leu, Ile, Pro, Phe, Met, or Trp; preferably wherein X at position 223 is Leu, Ile, or Val; especially preferably wherein X at position 223 is Leu; X at position 225 is Met, Ala, Val, Leu, Ile, Pro, Phe, or Trp; preferably wherein X at position 225 is Leu, Ile, or Val; especially preferably wherein X at position 225 is Ile; and X at position 226 is Gly, Ala, Val, Leu, Ile, Pro, Phe, Met, or Trp; preferably wherein X at position 226 is Leu, Ile, or Val; especially preferably wherein X at position 226 is Val, wherein SEQ ID NO: 81 does not comprise SEQ ID NO: 53 (unsubstituted α chain constant region) |
| SEQ ID NO: 82 (4271 TCR4 β chain predicted sequence without N-terminal signal peptide) | X at position 172 is Ser |

In an embodiment of the invention, the substituted amino acid sequence includes the cysteine substitutions in the constant region of one or both of the α and β chains in combination with the substitution(s) of one, two, or three amino acids in the transmembrane (TM) domain of the constant region of the α chain with a hydrophobic amino acid (also referred to herein as "cysteine-substituted, LVL-modified TCR"). In this regard, the TCR is a cysteine-substituted, LVL-modified, chimeric TCR in which the native Thr48 of SEQ ID NO: 53 is substituted with Cys; one, two, or three of the native Ser112, Met114, and Gly115 of SEQ ID NO: 53 are, independently, substituted with Ala, Val, Leu, Ile, Pro, Phe, Met, or Trp; preferably with Leu, Ile, or Val; and the native Ser57 of SEQ ID NO: 54 is substituted with Cys. Preferably, all three of the native Ser112, Met114, and Gly115 of SEQ ID NO: 53 may, independently, be substituted with Ala, Val, Leu, Ile, Pro, Phe, Met, or Trp; preferably with Leu, Ile, or Val. In an embodiment of the invention, the cysteine-substituted, LVL-modified TCR comprises (i) SEQ ID NO: 49, (ii) SEQ ID NO: 50, or (iii) both of SEQ ID NOs: 49 and 50, wherein both of SEQ ID NOs: 49 and 50 are as defined in Table 4. The cysteine-substituted, LVL-modified TCRs of the invention may include the substituted constant region in addition to any of the CDRs or variable regions described herein.

In an embodiment, the cysteine-substituted, LVL-modified TCR comprises a full-length α chain and a full-length β chain. Examples of cysteine-substituted, LVL-modified TCR α chain and β chain sequences are set forth in Tables 4 and 7. In an embodiment of the invention, the TCR comprises: (1) SEQ ID NO: 49, (2) SEQ ID NO: 50, (3) SEQ ID NO: 55, (4) SEQ ID NO: 56, (5) SEQ ID NO: 57, (6) SEQ ID NO: 58, (7) SEQ ID NO: 63, (8) SEQ ID NO: 64, (9) SEQ ID NO: 65, (10) SEQ ID NO: 66, (11) SEQ ID NO: 71, (12) SEQ ID NO: 72, (13) SEQ ID NO: 73, (14) SEQ ID NO: 74, (15) SEQ ID NO: 79, (16) SEQ ID NO: 80, (17) SEQ ID NO: 81, (18) SEQ ID NO: 82, (19) both of SEQ ID NOs: 49 and 50, (20) both of SEQ ID NOs: 55 and 56, (21) both of SEQ ID NOs: 57 and 58, (22) both of SEQ ID NOs: 63 and 64, (23) both of SEQ ID NOs: 65 and 66, (24) both of SEQ ID NOs: 71 and 72, (25) both of SEQ ID NOs: 73 and 74, (26) both of SEQ ID NOs: 79 and 80, (27) both of SEQ ID NOs: 81 and 82, (28) SEQ ID NO: 59; (29) SEQ ID NO: 60; (30) both of SEQ ID NOs: 59 and 60; (31) SEQ ID NO: 61; (32) SEQ ID NO: 62; (33) both of SEQ ID NOs: 61 and 62; (34) SEQ ID NO: 67; (35) SEQ ID NO: 68; (36) both of SEQ ID NOs: 67 and 68; (37) SEQ ID NO: 69; (38) SEQ ID NO: 70; (39) both of SEQ ID NOs: 69 and 70; (40) SEQ ID NO: 75; (41) SEQ ID NO: 76; (42) both of SEQ ID NOs: 75 and 76; (43) SEQ ID NO: 77; (44) SEQ ID NO: 78; (45) both of SEQ ID NOs: 77 and 78; (46) SEQ ID NO: 83; (47) SEQ ID NO: 84; (48) both of SEQ ID NOs: 83 and 84; (49) SEQ ID NO: 85; (50) SEQ ID NO: 86; or (51) both of SEQ ID NOs: 85 and 86, wherein all of SEQ ID NOs: 49-50, 55-58, 63-66, 71-74, and 79-82 are as defined in Table 4.

TABLE 4

| SEQ ID NO: | Definitions of "X" |
| --- | --- |
| SEQ ID NO: 49 (constant region α chain) | X at position 48 is Cys; X at position 112 is Ser, Ala, Val, Leu, Ile, Pro, Phe, Met, or Trp; preferably wherein X at position 112 is Leu, Ile, or Val; especially preferably wherein X at position 112 is Leu; X at position 114 is Met, Ala, Val, Leu, Ile, Pro, Phe, or Trp; preferably wherein X at position 114 is Leu, Ile, or Val; especially preferably wherein X at position 114 is Ile; and X at position 115 is Gly, Ala, Val, Leu, Ile, Pro, Phe, Met, or Trp; preferably wherein X at position 115 is Leu, Ile, or Val; and especially preferably wherein X at position 115 is Val, wherein SEQ ID NO: 49 does not simultaneously comprise all of Ser at position 112, Met at position 114, and Gly at position 115. |
| SEQ ID NO: 50 (constant region β chain) | X at position 57 is Cys |
| SEQ ID NO: 55 (4271 TCR1 α chain) (with N-terminal signal peptide) | X at position 184 is Cys; X at position 248 is Ser, Ala, Val, Leu, Ile, Pro, Phe, Met, or Trp; preferably wherein X at position 248 is Leu, Ile, or Val; especially preferably wherein X at position 248 is Leu; X at position 250 is Met, Ala, Val, Leu, Ile, Pro, Phe, or Trp; preferably wherein X at position 250 is Leu, Ile, or Val; especially preferably wherein X at position 250 is Ile; and X at position 251 is Gly, Ala, Val, Leu, Ile, Pro, Phe, Met, or Trp; preferably wherein X at position 251 is Leu, Ile, or Val; and especially preferably wherein X at position 251 is Val, wherein SEQ ID NO: 55 does not simultaneously comprise all of Ser at position 248, Met at position 250, and Gly at position 251. |
| SEQ ID NO: 56 (4271 TCR1 β chain) (with N-terminal signal peptide) | X at position 199 is Cys |
| SEQ ID NO: 57 (4271 TCR1 α chain) (predicted sequence without N-terminal signal peptide) | X at position 165 is Cys; X at position 229 is Ser, Ala, Val, Leu, Ile, Pro, Phe, Met, or Trp; preferably wherein X at position 229 is Leu, Ile, or Val; especially preferably wherein X at position 229 is Leu; X at position 231 is Met, Ala, Val, Leu, Ile, Pro, Phe, or Trp; preferably wherein X at position 231 is Leu, Ile, or Val; especially preferably wherein X at position 231 is Ile; and X at position 232 is Gly, Ala, Val, Leu, Ile, Pro, Phe, Met, or Trp; preferably wherein X at position 232 is Leu, Ile, or Val; and especially preferably wherein X at position 232 is Val, wherein SEQ ID NO: 57 does not simultaneously comprise all of Ser at position 229, Met at position 231, and Gly at position 232. |
| SEQ ID NO: 58 (4271 TCR1 β chain) (predicted sequence without N-terminal signal peptide) | X at position 175 is Cys |
| SEQ ID NO: 63 (4271 TCR2 α chain with N-terminal signal peptide) | X at position 182 is Cys; X at position 246 is Ser, Ala, Val, Leu, Ile, Pro, Phe, Met, or Trp; preferably wherein X at position 246 is Leu, Ile, or Val; especially preferably wherein X at position 246 is Leu; X at position 248 is Met, Ala, Val, Leu, Ile, Pro, Phe, or Trp; preferably wherein X at position 248 is Leu, Ile, or Val; especially preferably wherein X at position 248 is Ile; and X at position 249 is Gly, Ala, Val, Leu, Ile, Pro, Phe, Met, or Trp; preferably wherein X at position 249 is Leu, Ile, or Val; and especially preferably wherein X at position 249 is Val, wherein SEQ ID NO: 63 does not simultaneously comprise all of Ser at position 246, Met at position 248, and Gly at position 249. |

TABLE 4-continued

| SEQ ID NO: | Definitions of "X" |
|---|---|
| SEQ ID NO: 64<br>(4271 TCR2 β chain<br>with N-terminal signal<br>peptide) | X at position 197 is Cys |
| SEQ ID NO: 65<br>(4271 TCR2 α chain<br>predicted sequence<br>without N-terminal<br>signal peptide) | X at position 164 is Cys;<br>X at position 228 is Ser, Ala, Val, Leu, Ile, Pro, Phe, Met, or Trp;<br>preferably wherein X at position 228 is Leu, Ile, or Val;<br>especially preferably wherein X at position 228 is Leu;<br>X at position 230 is Met, Ala, Val, Leu, Ile, Pro, Phe, or Trp;<br>preferably wherein X at position 230 is Leu, Ile, or Val;<br>especially preferably wherein X at position 230 is Ile; and<br>X at position 231 is Gly, Ala, Val, Leu, Ile, Pro, Phe, Met, or Trp;<br>preferably wherein X at position 231 is Leu, Ile, or Val; and<br>especially preferably wherein X at position 231 is Val,<br>wherein SEQ ID NO: 65 does not simultaneously comprise all of Ser at<br>position 228, Met at position 230, and Gly at position 231. |
| SEQ ID NO: 66<br>(4271 TCR2 β chain<br>predicted sequence<br>without N-terminal<br>signal peptide) | X at position 173 is Cys |
| SEQ ID NO: 71<br>(4271 TCR3 α chain<br>with N-terminal signal<br>peptide) | X at position 187 is Cys;<br>X at position 251 is Ser, Ala, Val, Leu, Ile, Pro, Phe, Met, or Trp;<br>preferably wherein X at position 251 is Leu, Ile, or Val;<br>especially preferably wherein X at position 251 is Leu;<br>X at position 253 is Met, Ala, Val, Leu, Ile, Pro, Phe, or Trp;<br>preferably wherein X at position 253 is Leu, Ile, or Val;<br>especially preferably wherein X at position 253 is Ile; and<br>X at position 254 is Gly, Ala, Val, Leu, Ile, Pro, Phe, Met, or Trp;<br>preferably wherein X at position 254 is Leu, Ile, or Val; and<br>especially preferably wherein X at position 254 is Val,<br>wherein SEQ ID NO: 71 does not simultaneously comprise all of Ser at<br>position 251, Met at position 253, and Gly at position 254. |
| SEQ ID NO: 72<br>(4271 TCR3 β chain<br>with N-terminal signal<br>peptide) | X at position 191 is Cys |
| SEQ ID NO: 73<br>(4271 TCR3 α chain<br>predicted sequence<br>without N-terminal<br>signal peptide) | X at position 168 is Cys;<br>X at position 232 is Ser, Ala, Val, Leu, Ile, Pro, Phe, Met, or Trp;<br>preferably wherein X at position 232 is Leu, Ile, or Val;<br>especially preferably wherein X at position 232 is Leu;<br>X at position 234 is Met, Ala, Val, Leu, Ile, Pro, Phe, or Trp;<br>preferably wherein X at position 234 is Leu, Ile, or Val;<br>especially preferably wherein X at position 234 is Ile; and<br>X at position 235 is Gly, Ala, Val, Leu, Ile, Pro, Phe, Met, or Trp;<br>preferably wherein X at position 235 is Leu, Ile, or Val; and<br>especially preferably wherein X at position 235 is Val,<br>wherein SEQ ID NO: 73 does not simultaneously comprise all of Ser at<br>position 232, Met at position 234, and Gly at position 235. |
| SEQ ID NO: 74<br>(4271 TCR3 β chain<br>predicted sequence<br>without N-terminal<br>signal peptide) | X at position 173 is Cys |

In an embodiment of the invention, the cysteine-substituted, LVL-modified TCR comprises (a) SEQ ID NO: 51 (α chain constant region of cysteine-substituted, LVL-modified TCR); (b) SEQ ID NO: 52 (β chain constant region of cysteine-substituted, LVL-modified TCR); or (c) both (a) and (b).

Also provided by the invention is a polypeptide comprising a functional portion of any of the TCRs described herein. The term "polypeptide," as used herein, includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to G12D RAS. The term "functional portion," when used in reference to a TCR, refers to any part or fragment of the TCR of the invention, which part or fragment retains the biological activity of the TCR of which it is a part (the parent TCR). Functional portions encompass, for example, those parts of a TCR that retain the ability to specifically bind to G12D RAS (e.g., within the context of any of the HLA Class II molecules described herein), or detect, treat, or prevent cancer, to a similar extent, the same extent, or to a higher extent, as the parent TCR. In reference to the parent TCR, the functional portion can comprise, for instance, about 10%, about 25%, about 30%, about 50%, about 70%, about 80%, about 90%, about 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to G12D RAS; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one or more of the CDR1, CDR2, and CDR3 of the variable region(s) of the α chain and/or β chain of a TCR of the invention. In an embodiment of the invention, the polypeptide can comprise the amino acid sequence of SEQ ID NO: 1 (CDR1 of α chain of 4271 TCR1), SEQ ID NO: 2 (CDR2 of α chain of 4271 TCR1), SEQ ID NO: 3 (CDR3 of α chain of 4271 TCR1), SEQ ID NO: 4 (CDR1 of β chain of 4271 TCR1), SEQ ID NO: 5 (CDR2 of β chain of 4271 TCR1), SEQ ID NO: 6 (CDR3 of β chain of 4271 TCR1), SEQ ID NO: 11 (CDR1 of α chain of 4271 TCR2), SEQ ID NO: 12 (CDR2 of α chain of 4271 TCR2), SEQ ID NO: 13 (CDR3 of α chain of 4271 TCR2), SEQ ID NO: 14 (CDR1 of β chain of 4271 TCR2), SEQ ID NO: 15 (CDR2 of chain of 4271 TCR2), SEQ ID NO: 16 (CDR3 of β chain of 4271 TCR2), SEQ ID NO: 21 (CDR1 of α chain of 4271 TCR3), SEQ ID NO: 22 (CDR2 of α chain of 4271 TCR3), SEQ ID NO: 23 (CDR3 of α chain of 4271 TCR3), SEQ ID NO: 24 (CDR1 of β chain of 4271 TCR3), SEQ ID NO: 25 (CDR2 of β chain of 4271 TCR3), SEQ ID NO: 26 (CDR3 of β chain of 4271 TCR3), SEQ ID NO: 31 (CDR1 of α chain of 4271 TCR4), SEQ ID NO: 32 (CDR2 of α chain of 4271 TCR4), SEQ ID NO: 33 (CDR3 of α chain of 4271 TCR4), SEQ ID NO: 34 (CDR1 of β chain of 4271 TCR4), SEQ ID NO: 35 (CDR2 of β chain of 4271 TCR4), SEQ ID NO: 36 (CDR3 of β chain of 4271 TCR4), or a combination thereof. In this regard, the inventive polypeptide can comprise any one or more of the amino acid sequences selected from the group consisting of SEQ ID NOs: 1-6, 11-16, 21-26, and 31-36. In an embodiment of the invention, the TCR comprises the amino acid sequences of: (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, or (l) all of SEQ ID NOs: 31-36. In a preferred embodiment, the polypeptide comprises the amino acid sequences of all of (i) SEQ ID NOs: 1-6, (ii) SEQ ID NOs: 11-16, (iii) SEQ ID NOs: 21-26, or (iv) SEQ ID NOs: 31-36.

In an embodiment of the invention, the inventive polypeptide can comprise, for instance, the variable region of the inventive TCR comprising a combination of the CDR regions set forth above. In this regard, the polypeptide can comprise the amino acid sequence of (i) SEQ ID NO: 7 (predicted sequence of variable region of α chain of 4271 TCR1 without N-terminal signal peptide); (ii) SEQ ID NO: 8 (predicted sequence of variable region of β chain of 4271 TCR1 without N-terminal signal peptide); (iii) SEQ ID NO: 9 (variable region of α chain of 4271 TCR1 with N-terminal signal peptide); (iv) SEQ ID NO: 10 (variable region of β chain of 4271 TCR1 with N-terminal signal peptide); (v) SEQ ID NO: 17 (predicted sequence of variable region of α chain of 4271 TCR2 without N-terminal signal peptide); (vi) SEQ ID NO: 18 (predicted sequence of variable region of β chain of 4271 TCR2 without N-terminal signal peptide); (vii) SEQ ID NO: 19 (variable region of α chain of 4271 TCR2 with N-terminal signal peptide); (viii) SEQ ID NO: 20 (variable region of β chain of 4271 TCR2 with N-terminal signal peptide); (ix) SEQ ID NO: 27 (predicted sequence of variable region of α chain of 4271 TCR3 without N-terminal signal peptide); (x) SEQ ID NO: 28 (predicted sequence of variable region of β chain of 4271 TCR3 without N-terminal signal peptide); (xi) SEQ ID NO: 29 (variable region of α chain of 4271 TCR3 with N-terminal signal peptide); (xii) SEQ ID NO: 30 (variable region of β chain of 4271 TCR3 with N-terminal signal peptide); (xiii) SEQ ID NO: 37 (predicted sequence of variable region of α chain of 4271 TCR4 without N-terminal signal peptide); (xiv) SEQ ID NO: 38 (predicted sequence of variable region of β chain of 4271 TCR4 without N-terminal signal peptide); (xv) SEQ ID NO: 39 (variable region of α chain of 4271 TCR4 with N-terminal signal peptide); (xvi) SEQ ID NO: 40 (variable region of β chain of 4271 TCR4 with N-terminal signal peptide); (xvii) both of SEQ ID NOs: 7 and 8; (xviii) both of SEQ ID NOs: 9 and 10; (xix) both of SEQ ID NOs: 17 and 18; (xx) both of SEQ ID NOs: 19 and 20; (xxi) both of SEQ ID NOs: 27 and 28; (xxii) both of SEQ ID NOs: 29 and 30; (xxiii) both of SEQ ID NOs: 37 and 38; or (xxiv) both of SEQ ID NOs: 39 and 40. Preferably, the polypeptide comprises the amino acid sequences of (i) both of SEQ ID NOs: 7 and 8, (ii) both of SEQ ID NOs: 9 and 10, (iii) both of SEQ ID NOs: 17 and 18, (iv) both of SEQ ID NOs: 19 and 20, (v) both of SEQ ID NOs: 27 and 28, (vi) both of SEQ ID NOs: 29 and 30, (vii) both of SEQ ID NOs: 37 and 38, or (viii) both of SEQ ID NOs: 39 and 40.

In an embodiment of the invention, the inventive polypeptide can further comprise the constant region of the inventive TCR set forth above. In this regard, the polypeptide can further comprise the amino acid sequence of SEQ ID NO: 53 (WT murine constant region of α chain), SEQ ID NO: 54 (WT murine constant region of β chain), SEQ ID NO: 49 (substituted murine constant region of α chain), SEQ ID NO: 50 (substituted murine constant region of β chain), SEQ ID NO: 51 (α chain constant region of cysteine-substituted, LVL-modified TCR); SEQ ID NO: 52 (β chain constant region of cysteine-substituted, LVL-modified TCR); both SEQ ID NOs: 49 and 50, both SEQ ID NOs: 51 and 52, or both SEQ ID NOs: 53 and 54. Preferably, the polypeptide further comprises the amino acid sequences of both of SEQ ID NOs: 49 and 50, both of SEQ ID NO: 51 and 52, or both of SEQ ID NOs: 53 and 54 in combination with any of the CDR regions or variable regions described herein with respect to other aspects of the invention. In an embodiment of the invention, one or both of SEQ ID NOs: 49 and 50 of the polypeptide are as defined in any one of Tables 2-4.

In an embodiment of the invention, the inventive polypeptide can comprise the entire length of an α or β chain of the TCR described herein. In this regard, the inventive polypeptide can comprise the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, or SEQ ID NO: 86. Alternatively, the polypeptide of the invention can comprise both chains of the TCRs described herein. For example, the polypeptide may comprise both of SEQ ID NOs: 55-56, both of SEQ ID NOs: 57-58, SEQ ID NOs: 59-60, both of SEQ ID NOs: 61-62, both of SEQ ID NOs: 63-64, both of SEQ ID NOs: 65-66, both of SEQ ID NOs: 67-68, both of SEQ ID NOs: 69-70, both of SEQ ID NOs: 71-72, both of SEQ ID NOs: 73-74, both of SEQ ID NOs: 75-76, both of SEQ ID NOs: 77-78, both of SEQ ID NOs: 79-80, both of SEQ ID NOs: 81-82, both of SEQ ID NOs: 83-84, or both of SEQ ID NOs: 85-86.

For example, the polypeptide of the invention can comprise (a) the amino acid sequence of SEQ ID NO: 55 (α chain of 4271 TCR1 with N-terminal signal peptide), wherein: (i) X at position 184 of SEQ ID NO: 55 is Thr or Cys: (ii) X at position 248 of SEQ ID NO: 55 is Ser, Ala, Val, Leu, Ile, Pro, Phe, Met, or Trp; (iii) X at position 250 of SEQ ID NO: 55 is Met, Ala, Val, Leu, Ile, Pro, Phe, or Trp; and (iv) X at position 251 of SEQ ID NO: 55 is Gly, Ala, Val, Leu, Ile, Pro, Phe, Met, or Trp; (b) the amino acid sequence of SEQ ID NO: 56 (β chain of 4271 TCR1 with N-terminal signal peptide), wherein X at position 199 of SEQ ID NO: 56 is Ser or Cys; (c) both of SEQ ID NOs: 55 and 56; (d) the amino acid sequence of SEQ ID NO: 57 (predicted sequence of α chain of 4271 TCR1 without N-terminal signal peptide), wherein: (i) X at position 165 of SEQ ID NO: 57 is Thr or Cys; (ii) X at position 229 of SEQ ID NO: 57 is Ser, Ala, Val, Leu, Ile, Pro, Phe, Met, or Trp; (iii) X at position 231 of SEQ ID NO: 57 is Met, Ala, Val, Leu, Ile, Pro, Phe, or Trp; and (iv) X at position 232 of SEQ ID NO: 57 is Gly, Ala, Val, Leu, Ile, Pro, Phe, Met, or Trp; (e) the amino acid sequence of SEQ ID NO: 58 (predicted sequence of β chain of 4271 TCR1 without N-terminal signal peptide), wherein X at position 175 of SEQ ID NO: 58 is Ser or Cys; (f) both of SEQ ID NOs: 57 and 58; (g) SEQ ID NO: 59 (α chain of cysteine-substituted, LVL-modified 4271 TCR1 with N-terminal signal sequence); (h) SEQ ID NO: 60 (β chain of cysteine-substituted, LVL-modified 4271 TCR1 with N-terminal signal sequence); (i) SEQ ID NO: 61 (predicted sequence of α chain of cysteine-substituted, LVL-modified 4271 TCR1 without N-terminal signal sequence); (j) SEQ ID NO: 62 (predicted sequence of β chain of cysteine-substituted, LVL-modified 4271 TCR1 without N-terminal signal sequence); (k) both of SEQ ID NOs: 59 and 60; (l) both of SEQ ID NOs: 61 and 62; (m) the amino acid sequence of SEQ ID NO: 63 (α chain of 4271 TCR2 with N-terminal signal peptide), wherein: (i) X at position 182 of SEQ ID NO: 63 is Thr or Cys: (ii) X at position 246 of SEQ ID NO: 63 is Ser, Ala, Val, Leu, Ile, Pro, Phe, Met, or Trp; (iii) X at position 248 of SEQ ID NO: 63 is Met, Ala, Val, Leu, Ile, Pro, Phe, or Trp; and (iv) X at position 249 of SEQ ID NO: 63 is Gly, Ala, Val, Leu, Ile, Pro, Phe, Met, or Trp; (n) the amino acid sequence of SEQ ID NO: 64 (β chain of 4271 TCR2 with N-terminal signal peptide), wherein X at position 197 of SEQ ID NO: 64 is Ser or Cys; (o) both of SEQ ID NOs: 63 and 64; (p) the amino acid sequence of SEQ ID NO: 65 (predicted sequence of α chain of 4271 TCR2 without N-terminal signal peptide), wherein: (i) X at position 164 of SEQ ID NO: 65 is Thr or Cys: (ii) X at position 228 of SEQ ID NO: 65 is Ser, Ala, Val, Leu, Ile, Pro, Phe, Met, or Trp: (iii) X at position 230 of SEQ ID NO: 65 is Met, Ala, Val, Leu, Ile, Pro, Phe, or Trp; and (iv) X at position 231 of SEQ ID NO: 65 is Gly, Ala, Val, Leu, Ile, Pro, Phe, Met, or Trp; (q) the amino acid sequence of SEQ ID NO: 66 (predicted sequence of β chain of 4271 TCR2 without N-terminal signal peptide), wherein X at position 173 of SEQ ID NO: 66 is Ser or Cys; (r) both of SEQ ID NOs: 65 and 66; (s) SEQ ID NO: 67 (α chain of cysteine-substituted, LVL-modified 4271 TCR2 with N-terminal signal sequence); (t) SEQ ID NO: 68 (β chain of cysteine-substituted, LVL-modified 4271 TCR2 with N-terminal signal sequence); (u) SEQ ID NO: 69 (predicted sequence of α chain of cysteine-substituted, LVL-modified 4271 TCR2 without N-terminal signal sequence); (v) SEQ ID NO: 70 (predicted sequence of β chain of cysteine-substituted, LVL-modified 4271 TCR2 without N-terminal signal sequence); (w) both of SEQ ID NOs: 67 and 68; (x) both of SEQ ID NOs: 69 and 70; (y) the amino acid sequence of SEQ ID NO:

71 (α chain of 4271 TCR3 with N-terminal signal peptide), wherein: (i) X at position 187 of SEQ ID NO: 71 is Thr or Cys: (ii) X at position 251 of SEQ ID NO: 71 is Ser, Ala, Val, Leu, Ile, Pro, Phe, Met, or Trp: (iii) X at position 253 of SEQ ID NO: 71 is Met, Ala, Val, Leu, Ile, Pro, Phe, or Trp; and (iv) X at position 254 of SEQ ID NO: 71 is Gly, Ala, Val, Leu, Ile, Pro, Phe, Met, or Trp; (z) the amino acid sequence of SEQ ID NO: 72 (β chain of 4271 TCR3 with N-terminal signal peptide), wherein X at position 191 of SEQ ID NO: 72 is Ser or Cys; (aa) both of SEQ ID NOs: 71 and 72; (bb) the amino acid sequence of SEQ ID NO: 73 (predicted sequence of α chain of 4271 TCR3 without N-terminal signal peptide), wherein: (i) X at position 168 of SEQ ID NO: 73 is Thr or Cys: (ii) X at position 232 of SEQ ID NO: 73 is Ser, Ala, Val, Leu, Ile, Pro, Phe, Met, or Trp: (iii) X at position 234 of SEQ ID NO: 73 is Met, Ala, Val, Leu, Ile, Pro, Phe, or Trp; and (iv) X at position 235 of SEQ ID NO: 73 is Gly, Ala, Val, Leu, Ile, Pro, Phe, Met, or Trp; (cc) the amino acid sequence of SEQ ID NO: 74 (predicted sequence of β chain of 4271 TCR3 without N-terminal signal peptide), wherein X at position 173 of SEQ ID NO: 74 is Ser or Cys; (dd) both of SEQ ID NOs: 73 and 74; (ee) SEQ ID NO: 75 (α chain of cysteine-substituted, LVL-modified 4271 TCR3 with N-terminal signal sequence); (ff) SEQ ID NO: 76 (β chain of cysteine-substituted, LVL-modified 4271 TCR3 with N-terminal signal sequence); (gg) SEQ ID NO: 77 (predicted sequence of α chain of cysteine-substituted, LVL-modified 4271 TCR3 without N-terminal signal sequence); (hh) SEQ ID NO: 78 (predicted sequence of β chain of cysteine-substituted, LVL-modified 4271 TCR3 without N-terminal signal sequence); (ii) both of SEQ ID NOs: 75 and 76; (jj) both of SEQ ID NOs: 77 and 78; (kk) the amino acid sequence of SEQ ID NO: 79 (α chain of 4271 TCR4 with N-terminal signal peptide), wherein: (i) X at position 175 of SEQ ID NO: 79 is Thr or Cys: (ii) X at position 239 of SEQ ID NO: 79 is Ser, Ala, Val, Leu, Ile, Pro, Phe, Met, or Trp: (iii) X at position 241 of SEQ ID NO: 79 is Met, Ala, Val, Leu, Ile, Pro, Phe, or Trp; and (iv) X at position 242 of SEQ ID NO: 79 is Gly, Ala, Val, Leu, Ile, Pro, Phe, Met, or Trp; (ll) the amino acid sequence of SEQ ID NO: 80 (β chain of 4271 TCR4 with N-terminal signal peptide), wherein X at position 190 of SEQ ID NO: 80 is Ser or Cys; (mm) both of SEQ ID NOs: 79 and 80; (nn) the amino acid sequence of SEQ ID NO: 81 (predicted sequence of α chain of 4271 TCR4 without N-terminal signal peptide), wherein: (i) X at position 159 of SEQ ID NO: 81 is Thr or Cys: (ii) X at position 223 of SEQ ID NO: 81 is Ser, Ala, Val, Leu, Ile, Pro, Phe, Met, or Trp: (iii) X at position 225 of SEQ ID NO: 81 is Met, Ala, Val, Leu, Ile, Pro, Phe, or Trp; and (iv) X at position 226 of SEQ ID NO: 81 is Gly, Ala, Val, Leu, Ile, Pro, Phe, Met, or Trp; (oo) the amino acid sequence of SEQ ID NO: 82 (predicted sequence of β chain of 4271 TCR4 without N-terminal signal peptide), wherein X at position 172 of SEQ ID NO: 82 is Ser or Cys; (pp) both of SEQ ID NOs: 81 and 82; (qq) SEQ ID NO: 83 (α chain of cysteine-substituted, LVL-modified 4271 TCR4 with N-terminal signal sequence); (rr) SEQ ID NO: 84 (P chain of cysteine-substituted, LVL-modified 4271 TCR4 with N-terminal signal sequence); (ss) SEQ ID NO: 85 (predicted sequence of α chain of cysteine-substituted, LVL-modified 4271 TCR4 without N-terminal signal sequence); (tt) SEQ ID NO: 86 (predicted sequence of β chain of cysteine-substituted, LVL-modified 4271 TCR4 without N-terminal signal sequence); (uu) both of SEQ ID NOs: 83 and 84; or (vv) both of SEQ ID NOs: 85 and 86. In an embodiment of the invention, any one or more of SEQ ID NOs: 55-58, 63-66, 71-74, and 79-82 of the polypeptide are as defined in any one of Tables 2-4.

The invention further provides a protein comprising at least one of the polypeptides described herein. By "protein" is meant a molecule comprising one or more polypeptide chains.

In an embodiment, the protein of the invention can comprise (a) a first polypeptide chain comprising the amino acid sequences of SEQ ID NOs: 1-3 and a second polypeptide chain comprising the amino acid sequences of SEQ ID NOs: 4-6; (b) a first polypeptide chain comprising the amino acid sequences of SEQ ID NOs: 11-13 and a second polypeptide chain comprising the amino acid sequences of SEQ ID NOs: 14-16; (c) a first polypeptide chain comprising the amino acid sequences of SEQ ID NOs: 21-23 and a second polypeptide chain comprising the amino acid sequences of SEQ ID NOs: 24-26; or (d) a first polypeptide chain comprising the amino acid sequences of SEQ ID NOs: 31-33 and a second polypeptide chain comprising the amino acid sequences of SEQ ID NOs: 34-36.

In another embodiment of the invention, (i) the first polypeptide chain comprises the amino acid sequence of SEQ ID NO: 7 and the second polypeptide chain comprises the amino acid sequence of SEQ ID NO: 8; (ii) the first polypeptide chain comprises the amino acid sequence of SEQ ID NO: 9 and the second polypeptide chain comprises the amino acid sequence of SEQ ID NO: 10; (iii) the first polypeptide chain comprises the amino acid sequence of SEQ ID NO: 17 and the second polypeptide chain comprises the amino acid sequence of SEQ ID NO: 18; (iv) the first polypeptide chain comprises the amino acid sequence of SEQ ID NO: 19 and the second polypeptide chain comprises the amino acid sequence of SEQ ID NO: 20; (v) the first polypeptide chain comprises the amino acid sequence of SEQ ID NO: 27 and the second polypeptide chain comprises the amino acid sequence of SEQ ID NO: 28; (vi) the first polypeptide chain comprises the amino acid sequence of SEQ ID NO: 29 and the second polypeptide chain comprises the amino acid sequence of SEQ ID NO: 30; (vii) the first polypeptide chain comprises the amino acid sequence of SEQ ID NO: 37 and the second polypeptide chain comprises the amino acid sequence of SEQ ID NO: 38; or (viii) the first polypeptide chain comprises the amino acid sequence of SEQ ID NO: 39 and the second polypeptide chain comprises the amino acid sequence of SEQ ID NO: 40.

The inventive protein may further comprise any of the constant regions described herein with respect to other aspects of the invention. In this regard, in an embodiment of the invention, (i) the first polypeptide chain may further comprise the amino acid sequence of SEQ ID NO: 49 and the second polypeptide chain may further comprise the amino acid sequence of SEQ ID NO: 50; (ii) the first polypeptide chain may further comprise the amino acid sequence of SEQ ID NO: 51 and the second polypeptide chain may further comprise the amino acid sequence of SEQ ID NO: 52; or (ii) the first polypeptide chain may comprise the amino acid sequence of SEQ ID NO: 53 and the second polypeptide chain may comprise the amino acid sequence of SEQ ID NO: 54. In an embodiment of the invention, one or both of SEQ ID NOs: 49 and 50 of the protein are as defined in any one of Tables 2-4.

The inventive protein may comprise a full length α or β chain, as described herein with respect to other aspects of the invention. In this regard, in an embodiment of the invention, (a) the first polypeptide chain comprises the amino acid sequence of SEQ ID NO: 55, wherein: (i) X at position 184 of SEQ ID NO: 55 is Thr or Cys; (ii) X at position 248 of SEQ ID NO: 55 is Ser, Ala, Val, Leu, Ile, Pro, Phe, Met, or Trp; (iii) X at position 250 of SEQ ID NO: 55 is Met, Ala, Val, Leu, Ile, Pro, Phe, or Trp; and (iv) X at position 251 of SEQ ID NO: 55 is Gly, Ala, Val, Leu, Ile, Pro, Phe, Met, or Trp; (b) the second polypeptide chain comprises the amino acid sequence of SEQ ID NO: 56, wherein X at position 199 of SEQ ID NO: 56 is Ser or Cys; (c) the first polypeptide chain comprises the amino acid sequence of SEQ ID NO: 55 and the second polypeptide chain comprises the amino acid sequence of 56; (d) the first polypeptide chain comprises the amino acid sequence of SEQ ID NO: 57, wherein: (i) X at position 165 of SEQ ID NO: 57 is Thr or Cys; (ii) X at position 229 of SEQ ID NO: 57 is Ser, Ala, Val, Leu, Ile, Pro, Phe, Met, or Trp; (iii) X at position 231 of SEQ ID NO: 57 is Met, Ala, Val, Leu, Ile, Pro, Phe, or Trp; and (iv) X at position 232 of SEQ ID NO: 57 is Gly, Ala, Val, Leu, Ile, Pro, Phe, Met, or Trp; (e) the second polypeptide chain comprises the amino acid sequence of SEQ ID NO: 58, wherein X at position 175 of SEQ ID NO: 58 is Ser or Cys; (f) the first polypeptide chain comprises the amino acid sequence of SEQ ID NO: 57 and the second polypeptide chain comprises the amino acid sequence of 58; (g) the first polypeptide chain comprises the amino acid sequence of SEQ ID NO: 59; (h) the second polypeptide chain comprises the amino acid sequence of SEQ ID NO: 60; (i) the first polypeptide chain comprises the amino acid sequence of SEQ ID NO: 61; (j) the second polypeptide chain comprises the amino acid sequence of SEQ ID NO: 62; (k) the first polypeptide chain comprises the amino acid sequence of SEQ ID NO: 59 and the second polypeptide chain comprises the amino acid sequence of 60; (l) the first polypeptide chain comprises the amino acid sequence of SEQ ID NO: 61 and the second polypeptide chain comprises the amino acid sequence of 62; (m) the first polypeptide chain comprises the amino acid sequence of SEQ ID NO: 63, wherein: (i) X at position 182 of SEQ ID NO: 63 is Thr or Cys; (ii) X at position 246 of SEQ ID NO: 63 is Ser, Ala, Val, Leu, Ile, Pro, Phe, Met, or Trp; (iii) X at position 248 of SEQ ID NO: 63 is Met, Ala, Val, Leu, Ile, Pro, Phe, or Trp; and (iv) X at position 249 of SEQ ID NO: 63 is Gly, Ala, Val, Leu, Ile, Pro, Phe, Met, or Trp; (n) the second polypeptide chain comprises the amino acid sequence of SEQ ID NO: 64, wherein X at position 197 of SEQ ID NO: 64 is Ser or Cys; (o) the first polypeptide chain comprises the amino acid sequence of SEQ ID NO: 63 and the second polypeptide chain comprises the amino acid sequence of 64; (p) the first polypeptide chain comprises the amino acid sequence of SEQ ID NO: 65, wherein: (i) X at position 164 of SEQ ID NO: 65 is Thr or Cys; (ii) X at position 228 of SEQ ID NO: 65 is Ser, Ala, Val, Leu, Ile, Pro, Phe, Met, or Trp; (iii) X at position 230 of SEQ ID NO: 65 is Met, Ala, Val, Leu, Ile, Pro, Phe, or Trp; and (iv) X at position 231 of SEQ ID NO: 65 is Gly, Ala, Val, Leu, Ile, Pro, Phe, Met, or Trp; (q) the second polypeptide chain comprises the amino acid sequence of SEQ ID NO: 66, wherein X at position 173 of SEQ ID NO: 66 is Ser or Cys; (r) the first polypeptide chain comprises the amino acid sequence of SEQ ID NO: 65 and the second polypeptide chain comprises the amino acid sequence of 66; (s) the first polypeptide chain comprises the amino acid sequence of SEQ ID NO: 67; (t) the second polypeptide chain comprises the amino acid sequence of SEQ ID NO: 68; (u) the first polypeptide chain comprises the amino acid sequence of SEQ ID NO: 69; (v) the second polypeptide chain comprises the amino acid sequence of SEQ ID NO: 70; (w) the first polypeptide chain comprises the amino acid sequence of SEQ ID NO: 67 and the second polypeptide chain comprises the amino acid sequence of 68; (x) the first polypeptide chain comprises the amino acid sequence of SEQ ID NO: 69 and the second polypeptide chain comprises the amino acid sequence of 70; (y) the first polypeptide chain comprises the amino acid sequence of SEQ ID NO: 71, wherein: (i) X at position 187 of SEQ ID NO: 71 is Thr or Cys; (ii) X at position 251 of SEQ ID NO: 71 is Ser, Ala, Val, Leu, Ile, Pro, Phe, Met, or Trp; (iii) X at position 253 of SEQ ID NO: 71 is Met, Ala, Val, Leu, Ile, Pro, Phe, or Trp; and (iv) X at position 254 of SEQ ID NO: 71 is Gly, Ala, Val, Leu, Ile, Pro, Phe, Met, or Trp; (z) the second polypeptide chain comprises the amino acid sequence of SEQ ID NO: 72, wherein X at position 191 of SEQ ID NO: 72 is Ser or Cys; (aa) the first polypeptide chain comprises the amino acid sequence of SEQ ID NO: 71 and the second polypeptide chain comprises the amino acid sequence of 72; (bb) the first polypeptide chain comprises the amino acid sequence of SEQ ID NO: 73, wherein: (i) X at position 168 of SEQ ID NO: 73 is Thr or Cys; (ii) X at position 232 of SEQ ID NO: 73 is Ser, Ala, Val, Leu, Ile, Pro, Phe, Met, or Trp; (iii) X at position 234 of SEQ ID NO: 73 is Met, Ala, Val, Leu, Ile, Pro, Phe, or Trp; and (iv) X at position 235 of SEQ ID NO: 73 is Gly, Ala, Val, Leu, Ile, Pro, Phe, Met, or Trp; (cc) the second polypeptide chain comprises the amino acid sequence of SEQ ID NO: 74, wherein X at position 173 of SEQ ID NO: 74 is Ser or Cys; (dd) the first polypeptide chain comprises the amino acid sequence of SEQ ID NO: 73 and the second polypeptide chain comprises the amino acid sequence of 74; (ee) the first polypeptide chain comprises the amino acid sequence of SEQ ID NO: 75; (ff) the second polypeptide chain comprises the amino acid sequence of SEQ ID NO: 76; (gg) the first polypeptide chain comprises the amino acid sequence of SEQ ID NO: 77; (hh) the second polypeptide chain comprises the amino acid sequence of SEQ ID NO: 78; (ii) the first polypeptide chain comprises the amino acid sequence of SEQ ID NO: 75 and the second polypeptide chain comprises the amino acid sequence of 76; (jj) the first polypeptide chain comprises the amino acid sequence of SEQ ID NO: 77 and the second polypeptide chain comprises the amino acid sequence of 78; (kk) the first polypeptide chain comprises the amino acid sequence of SEQ ID NO: 79, wherein: (i) X at position 175 of SEQ ID NO: 79 is Thr or Cys; (ii) X at position 239 of SEQ ID NO: 79 is Ser, Ala, Val, Leu, Ile, Pro, Phe, Met, or Trp; (iii) X at position 241 of SEQ ID NO: 79 is Met, Ala, Val, Leu, Ile, Pro, Phe, or Trp; and (iv) X at position 242 of SEQ ID NO: 79 is Gly, Ala, Val, Leu, Ile, Pro, Phe, Met, or Trp; (ll) the second polypeptide chain comprises the amino acid sequence of SEQ ID NO: 80, wherein X at position 190 of SEQ ID NO: 80 is Ser or Cys; (mm) the first polypeptide chain comprises the amino acid sequence of SEQ ID NO: 79 and the second polypeptide chain comprises the amino acid sequence of 80; (nn) the first polypeptide chain comprises the amino acid sequence of SEQ ID NO: 81, wherein: (i) X at position 159 of SEQ ID NO: 81 is Thr or Cys; (ii) X at position 223 of SEQ ID NO: 81 is Ser, Ala, Val, Leu, Ile, Pro, Phe, Met, or Trp; (iii) X at position 225 of SEQ ID NO: 81 is Met, Ala, Val, Leu, Ile, Pro, Phe, or Trp; and (iv) X at position 226 of SEQ ID NO: 81 is Gly, Ala, Val, Leu, Ile, Pro, Phe, Met, or Trp; (oo) the second polypeptide chain comprises the amino acid sequence of SEQ ID NO: 82, wherein X at position 172 of SEQ ID NO: 82 is Ser or Cys; (pp) the first polypeptide chain comprises the amino acid sequence of SEQ ID NO: 81 and the second polypeptide chain comprises the amino acid sequence of 82; (qq) the first polypeptide chain comprises the amino acid sequence of SEQ ID NO: 83; (rr) the second polypeptide chain comprises the amino acid sequence of SEQ ID NO: 84; (ss) the first polypeptide chain comprises the amino acid sequence of SEQ ID NO: 85; (tt) the second polypeptide chain comprises the amino acid sequence of SEQ ID NO: 86; (uu) the first polypeptide chain comprises the amino acid sequence of SEQ ID NO: 83 and the second polypeptide chain comprises the amino acid sequence of 84; or (vv) the first polypeptide chain comprises the amino acid sequence of SEQ ID NO: 85 and the second polypeptide chain comprises the amino acid sequence of 86. In an embodiment of the invention, one or more of SEQ ID NOs: 55-58, 63-66, 71-74, and 79-82 are as defined in any one of Tables 2-4.

The protein of the invention can be a TCR. Alternatively, if, for example, the protein comprises a single polypeptide chain comprising the amino acid sequences of both the TCR α and β chains, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods.

In some embodiments of the invention, the TCRs, polypeptides, and proteins of the invention may be expressed as a single protein comprising a linker peptide linking the α chain and the β chain. In this regard, the TCRs, polypeptides, and proteins of the invention may further comprise a linker peptide. The linker peptide may advantageously facilitate the expression of a recombinant TCR, polypeptide, and/or protein in a host cell. The linker peptide may comprise any suitable amino acid sequence. The linker peptide may be a cleavable linker peptide. For example, the linker peptide may be a furin-SGSG (SEQ ID NO: 99)-P2A linker peptide comprising the amino acid sequence of RAKRSGS-GATNFSLLKQAGDVEENPGP (SEQ ID NO: 87). Upon expression of the construct including the linker peptide by a host cell, the linker peptide may be cleaved, resulting in separated α and β chains. In an embodiment of the invention, the TCR, polypeptide, or protein may comprise an amino acid sequence comprising a full-length α chain, a full-length β chain, and a linker peptide positioned between the α and β chains.

The protein of the invention can be a recombinant antibody, or an antigen binding portion thereof, comprising at least one of the inventive polypeptides described herein. As used herein, "recombinant antibody" refers to a recombinant (e.g., genetically engineered) protein comprising at least one of the polypeptides of the invention and a polypeptide chain of an antibody, or an antigen binding portion thereof. The polypeptide of an antibody, or antigen binding portion thereof, can be a heavy chain, a light chain, a variable or constant region of a heavy or light chain, a single chain variable fragment (scFv), or an Fe, Fab, or F(ab)₂' fragment of an antibody, etc. The polypeptide chain of an antibody, or an antigen binding portion thereof, can exist as a separate polypeptide of the recombinant antibody. Alternatively, the polypeptide chain of an antibody, or an antigen binding portion thereof, can exist as a polypeptide, which is expressed in frame (in tandem) with the polypeptide of the invention. The polypeptide of an antibody, or an antigen binding portion thereof, can be a polypeptide of any antibody or any antibody fragment, including any of the antibodies and antibody fragments described herein.

Included in the scope of the invention are functional variants of the inventive TCRs, polypeptides, or proteins described herein. The term "functional variant," as used herein, refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to the G12D RAS for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, about 50%, about 75%, about 80%, about 90%, about 95%, about 96%, about 97%, about 98%, about 99% or more identical in amino acid sequence to the parent TCR, polypeptide, or protein, respectively.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the TCR, polypeptide, or protein, e.g., other amino acids, do not materially change the biological activity of the TCR, polypeptide, or protein. In this regard, the inventive TCR, polypeptide, or protein can, for example, consist essentially of the amino acid sequence of SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, both of SEQ ID NOs: 55 and 56, both of SEQ ID NOs: 57 and 58, SEQ ID NOs: 59 and 60, both of SEQ ID NOs: 61 and 62, both of SEQ ID NOs: 63 and 64, both of SEQ ID NOs: 65 and 66, both of SEQ ID NOs: 67 and 68, both of SEQ ID NOs: 69 and 70, both of SEQ ID NOs: 71 and 72, both of SEQ ID NOs: 73 and 74, both of SEQ ID NOs: 75 and 76, both of SEQ ID NOs: 77 and 78, both of SEQ ID NOs: 79 and 80, both of SEQ ID NOs: 81 and 82, both of SEQ ID NOs: 83 and 84, or both of SEQ ID NOs: 85 and 86. Also, for instance, the inventive TCRs, polypeptides, or proteins can consist essentially of the amino acid sequence(s) of (i) SEQ ID NO: 7, (ii) SEQ ID NO: 8, (iii) SEQ ID NO: 9, (iv) SEQ ID NO: 10, (v) SEQ ID NO: 17, (vi) SEQ ID NO: 18, (vii) SEQ ID NO: 19, (viii) SEQ ID NO: 20, (ix) SEQ ID NO: 27, (x) SEQ ID NO: 28, (xi) SEQ ID NO: 29, (xii) SEQ ID NO: 30, (xiii) SEQ ID NO: 37, (xiv) SEQ ID NO: 38, (xv) SEQ ID NO: 39, (xvi) SEQ ID NO: 40, (xvii) both of SEQ ID NOs: 7 and 8, (xviii) both of SEQ ID NOs: 9 and 10, (xix) both of SEQ ID NOs: 17 and 18, (xx) both of SEQ ID NOs: 19 and 20, (xxi) both of SEQ ID NOs: 27 and 28, (xxii) both of SEQ ID NOs: 29 and 30, (xxiii) both of SEQ ID NOs: 37 and 38, or (xxiv) both of SEQ ID NOs: 39 and 40. Furthermore, the inventive TCRs, polypeptides, or proteins can consist essentially of the amino acid sequences of (a) all of SEQ ID NOs: 1-3, (b) all of SEQ ID NOs: 4-6, (c) all of SEQ ID NOs: 1-6, (d) all of SEQ ID NOs: 11-13, (e) all of SEQ ID NOs: 14-16, (f) all of SEQ ID NOs: 11-16, (g) all of SEQ ID NOs: 21-23, (h) all of SEQ ID NOs: 24-26, (i) all of SEQ ID NOs: 21-26, (j) all of SEQ ID NOs: 31-33, (k) all of SEQ ID NOs: 34-36, or (l) all of SEQ ID NOs: 31-36.

The TCRs, polypeptides, and proteins of the invention can be of any length, i.e., can comprise any number of amino acids, provided that the TCRs, polypeptides, or proteins retain their biological activity, e.g., the ability to specifically bind to G12D RAS; detect cancer in a mammal; or treat or prevent cancer in a mammal, etc. For example, the polypeptide can be in the range of from about 50 to about 5000 amino acids long, such as about 50, about 70, about 75, about 100, about 125, about 150, about 175, about 200, about 300, about 400, about 500, about 600, about 700, about 800, about 900, about 1000 or more amino acids in length. In this regard, the polypeptides of the invention also include oligopeptides.

The TCRs, polypeptides, and proteins of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, s-phenylserine s-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual,* 4*th* ed., Cold Spring Harbor Press, Cold Spring Harbor, NY (2012). Alternatively, the TCRs, polypeptides, and/or proteins described herein can be synthesized by any of a variety of commercial entities. In this respect, the inventive TCRs, polypeptides, and proteins can be synthetic, recombinant, isolated, and/or purified. An embodiment of the invention provides an isolated or purified TCR, polypeptide, or protein encoded by any of the nucleic acids or vectors described herein with respect to other aspects of the invention. Another embodiment of the invention provides an isolated or purified TCR, polypeptide, or protein that results from expression of any of the nucleic acids or vectors described herein with respect to other aspects of the invention in a cell. Still another embodiment of the invention provides a method of producing any of the TCRs, polypeptides, or proteins described herein, the method comprising culturing any of the host cells or populations of host cells described herein so that the TCR, polypeptide, or protein is produced.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art.

An embodiment of the invention provides a nucleic acid comprising a nucleotide sequence encoding any of the TCRs, polypeptides, or proteins described herein. "Nucleic acid," as used herein, includes "polynucleotide," "oligonucleotide," and "nucleic acid molecule," and generally means a polymer of DNA or RNA, which can be single-stranded or double-stranded, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

In an embodiment of the invention, the nucleic acid comprises the nucleotide sequence of SEQ ID NO: 95 (encodes both α and β chain of 4271 TCR1 separated by cleavable linker peptide), SEQ ID NO: 96 (encodes both α and β chain of 4271 TCR2 separated by cleavable linker peptide), SEQ ID NO: 97 (encodes both α and β chain of 4271 TCR3 separated by cleavable linker peptide), or SEQ ID NO: 98 (encodes both α and β chain of 4271 TCR4 separated by cleavable linker peptide).

The nucleic acids can be constructed based on chemical synthesis and/or enzymatic ligation reactions using procedures known in the art. See, for example, Green and Sambrook et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, β-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, β-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from any of a variety of commercial entities.

The nucleic acid can comprise any nucleotide sequence which encodes any of the TCRs, polypeptides, or proteins described herein. In an embodiment of the invention, the nucleic acid comprises a codon-optimized nucleotide sequence encoding any of the TCRs, polypeptides, or proteins described herein. Without being bound to any particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

An embodiment of the invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. In this regard, the nucleic acid may consist essentially of any of the nucleotide sequences described herein.

An embodiment of the invention provides an isolated or purified nucleic acid comprising, from 5' to 3', a first nucleic acid sequence and a second nucleotide sequence, wherein the first and second nucleotide sequence, respectively, encode the amino sequences of SEQ ID NOs: 7 and 8; 8 and 7; 9 and 10; 10 and 9; 17 and 18; 18 and 17; 19 and 20; 20 and 19; 27 and 28; 28 and 27; 29 and 30; 30 and 29; 37 and 38; 38 and 37; 39 and 40; 40 and 39; 55 and 56; 56 and 55; 57 and 58; 58 and 57; 59 and 60; 60 and 59; 61 and 62; 62 and 61; 63 and 64; 64 and 63; 65 and 66; 66 and 65; 67 and 68; 68 and 67; 69 and 70; 70 and 69; 71 and 72; 72 and 71; 73 and 74; 74 and 73; 75 and 76; 76 and 75; 77 and 78; 78 and 77; 79 and 80; 80 and 79; 81 and 82; 82 and 81; 83 and 84; 84 and 83; 85 and 86; or 86 and 85.

In an embodiment of the invention, the isolated or purified nucleic acid further comprises a third nucleotide sequence interposed between the first and second nucleotide sequence, wherein the third nucleotide sequence encodes a cleavable linker peptide. In an embodiment of the invention, the cleavable linker peptide comprises the amino acid sequence of RAKRSGSGATNFSLLKQAGDVEENPGP (SEQ ID NO: 87).

The nucleic acids of the invention can be incorporated into a recombinant expression vector. In this regard, the invention provides a recombinant expression vector comprising any of the nucleic acids of the invention. In an embodiment of the invention, the recombinant expression vector comprises a nucleotide sequence encoding the α chain, the β chain, and linker peptide.

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotide, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector. In an embodiment of the invention, the recombinant expression vector is a transposon or a lentiviral vector.

The recombinant expression vectors of the invention can be prepared using standard recombinant DNA techniques described in, for example, Green and Sambrook et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein, or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan.

Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, nitroreductase, and the inducible caspase 9 gene system.

Another embodiment of the invention further provides a host cell comprising any of the nucleic acids or recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell. In an embodiment of the invention, the host cell is a human lymphocyte. In another embodiment of the invention, the host cell is selected from the group consisting of a T cell, a natural killer T (NKT) cell, an invariant natural killer T (iNKT) cell, and a natural killer (NK) cell. Still another embodiment of the invention provides a method of producing a host cell expressing a TCR that has antigenic specificity for the peptide of MTEYKLVVVGADGVGK-SALTIQLI (SEQ ID NO: 88), the method comprising contacting a cell with any of the vectors described herein under conditions that allow introduction of the vector into the cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD4$^+$ T cells, CD8$^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.,* 26:332-42 (2003); and Riddell et al., *J. Immunol. Methods,* 128:189-201 (1990). In an embodiment, expansion of the numbers of T cells is carried out by culturing the T cells with OKT3 antibody, IL-2, and feeder PBMC (e.g., irradiated allogeneic PBMC).

The inventive TCRs, polypeptides, proteins, nucleic acids, recombinant expression vectors, and host cells (including populations thereof), can be isolated and/or purified. The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70%, about 80%, about 90%, about 95%, or can be about 100%.

The inventive TCRs, polypeptides, proteins, nucleic acids, recombinant expression vectors, and host cells (including populations thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, nucleic acids, expression vectors, and host cells (including populations thereof), described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Methods for preparing administrable compositions are known or apparent to those skilled in the art and are described in more detail in, for example, *Remington: The Science and Practice of Pharmacy*, 22$^{nd}$ Ed., Pharmaceutical Press (2012). It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell (or population thereof) expressing the inventive TCR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen (e.g., G12D RAS), or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-7γ is secreted by T cells expressing the inventive TCR, polypeptide, or protein upon administration of a given dose of such T cells to a mammal among a set of mammals of which each is given a different dose of the T cells, could be used to determine a starting dose to be administered to a mammal. The extent to which target cells are lysed or IFN-7γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the cancer being treated. In an embodiment in which the inventive TCR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a chemotherapeutic agent. The practice of conjugating compounds to a chemotherapeutic agent is known in the art. One of ordinary skill in the art recognizes that sites on the inventive TCR materials, which are not necessary for the function of the inventive TCR materials, are suitable sites for attaching a bridge and/or a chemotherapeutic agent, provided that the bridge and/or chemotherapeutic agent, once attached to the inventive TCR materials, do(es) not interfere with the function of the inventive TCR materials, i.e., the ability to bind to G12D RAS or to detect, treat, or prevent cancer.

It is contemplated that the inventive pharmaceutical compositions, TCRs, polypeptides, proteins, nucleic acids, recombinant expression vectors, host cells, and populations of cells can be used in methods of treating or preventing cancer. Without being bound to a particular theory, the inventive TCRs are believed to bind specifically to G12D RAS, such that the TCR (or related inventive polypeptide or protein), when expressed by a cell, is able to mediate an immune response against a target cell expressing G12D RAS. In this regard, an embodiment of the invention provides a method of treating or preventing cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the mammal.

An embodiment of the invention provides a method of inducing an immune response against a cancer in a mammal, comprising administering to the mammal any of the pharmaceutical compositions, TCRs, polypeptides, or proteins described herein, any nucleic acid or recombinant expression vector comprising a nucleotide sequence encoding any of the TCRs, polypeptides, or proteins described herein, or any host cell or population of cells comprising a recombinant vector which encodes any of the TCRs, polypeptides, or proteins described herein, in an amount effective to induce an immune response against the cancer in the mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, for use in the treatment or prevention of cancer in a mammal.

An embodiment of the invention provides any of the pharmaceutical compositions, TCRs, polypeptides, or proteins described herein, any nucleic acid or recombinant expression vector comprising a nucleotide sequence encoding any of the TCRs, polypeptides, or proteins described herein, or any host cell or population of cells comprising a recombinant vector which encodes any of the TCRs, polypeptides, or proteins described herein, for use in inducing an immune response against a cancer in a mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof. Alternatively or additionally, "prevention" may encompass preventing or delaying the recurrence of cancer, or a symptom or condition thereof.

Also provided is a method of detecting the presence of cancer in a mammal. The method comprises (i) contacting a sample comprising one or more cells from the mammal with any of the inventive TCRs, polypeptides, proteins, nucleic acids, recombinant expression vectors, host cells, populations of cells, or pharmaceutical compositions described herein, thereby forming a complex, and (ii) detecting the complex, wherein detection of the complex is indicative of the presence of cancer in the mammal.

With respect to the inventive method of detecting cancer in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive method of detecting cancer, the contacting can take place in vitro or in vivo with respect to the mammal. Preferably, the contacting is in vitro.

Also, detection of the complex can occur through any number of ways known in the art. For instance, the inventive TCRs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, colorectal cancer, endometrial cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is pancreatic, colorectal, lung, endometrial, ovarian, or prostate cancer. Preferably, the lung cancer is lung adenocarcinoma, the ovarian cancer is epithelial ovarian cancer, and the pancreatic cancer is pancreatic adenocarcinoma. In an embodiment of the invention, the cancer expresses a mutated human RAS amino acid sequence with a substitution of glycine at position 12 with aspartic acid, wherein the mutated human RAS amino acid sequence is a mutated human KRAS, a mutated human HRAS, or a mutated human NRAS amino acid sequence, and wherein position 12 is defined by reference to the WT human KRAS, WT human HRAS, or WT human NRAS protein, respectively. The mutated human KRAS, mutated human HRAS, and mutated human NRAS expressed by the cancer may be as described herein with respect to other aspects of the invention.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLE 1

This example demonstrates the isolation of an anti-G12D RAS TCR from the peripheral blood lymphocytes (PBL) of colorectal cancer patient 4271.

PBL from colorectal cancer patient 4271 were stimulated in vitro (IVS) with autologous dendritic cells (DC). The DCs were pulsed with the G12D 24-mer peptide MTEYKLVVVGADGVGKSALTIQLI (SEQ ID NO: 88). The cells were tested by co-culturing with autologous DC which had been pulsed with the G12D 24-mer peptide or the corresponding WT 24-mer peptide MTEYKLVVVGAGGVGKSALTIQLI (SEQ ID NO: 89). Co-culturing with DC treated with DMSO and co-culturing with DC alone served as negative controls. PBL cultured in the presence of PMA served as a positive control. Reactivity was tested by IFNγ-secretion using enzyme-linked immunospot (ELISpot) assay. The results are shown in FIG. 1A. As shown in FIG. 1A, reactive cells were observed following co-culture with DCs which had been pulsed with the G12D 24-mer peptide.

Reactivity was also tested by measuring upregulation of 4-1BB and/or OX40 expression by flow cytometry assay. The results are shown in FIGS. 1B-1C. As shown in FIGS. 1B-1C, reactive cells were observed following co-culture with DCs which had been pulsed with the G12D 24-mer peptide.

Positive cells were re-stimulated and sorted by 4-1BB upregulation into 96 well plates for single-cell T-cell receptor (TCR) sequencing. Four TCRs were found, namely 4271 TCR1, 4271 TCR2, 4271 TCR3, and 4271 TCR4 (Table 5).

TABLE 5

| TCR Name | Beta chain | Alpha chain |
|---|---|---|
| 4271 TCR1 | TRBV20-1*01/TRBJ2-1*01 | TRAV14/DV4*02/TRAJ10*01 |
| 4271 TCR2 | TRBV20-1*01/TRBJ1-4*01 | TRAV13-1*01/TRAJ18*01 |
| 4271 TCR3 | TRBV11-2*01/TRBJ1-1*01 | TRAV19*01/TRAJ53*01 |
| 4271 TCR4 | TRBV4-2*01/TRBJ2-2*01 | TRAV1-2*01/TRAJ22*01 |

The sequences of the TCR alpha and beta chain variable regions were identified by single-cell TCR sequencing. The amino acid sequences of the alpha and beta chain variable regions are shown in Table 6. The CDRs are underlined. The N-terminal signal peptides are in bold font.

TABLE 6

| TCR Name | TCR chain | Amino acid sequence |
|---|---|---|
| 4271 TCR1 | Variable α (Predicted sequence without N-terminal signal peptide) | AQKITQTQPGMFVQEKEAVTLDCTYD<u>TSDQSYGLF</u>WYKQPSS GEMIFLIY<u>QGSYDEQN</u>ATEGRYSLNF<u>QKARKSAN</u>LVISASQLG DSAMYFC<u>AMREGPRGGGNKLTF</u>GTGTQLKVEL (SEQ ID NO: 7) |
| | Variable β (Predicted sequence without N-terminal signal peptide) | GAVVSQHPSWVICKSGTSVKIECRSLD<u>FQATTMF</u>WYRQFPKQS LMLMAT<u>SNEGSKAT</u>YEQGVEKDKFLINHASLTLSTLTVTSAHP EDSSFYIC<u>SANPIAANSYNEQF</u>FGPGTRLTVL (SEQ ID NO: 8) |
| | Variable α (With N-terminal signal peptide) | MSLSSLLKVVTASLWLPGIAQKITQTQPGMFVQEKEAVTLDC TYD<u>TSDQSYGLF</u>WYKQPSSGEMIFLIY<u>QGSYDEQN</u>ATEGRYSL NF<u>QKARKSAN</u>LVISASQLGDSAMYFC<u>AMREGPRGGGNKLTF</u>G TGTQLKVEL (SEQ ID NO: 9) |
| | Variable β (With N-terminal signal peptide) | MALLLLLLGPGISLLLPGSLGSGLGAVVSQHPSWVICKSGTS VKIECRSLD<u>FQATTMF</u>WYRQFPKQSLMLMAT<u>SNEGSKAT</u>YEQ GVEKDKFLINHASLTLSTLTVTSAHPEDSSFYIC<u>SANPIAANSY NEQF</u>FGPGTRLTVL (SEQ ID NO: 10) |
| 4271 TCR2 | Variable α (Predicted sequence without N-terminal signal peptide) | GENVEQHPSTLSVQEGDSAVIKCTYS<u>DSASNYF</u>PWYKQELGK GPQLIIDIRS<u>NVGEKKD</u>QRIAVTLNKTAKHFSLHITETQPEDSA VYFC<u>AATSTDRGSTLGRLYF</u>GRGTQLTVWP (SEQ ID NO: 17) |
| | Variable β (Predicted sequence without N-terminal signal peptide) | GAVVSQHPSWVICKSGTSVKIECRSLD<u>FQATTMF</u>WYRQFPKQS LMLMAT<u>SNEGSKAT</u>YEQGVEKDKFLINHASLTLSTLTVTSAHP EDSSFYIC<u>SARDPATNEKLF</u>FGSGTQLSVL (SEQ ID NO: 18) |
| | Variable α (With N-terminal signal peptide) | MTSIRAVFIFLWLQLDVNGENVEQHPSTLSVQEGDSAVIKCT YS<u>DSASNYF</u>PWYKQELGKGPQLIIDIRS<u>NVGEKKD</u>QRIAVTLN KT<u>AKHFS</u>LHITETQPEDSAVYFC<u>AATSTDRGSTLGRLYF</u>GRGT QLTVWP (SEQ ID NO: 19) |
| | Variable β (With N-terminal signal peptide) | MALLLLLLGPGISLLLPGSLGSGLGAVVSQHPSWVICKSGTS VKIECRSLD<u>FQATTMF</u>WYRQFPKQSLMLMAT<u>SNEGSKAT</u>YEQ GVEKDKFL<u>INHAS</u>LTLSTLTVTSAHPEDSSFYIC<u>SARDPATNEK LF</u>FGSGTQLSVL (SEQ ID NO: 20) |
| 4271 TCR3 | Variable α (Predicted sequence without N-terminal signal peptide) | AQKVTQAQTEISVVEKEDVTLDCVYE<u>TRDTTYYLF</u>WYKQPPS GELVFLIRR<u>NSFDEQN</u>EISGRYSWNF<u>QKSTSSF</u>NFTITASQVVD SAVYFC<u>ALSEAGAFSGGSNYKLTF</u>GKGTLLTVNP (SEQ ID NO: 27) |
| | Variable β (Predicted sequence without N-terminal signal peptide) | EAGVAQSPRYKIIEKRQSVAFWCNPI<u>SGHATLF</u>WYQQILGQGP KLLIQF<u>QNNGV</u>VDDSQLPKDRFSAERLKGVDSTLKIQPAKLED SAVYL<u>CASSLALGQGDTEAFF</u>GQGTRLTVV (SEQ ID NO: 28) |
| | Variable α (With N-terminal signal peptide) | MLTASLLRAVIASICVSSMAQKVTQAQTEISVVEKEDVTLDC VYE<u>TRDTTYYLF</u>WYKQPPSGELVFLIRR<u>NSFDEQN</u>EISGRYSW NF<u>QKSTSSF</u>NFTITASQVVDSAVYFC<u>ALSEAGAFSGGSNYKLTF</u> GKGTLLTVNP (SEQ ID NO: 29) |
| | Variable β (With N-terminal signal peptide) | MATRLLCWAALCLLGALTEAGVAQSPRYKIIEKRQSVAFWC NPI<u>SGHATLF</u>WYQQILGQGPKLLIQF<u>QNNGV</u>VDDSQLPKDRFS AERLKGVDSTLKIQPAKLEDSAVYL<u>CASSLALGQGDTEAFF</u>GQ GTRLTVV (SEQ ID NO: 30) |

TABLE 6-continued

| TCR Name | TCR chain | Amino acid sequence |
|---|---|---|
| 4271 TCR4 | Variable α (Predicted sequence without N-terminal signal peptide) | GQNIDQPTEMTATEGAIVQINCTYQTSGFNGLFWYQQHAGEA PTFLSYNVLDGLEEKGRFSSFLSRSKGYSYLLLKELQMKDSAS YLCAVESSGSARQLTFGSGTQLTVLP (SEQ ID NO: 37) |
| | Variable β (Predicted sequence without N-terminal signal peptide) | ETGVTQTPRHLVMGMTNKKSLKCEQHLGHNAMYWYKQSAK KPLELMFVYNFKEQTENNSVPSRFSPECPNSSHLFLHLHTLQPE DSALYLCASSQAWGGADGELFFGEGSRLTVL (SEQ ID NO: 38) |
| | Variable α (With N-terminal signal peptide) | MWGVFLLYVSMKMGTTGQNIDQPTEMTATEGAIVQINCTY QTSGFNGLFWYQQHAGEAPTFLSYNVLDGLEEKGRFSSFLSRS KGYSYLLLKELQMKDSASYLCAVFSSGSARQLTFGSGTQLTVL P (SEQ ID NO: 39) |
| | Variable β (With N-terminal signal peptide) | MACRLLCCAVLCLLGAPMETGVTQTPRHLVMGMTNKKSLK CEQHLGHNAMYWYKQSAKKPLELMFVYNFKEQTENNSVPSR FSPECPNSSHLFLHLHTLQPEDSALYLCASSQAWGGADGELFF GEGSRLTVL (SEQ ID NO: 40) |

Example 2

This example demonstrates the construction of retroviral vectors encoding the respective TCRs of Example 1.

Nucleotide sequences encoding the variable regions of the α and β chains of the 4271 TCR1, 4271 TCR2, 4271 TCR3, or 4271 TCR4 of Table 6 were obtained and codon-optimized. The TCRβ VDJ regions were fused to the mouse TCRβ constant chain. The TCRα VJ regions were fused to the mouse TCRα constant chain. Without being bound to a particular theory or mechanism, it is believed that replacing the constant regions of the human TCRα and TCRβ chains with the corresponding murine constant regions improves TCR expression and functionality (Cohen et al., *Cancer Res.*, 66(17): 8878-86 (2006)).

In addition, the murine TCRα and TCRβ constant chains were cysteine-modified. Transmembrane hydrophobic mutations were introduced into the murine TCRα constant chain. Without being bound to a particular theory or mechanism, it is believed that these modifications result in preferential pairing of the introduced TCR chains and enhanced TCR surface expression and functionality (Cohen et al., *Cancer Res.*, 67(8):3898-903 (2007); Haga-Friedman et al., *J. Immu.*, 188: 5538-5546 (2012)). The full length α and β chains of each of the four TCRs, including these modifications to the constant region, are shown in Table 7. In Table 7, the CDRs are underlined, and the modified amino acid residues of the constant region are underlined and in bold.

TABLE 7

| SEQ ID NO: | Sequence |
|---|---|
| SEQ ID NO: 59 (Cys-substituted, LVL-modified 4271 TCR1 α chain with N-terminal signal peptide) | MSLSSLLKVVTASLWLPGIAQKITQTQPGMFVQEKEAVTLDCTYDTSDQS YGLFWYKQPSSGEMIFLIYQGSYDEQNATEGRYSLNFQKARKSANLVISA SQLGDSAMYFCAMREGPRGGGNKLTFGTGTQLKVELNIQNPEPAVYQLK DPRSQDSTLCLFTDFDSQINVPKTMESGTFITDKCVLDMKAMDSKSNGAI AWSNQTSFTCQDIFKETNATYPSSDVPCDATLTEKSFETDMNLNFQNLLV IVLRILLLKVAGFNLLMTLRLWSS |
| SEQ ID NO: 60 (Cys-substituted, LVL-modified 4271 TCR1 β chain with N-terminal signal peptide) | MALLLLLLGPGISLLLPGSLGSGLGAVVSQHPSWVICKSGTSVKIECRSLD FQATTMFWYRQFPKQSLMLMATSNEGSKATYEQGVEKDKFLINHASLTL STLTVTSAHPEDSSFYICSANPIAANSYNEQFFGPGTRLTVLEDLRNVTPP KVSLFEPSKAEIANKQKATLVCLARGFFPDHVELSWWVNGKEVHSGVCT DPQAYKESNYSYCLSSRLRVSATFWHNPRNHFRCQVQFHGLSEEDKWPE GSPKPVTQNISAEAWGRADCGITSASYQQGVLSATILYEILLGKATLYAV LVSTLVVMAMVKRKNS |
| SEQ ID NO: 61 (Cys-substituted, LVL-modified 4271 TCR1 α chain predicted sequence without N-terminal signal peptide) | AQKITQTQPGMFVQEKEAVTLDCTYDTSDQSYGLFWYKQPSSGEMIFLIY QGSYDEQNATEGRYSLNFQKARKSANLVISASQLGDSAMYFCAMREGPR GGGNKLTFGTGTQLKVELNIQNPEPAVYQLKDPRSQDSTLCLFTDFDSQI NVPKTMESGTFITDKCVLDMKAMDSKSNGAIAWSNQTSFTCQDIFKETN ATYPSSDVPCDATLTEKSFETDMNLNFQNLLVIVLRILLLKVAGFNLLMT LRLWSS |
| SEQ ID NO: 62 (Cys-substituted, LVL-modified 4271 TCR1 β chain predicted sequence without N-terminal signal peptide) | GAVVSQHPSWVICKSGTSVKIECRSLDFQATTMFWYRQFPKQSLMLMAT SNEGSKATYEQGVEKDKFLINHASLTLSTLTVTSAHPEDSSFYICSANPIA ANSYNEQFFGPGTRLTVLEDLRNVTPPKVSLFEPSKAEIANKQKATLVCL ARGFFPDHVELSWWVNGKEVHSGVCTDPQAYKESNYSYCLSSRLRVSA TFWHNPRNHFRCQVQFHGLSEEDKWPEGSPKPVTQNISAEAWGRADCGI TSASYQQGVLSATILYEILLGKATLYAVLVSTLVVMAMVKRKNS |

TABLE 7-continued

| SEQ ID NO: | Sequence |
| --- | --- |
| SEQ ID NO: 67<br>(Cys-substituted, LVL-modified 4271 TCR2 α chain with N-terminal signal peptide) | MTSIRAVFIFLWLQLDVNGENVEQHPSTLSVQEGDSAVIKCTYSDSASNY<br>FPWYKQELGKGPQLIIDIRSNVGEKKDQRIAVTLNKTAKHFSLHITETQPE<br>DSAVYFCAATSTDRGSTLGRLYFGRGTQLTVWPNIQNPEPAVYQLKDPR<br>SQDSTLCLFTDFDSQINVPKTMESGTFITDKCVLDMKAMDSKSNGAIAWS<br>NQTSFTCQDIFKETNATYPSSDVPCDATLTEKSFETDMNLNFQNLLVIVL<br>RILLLKVAGFNLLMTLRLWSS |
| SEQ ID NO: 68<br>(Cys-substituted, LVL-modified 4271 TCR2 β chain with N-terminal signal peptide) | MALLLLLLGPGISLLLPGSLGSGLGAVVSQHPSWVICKSGTSVKIECRSLD<br>FQATTMFWYRQFPKQSLMLMATSNEGSKATYEQGVEKDKFLINHASLTL<br>STLTVTSAHPEDSSFYICSARDPATNEKLFFGSGTQLSVLEDLRNVTPPKV<br>SLFEPSKAEIANKQKATLVCLARGFFPDHVELSWWVNGKEVHSGVCTDP<br>QAYKESNYSYCLSSRLRVSATFWHNPRNHFRCQVQFHGLSEEDKWPEGS<br>PKPVTQNISAEAWGRADCGITSASYQQGVLSATILYEILLGKATLYAVLV<br>STLVVMAMVKRKNS |
| SEQ ID NO: 69<br>(Cys-substituted, LVL-modified 4271 TCR2 α chain predicted sequence without N-terminal signal peptide) | GENVEQHPSTLSVQEGDSAVIKCTYSDSASNYFPWYKQELGKGPQLIIDIR<br>SNVGEKKDQRIAVTLNKTAKHFSLHITETQPEDSAVYFCAATSTDRGSTL<br>GRLYFGRGTQLTVWPNIQNPEPAVYQLKDPRSQDSTLCLFTDFDSQINVP<br>KTMESGTFITDKCVLDMKAMDSKSNGAIAWSNQTSFTCQDIFKETNATY<br>PSSDVPCDATLTEKSFETDMNLNFQNLLVIVLRILLLKVAGFNLLMTLRL<br>WSS |
| SEQ ID NO: 70<br>(Cys-substituted, LVL-modified 4271 TCR2 β chain predicted sequence without N-terminal signal peptide) | GAVVSQHPSWVICKSGTSVKIECRSLDFQATTMFWYRQFPKQSLMLMAT<br>SNEGSKATYEQGVEKDKFLINHASLTLSTLTVTSAHPEDSSFYICSARDPA<br>TNEKLFFGSGTQLSVLEDLRNVTPPKVSLFEPSKAEIANKQKATLVCLAR<br>GFFPDHVELSWWVNGKEVHSGVCTDPQAYKESNYSYCLSSRLRVSATF<br>WHNPRNHFRCQVQFHGLSEEDKWPEGSPKPVTQNISAEAWGRADCGITS<br>ASYQQGVLSATILYEILLGKATLYAVLVSTLVVMAMVKRKNS |
| SEQ ID NO: 75<br>(Cys-substituted, LVL-modified 4271 TCR3 α chain with N-terminal signal peptide) | MLTASLLRAVIASICVSSMAQKVTQAQTEISVVEKEDVTLDCVYETRDTT<br>YYLFWYKQPPSGELVFLIRRNSFDEQNEISGRYSWNFQKSTSSFNFTITAS<br>QVVDSAVYFCALSEAGAFSGGSNYKLTFGKGTLLTVNPNIQNPEPAVYQ<br>LKDPRSQDSTLCLFTDFDSQINVPKTMESGTFITDKCVLDMKAMDSKSNG<br>AIAWSNQTSFTCQDIFKETNATYPSSDVPCDATLTEKSFETDMNLNFQNL<br>LVIVLRILLLKVAGFNLLMTLRLWSS |
| SEQ ID NO: 76<br>(Cys-substituted, LVL-modified 4271 TCR3 β chain with N-terminal signal peptide) | MATRLLCWAALCLLGALTEAGVAQSPRYKIIEKRQSVAFWCNPISGHAT<br>LYWYQQILGQGPKLLIQFQNNGVVDDSQLPKDRFSAERLKGVDSTLKIQP<br>AKLEDSAVYLCASSLALGQGDTEAFFGQGTRLTVVEDLRNVTPPKVSLFE<br>PSKAEIANKQKATLVCLARGFFPDHVELSWWVNGKEVHSGVCTDPQAY<br>KESNYSYCLSSRLRVSATFWHNPRNHFRCQVQFHGLSEEDKWPEGSPKP<br>VTQNISAEAWGRADCGITSASYQQGVLSATILYEILLGKATLYAVLVSTL<br>VVMAMVKRKNS |
| SEQ ID NO: 77<br>(Cys-substituted, LVL-modified 4271 TCR3 α chain predicted sequence without N-terminal signal peptide) | AQKVTQAQTEISVVEKEDVTLDCVYETRDTTYYLFWYKQPPSGELVFLIR<br>RNSFDEQNEISGRYSWNFQKSTSSFNFTITASQVVDSAVYFCALSEAGAFS<br>GGSNYKLTFGKGTLLTVNPNIQNPEPAVYQLKDPRSQDSTLCLFTDFDSQI<br>NVPKTMESGTFITDKCVLDMKAMDSKSNGAIAWSNQTSFTCQDIFKETN<br>ATYPSSDVPCDATLTEKSFETDMNLNFQNLLVIVLRILLLKVAGFNLLMT<br>LRLWSS |
| SEQ ID NO: 78<br>(Cys-substituted, LVL-modified 4271 TCR3 β chain predicted sequence without N-terminal signal peptide) | EAGVAQSPRYKIIEKRQSVAFWCNPISGHATLYWYQQILGQGPKLLIQFQ<br>NNGVVDDSQLPKDRFSAERLKGVDSTLKIQPAKLEDSAVYLCASSLALG<br>QGDTEAFFGQGTRLTVVEDLRNVTPPKVSLFEPSKAEIANKQKATLVCLA<br>RGFFPDHVELSWWVNGKEVHSGVCTDPQAYKESNYSYCLSSRLRVSATF<br>WHNPRNHFRCQVQFHGLSEEDKWPEGSPKPVTQNISAEAWGRADCGITS<br>ASYQQGVLSATILYEILLGKATLYAVLVSTLVVMAMVKRKNS |
| SEQ ID NO: 83<br>(Cys-substituted, LVL-modified 4271 TCR4 α chain with N-terminal signal peptide) | MWGVFLLYVSMKMGTTGQNIDQPTEMTATEGAIVQINCTYQTSGFNGLF<br>WYQQHAGEAPTFLSYNVLDGLEEKGRFSSFLSRSKGYSYLLLKELQMKD<br>SASYLCAVFSSGSARQLTFGSGTQLTVLPNIQNPEPAVYQLKDPRSQDSTL<br>CLFTDFDSQINVPKTMESGTFITDKCVLDMKAMDSKSNGAIAWSNQTSFT<br>CQDIFKETNATYPSSDVPCDATLTEKSFETDMNLNFQNLLVIVLRILLLKV<br>AGFNLLMTLRLWSS |
| SEQ ID NO: 84<br>(Cys-substituted, LVL-modified 4271 TCR4 β chain with N-terminal signal peptide) | MACRLLCCAVLCLLGAPMETGVTQTPRHLVMGMTNKKSLKCEQHLGH<br>NAMYWYKQSAKKPLELMFVYNFKEQTENNSVPSRFSPECPNSSHLFLHL<br>HTLQPEDSALYLCASSQAWGGADGELFFGEGSRLTVEDLRNVTPPKVS<br>LFEPSKAEIANKQKATLVCLARGFFPDHVELSWWVNGKEVHSGVCTDPQ<br>AYKESNYSYCLSSRLRVSATFWHNPRNHFRCQVQFHGLSEEDKWPEGSP<br>KPVTQNISAEAWGRADCGITSASYQQGVLSATILYEILLGKATLYAVLVS<br>TLVVMAMVKRKNS |
| SEQ ID NO: 85<br>(Cys-substituted, LVL-modified 4271 TCR4 α chain predicted sequence without N-terminal signal peptide) | GQNIDQPTEMTATEGAIVQINCTYQTSGFNGLFWYQQHAGEAPTFLSYN<br>VLDGLEEKGRFSSFLSRSKGYSYLLLKELQMKDSASYLCAVFSSGSARQL<br>TFGSGTQLTVLPNIQNPEPAVYQLKDPRSQDSTLCLFTDFDSQINVPKTME<br>SGTFITDKCVLDMKAMDSKSNGAIAWSNQTSFTCQDIFKETNATYPSSDV<br>PCDATLTEKSFETDMNLNFQNLLVIVLRILLLKVAGFNLLMTLRLWSS |

TABLE 7-continued

| SEQ ID NO: | Sequence |
|---|---|
| SEQ ID NO: 86<br>(Cys-substituted, LVL-<br>modified 4271 TCR4 β<br>chain predicted sequence<br>without N-terminal<br>signal peptide) | ETGVTQTPRHLVMGMTNKKSLKCEQHLGHNAMYWYKQSAKKPLELMF<br>VYNFKEQTENNSVPSRFSPECPNSSHLFLHLHTLQPEDSALYLCASSQAW<br>GGADGELFFGEGSRLTVLEDLRNVTPPKVSLFEPSKAEIANKQKATLVCL<br>ARGFFPDHVELSWWVNGKEVHSGVCTDPQAYKESNYSYCLSSRLRVSA<br>TFWHNPRNHFRCQVQFHGLSEEDKWPEGSPKPVTQNISAEAWGRADCGI<br>TSASYQQGVLSATILYEILLGKATLYAVLVSTLVVMAMVKRKNS |

Nucleotide sequences encoding the variable regions of the α and β chains of the 4271 TCR1, 4271 TCR2, 4271 TCR3, or 4271 TCR4 of Table 7 were independently cloned into a MSGV1-based retroviral vectors with the following expression cassette for each respective TCR is shown in Table 8. In Table 8, the CDRs are underlined, the constant regions are italicized, and the linker peptide is shown in bold.

TABLE 8

| TCR Name | Amino acid sequence encoded by TCR Expression Cassette |
|---|---|
| 4271 TCR1 | MALLLLLLGPGISLLLPGSLGSGLGAVVSQHPSWVICKSGTSVKIECRSLDFQATTMFWYRQFPKQSLMLMAT<br>SNEGSKATYEQGVEKDKFLINHASLTLSTLTVTSAHPEDSSFYICSANPIAANSYNEQFFGPGTRLTVLEDLR<br>NVTPPKVSLFEPSKAEIANKQKATLVCLARGFFPDHVELSWWVNGKEVHSGVCTDPQAYKESNYSYCLSSRLR<br>VSATFWHNPRNHFRCQVQFHGLSEEDKWPEGSPKPVTQNISAEAWGRADCGITSASYQQGVLSATILYEILLG<br>KATLYAVLVSTLVVMAMVKRKNSRAKRSGSGATNFSLLKQAGDVEENPGPMSLSSLLKVVTASLWLPGIAQKI<br>TQTQPGMFVQEKEAVTLDCTYDTSDQSYGLFWYKQPSSGEMIFLIYQGSYDEQNATEGRYSLNFQKARKSANL<br>VISASQLGDSAMYFCAMREGPRGGGNKLTFGTGTQLKVELNIQNPEPAVYQLKDPRSQDSTLCLFTDFDSQIN<br>VPKTMESGTFITDKCVLDMKAMDSKSNGAIAWSNQTSFTCQDIFKETNATYPSSDVPCDATLTEKSFETDMNL<br>NFQNLLVIVLRILLLKVAGFNLLMTLRLWSS (SEQ ID NO: 91) |
| 4271 TCR2 | MALLLLLLGPGISLLLPGSLGSGLGAVVSQHPSWVICKSGTSVKIECRSLDFQATTMFWYRQFPKQSLMLMAT<br>SNEGSKATYEQGVEKDKFLINHASLTLSTLTVTSAHPEDSSFYICSARDPATNEKLFFGSGTQLSVLEDLRNV<br>TPPKVSLFEPSKAEIANKQKATLVCLARGFFPDHVELSWWVNGKEVHSGVCTDPQAYKESNYSYCLSSRLRVS<br>ATFWHNPRNHFRCQVQFHGLSEEDKWPEGSPKPVTQNISAEAWGRADCGITSASYQQGVLSATILYEILLGKA<br>TLYAVLVSTLVVMAMVKRKNSRAKRSGSGATNFSLLKQAGDVEENPGPMTISRAVFIFLWLQLDVNGENVEQH<br>PSTLSVQEGDSAVIKCTYSDSASNYFPWYKQELGKGPQLIIDIRSNVGEKKDQRIAVTLNKTAKHFSLHITET<br>QPEDSAVYFCAATSTDRGSTLGRLYFGRGTQLTVWPNIQNPEPAVYQLKDPRSQDSTLCLFTDFDSQINVPKT<br>MESGTFITDKCVLDMKAMDSKSNGAIAWSNQTSFTCQDIFKETNATYPSSDVPCDATLTEKSFETDMNLNFQN<br>LLVIVRILLLKVAGFNLLMTLRLWSS (SEQ ID NO: 92) |
| 4271 TCR3 | MATRLLCWAALCLLGALTEAGVAQSPRYKIIEKRQSVAFWCNPISGHATLYWYQQILGQGPKLLIQFQNNGVV<br>DDSQLPKDRFSAERLKGVDSTLKIQPAKLEDSAVYLCASSLALGQGDTEAFFGQGTRLTVVEDLRNVTPPKVS<br>LFEPSKAEIANKQKATLVCLARGFFPDHVELSWWVNGKEVHSGVCTDPQAYKESNYSYCLSSRLRVSATFWHN<br>PRNHFRCQVQFHGLSEEDKWPEGSPKPVTQNISAEAWGRADCGITSASYQQGVLSATILYEILLGKATLYAVL<br>VSTLVVMAMVKRKNSRAKRSGSGATNFSLLKQAGDVEENPGPMLTASLLRAVIASICVSSMAQKVTQAQTIES<br>VVEKEDVTLDCVYETRDTTYYLFWYKQQQSGELVFLIRRNSPDEQNEISGRYSWNFQKSTSSFNFTITASQVV<br>DSAVYFCALSEAGAFSGGSNYKLTFGKGTLLTVNPNIQNPEPAVYQLKDPRSQDSTLCLFTDFDSQINVPKTM<br>ESGTFITDKCVLDMKAMDSKSNGAIAWSNQTSFTCQDIFKETNATYPSSDVPCDATLTEKSFETDMNLNFQNL<br>LVIVLRILLLKVAGFNLLMTLRLWSS (SEQ ID NO: 93) |
| 4271 TCR4 | MACRLLCCAVLCLLGAPMETCVTQTPRHLVMGMTNKKSLKCEQHLGHNAMYWYKQSAKKPLELMFVYNFKEQT<br>ENNSVPSRFSPECPNSSHLFLHLHTLQPEDSALYLCASSQAWGGADGELFFGEGSRLTVLEDLRNVTPPKVSL<br>FEPSKAEIANKQKATLVCLARGFFPDHVELSWWVNGKEVHSGVCTDPQAYKESNYSYCLSRLRVSATFWHNPR<br>NHFRCQVQFHGLSEEDKWPEGSPKPVTQNISAEAWGRADCGITSASYQQGVLSATILYEILLGKATLYAVLVS<br>TLVVMAMVKRKNSRAKRSGSGATNFSLLKQAGDVEENPGPMWGVFLLYVSMKMGTTGQNIDQPTEMTATEGIA<br>VQINCTYQTSGFNGLFWYQQHAGEAPTFLSYNVLDGLEEKGRFSSFLSRSKGYSYLLLKELQMKDSASYLCAV<br>FSSGSARQLTFGSGTQLTVLPNIQNPEPAVYQLKDPRSQDSTLCLFTDFDSQINVPKTMESGTFITDKCVLDM<br>KAMDSKSNGAIAWSNQTSFTCQDIFKETNATYPSSDVPCDATLTEKSFETDMNLNFQNLLVIVLRILLLKVAG<br>FNLLMTLRLWSS (SEQ ID NO: 94) | sion cassette configuration: 5'NcoI-VDJβ-mCβ-Furin/Ser-Gly/P2A-VJα-mCα-EcoRI3'. To facilitate cloning of the TCR expression cassette into the MSGV1 vector 5'NcoI site, the second amino acid in the N-terminal signal peptide of the TCRVβ chain was changed to an alanine (A).

The TCRβ and TCRα chains were separated by a Furin Ser/Gly P2A linker peptide (SEQ ID NO: 87). Without being bound to a particular theory or mechanism, it is believed that the linker peptide provides comparable expression efficiency of the two chains (Szymczak et al., *Nat. Biotechnol.*, 22(5): 589-94 (2004)).

The TCR expression cassette of the retroviral vector encoded, from 5' to 3', the TCRβ and TCRα chains separated by the linker peptide. The amino acid sequence encoded by Example 3

This example demonstrates the avidity of the TCRs expressed by the retroviral vectors of Example 2.

Autologous PBL were independently transduced with a retroviral vector encoding the 4271 TCR1, 4271 TCR2, 4271 TCR3, or 4271 TCR4 of Example 2.

Autologous DCs were loaded with the G12D 24-mer peptide or the corresponding WT 24-mer peptide of Example 1 at one of the various concentrations shown in FIGS. 2A-2D. The cells were washed twice and co-cultured overnight with transduced T cells at a ratio of 6e4 DC:5e4 T cells. 4-1BB and/or OX40 upregulation was evaluated by fluorescence activated cell sorting (FACS). The results are shown in FIGS. 2A-2D.

Example 4

This example demonstrates that the TCRs expressed by the retroviral vectors of Example 2 recognize G12D RAS presented by an HLA-DR molecule.

The MHC Class II molecules expressed by Patient 4271 were determined using exome and mRNA sequencing. The expressed MHC Class II molecules are shown in Table 9.

TABLE 9

| 4271 MHC-II | |
| --- | --- |
| DQA1-1 - 01:02 | DRB1*03:01 |
| DQA1-2 - 05:01 | DRB1*11:01 |
| DQB1-1 - 02:01 | DRB3*01:01:02 |
| DQB1-2 - 05:02 | DRB3*03:01:01 |
| DPA-1 - 02:01 | DRB4*03:01 |
| DPA-2 - 03:03 | |
| DPB1-1 - 01:01 | |
| DPB1-2 - 04:02 | |

Autologous DCs (target cells) were pulsed with the G12D 24-mer peptide after treating the target cells with anti-HLA DP, anti-HLA DQ, or anti-HLA DR antibodies or with no blocking antibodies. The target cells were then co-cultured with effector cells. The effector cells were autologous T cells independently transduced with a retroviral vector encoding the 4271 TCR1, 4271 TCR2, 4271 TCR3, or 4271 TCR4 of Example 2. Effector cells cultured in the presence of anti-CD3/anti-CD28 Dynabeads served as a positive control. The anti-CD3/anti-CD28 Dynabeads non-specifically stimulate the effector cells. Effector cells cultured in the presence of DMSO served as a negative control.

IFN-γ secretion was measured by ELISPOT. OX40 and/or 4-1BB upregulation was measured by FACS. The results are shown in FIGS. 3A-3B.

As shown in FIGS. 3A-3B, OX40 and/or 4-1BB upregulation and IFN-γ secretion was blocked in the presence of anti-HLA DR antibodies.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a T-cell receptor (TCR) comprising:

(a) the alpha chain complementarity determining region (CDR)1 amino acid sequence of SEQ ID NO: 1, the alpha chain CDR2 amino acid sequence of SEQ ID NO: 2, the alpha chain CDR3 amino acid sequence of SEQ ID NO: 3, the beta chain CDR1 amino acid sequence of SEQ ID NO: 4, the beta chain CDR2 amino acid sequence of SEQ ID NO: 5, and the beta chain CDR3 amino acid sequence of SEQ ID NO: 6;

(b) the alpha chain CDR1 amino acid sequence of SEQ ID NO: 11, the alpha chain CDR2 amino acid sequence of SEQ ID NO: 12, the alpha chain CDR3 amino acid sequence of SEQ ID NO: 13, the beta chain CDR1 amino acid sequence of SEQ ID NO: 14, the beta chain CDR2 amino acid sequence of SEQ ID NO: 15, and the beta chain CDR3 amino acid sequence of SEQ ID NO: 16;

(c) the alpha chain CDR1 amino acid sequence of SEQ ID NO: 21, the alpha chain CDR2 amino acid sequence of SEQ ID NO: 22, the alpha chain CDR3 amino acid sequence of SEQ ID NO: 23, the beta chain CDR1 amino acid sequence of SEQ ID NO: 24, the beta chain CDR2 amino acid sequence of SEQ ID NO: 25, and the beta chain CDR3 amino acid sequence of SEQ ID NO: 26; or (d) the alpha chain CDR1 amino acid sequence of SEQ ID NO: 31, the alpha chain CDR2 amino acid sequence of SEQ ID NO: 32, the alpha chain CDR3 amino acid sequence of SEQ ID NO: 33, the beta chain CDR1 amino acid sequence of SEQ ID NO: 34, the beta chain CDR2 amino acid sequence of SEQ ID NO: 35, and the beta chain CDR3 amino acid sequence of SEQ ID NO: 36, wherein the TCR has antigenic specificity for a mutated human RAS amino acid sequence with a substitution of glycine at position 12 with aspartic acid, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and wherein position 12 is defined by reference to the wild-type human KRAS, wild-type human HRAS, or wild-type human NRAS protein, respectively.

2. The nucleic acid according to claim 1, wherein the mutated human RAS amino acid sequence is MTEYKLVVVGADGVGKSALTIQLI (SEQ ID NO: 88).

3. The nucleic acid according to claim 1, wherein the TCR does not have antigenic specificity for the wild-type human RAS amino acid sequence of

```
                                    (SEQ ID NO: 89)
MTEYKLVVVGAGGVGKSALTIQLI.
```

4. The nucleic acid according to claim 1, wherein the mutated human RAS amino acid sequence is presented by a human leukocyte antigen (HLA) Class II molecule.

5. The nucleic acid according to claim 4, wherein the HLA Class II molecule is an HLA-DR heterodimer.

6. The nucleic acid according to claim 4, wherein the HLA Class II molecule comprises an HLA-DR α chain in combination with a HLA-DR β chain encoded by any one of the HLA-DRB1 gene, the HLA-DRB3 gene, or the HLA-DRB4 gene.

7. The nucleic acid according to claim 4, wherein the HLA Class II molecule is an HLA-DRB1*03:HLA-DRA*01 heterodimer, an HLA-DRB1*11:HLA-DRA*01 heterodimer, an HLA-DRB3*01:HLA-DRA*01 heterodimer, an HLA-DRB3*03:HLA-DRA*01 heterodimer, an HLA-DRB4*03:HLA-DRA*01 heterodimer, or an HLA-DRB4*01:HLA-DRA*01 heterodimer.

8. The nucleic acid according to claim 1, wherein the TCR comprises the amino acid sequences of:
(i) SEQ ID NO: 7,
(ii) SEQ ID NO: 8,
(iii) SEQ ID NO: 9,
(iv) SEQ ID NO: 10,
(v) SEQ ID NO: 17,
(vi) SEQ ID NO: 18,
(vii) SEQ ID NO: 19,
(viii) SEQ ID NO: 20,
(ix) SEQ ID NO: 27,
(x) SEQ ID NO: 28,
(xi) SEQ ID NO: 29,
(xii) SEQ ID NO: 30,
(xiii) SEQ ID NO: 37,
(xiv) SEQ ID NO: 38,
(xv) SEQ ID NO: 39,
(xvi) SEQ ID NO: 40,
(xvii) both of SEQ ID NOs: 7 and 8,
(xviii) both of SEQ ID NOs: 9 and 10,
(xix) both of SEQ ID NOs: 17 and 18,
(xx) both of SEQ ID NOs: 19 and 20,
(xxi) both of SEQ ID NOs: 27 and 28,
(xxii) both of SEQ ID NOs: 29 and 30,
(xxiii) both of SEQ ID NOs: 37 and 38, or
(xxiv) both of SEQ ID NOs: 39 and 40.

9. The nucleic acid of claim 1, wherein the TCR further comprises:
(a) an α chain constant region comprising the amino acid sequence of SEQ ID NO: 49, wherein:
(i) X at position 48 of SEQ ID NO: 49 is Thr or Cys;
(ii) X at position 112 of SEQ ID NO: 49 is Ser, Ala, Val, Leu, Ile, Pro, Phe, Met, or Trp;

(iii) X at position 114 of SEQ ID NO: 49 is Met, Ala, Val, Leu, Ile, Pro, Phe, or Trp; and
(iv) X at position 115 of SEQ ID NO: 49 is Gly, Ala, Val, Leu, Ile, Pro, Phe, Met, or Trp;
(b) a β chain constant region comprising the amino acid sequence of SEQ ID NO: 50, wherein X at position 57 of SEQ ID NO: 50 is Ser or Cys; or
(c) both (a) and (b).

10. The isolated or purified nucleic acid of claim 1, wherein the TCR comprises:
(a) an α chain comprising the amino acid sequence of SEQ ID NO: 55, wherein:
(i) X at position 184 of SEQ ID NO: 55 is Thr or Cys;
(ii) X at position 248 of SEQ ID NO: 55 is Ser, Ala, Val, Leu, Ile, Pro, Phe, Met, or Trp;
(iii) X at position 250 of SEQ ID NO: 55 is Met, Ala, Val, Leu, Ile, Pro, Phe, or Trp; and
(iv) X at position 251 of SEQ ID NO: 55 is Gly, Ala, Val, Leu, Ile, Pro, Phe, Met, or Trp;
(b) a β chain comprising the amino acid sequence of SEQ ID NO: 56, wherein X at position 199 of SEQ ID NO: 56 is Ser or Cys;
(c) both (a) and (b);
(d) an α chain comprising the amino acid sequence of SEQ ID NO: 57, wherein:
(i) X at position 165 of SEQ ID NO: 57 is Thr or Cys;
(ii) X at position 229 of SEQ ID NO: 57 is Ser, Ala, Val, Leu, Ile, Pro, Phe, Met, or Trp;
(iii) X at position 231 of SEQ ID NO: 57 is Met, Ala, Val, Leu, Ile, Pro, Phe, or Trp; and
(iv) X at position 232 of SEQ ID NO: 57 is Gly, Ala, Val, Leu, Ile, Pro, Phe, Met, or Trp;
(e) a β chain comprising the amino acid sequence of SEQ ID NO: 58, wherein X at position 175 of SEQ ID NO: 58 is Ser or Cys;
(f) both (d) and (e);
(g) SEQ ID NO: 59;
(h) SEQ ID NO: 60;
(i) SEQ ID NO: 61;
(j) SEQ ID NO: 62;
(k) both (g) and (h);
(l) both (i) and (j);
(m) an α chain comprising the amino acid sequence of SEQ ID NO: 63, wherein:
(i) X at position 182 of SEQ ID NO: 63 is Thr or Cys;
(ii) X at position 246 of SEQ ID NO: 63 is Ser, Ala, Val, Leu, Ile, Pro, Phe, Met, or Trp;
(iii) X at position 248 of SEQ ID NO: 63 is Met, Ala, Val, Leu, Ile, Pro, Phe, or Trp; and
(iv) X at position 249 of SEQ ID NO: 63 is Gly, Ala, Val, Leu, Ile, Pro, Phe, Met, or Trp;
(n) a β chain comprising the amino acid sequence of SEQ ID NO: 64, wherein X at position 197 of SEQ ID NO: 64 is Ser or Cys;
(o) both (m) and (n);
(p) an α chain comprising the amino acid sequence of SEQ ID NO: 65, wherein:
(i) X at position 164 of SEQ ID NO: 65 is Thr or Cys;
(ii) X at position 228 of SEQ ID NO: 65 is Ser, Ala, Val, Leu, Ile, Pro, Phe, Met, or Trp;
(iii) X at position 230 of SEQ ID NO: 65 is Met, Ala, Val, Leu, Ile, Pro, Phe, or Trp; and
(iv) X at position 231 of SEQ ID NO: 65 is Gly, Ala, Val, Leu, Ile, Pro, Phe, Met, or Trp;
(q) a β chain comprising the amino acid sequence of SEQ ID NO: 66, wherein X at position 173 of SEQ ID NO: 66 is Ser or Cys;

(r) both (p) and (q);

(s) SEQ ID NO: 67;

(t) SEQ ID NO: 68;

(u) SEQ ID NO: 69;

(v) SEQ ID NO: 70;

(w) both (s) and (t);

(x) both (u) and (v);

(y) an α chain comprising the amino acid sequence of SEQ ID NO: 71, wherein:

(i) X at position 187 of SEQ ID NO: 71 is Thr or Cys;

(ii) X at position 251 of SEQ ID NO: 71 is Ser, Ala, Val, Leu, Ile, Pro, Phe, Met, or Trp;

(iii) X at position 253 of SEQ ID NO: 71 is Met, Ala, Val, Leu, Ile, Pro, Phe, or Trp; and (iv) X at position 254 of SEQ ID NO: 71 is Gly, Ala, Val, Leu, Ile, Pro, Phe, Met, or Trp;

(z) a β chain comprising the amino acid sequence of SEQ ID NO: 72, wherein X at position 191 of SEQ ID NO: 72 is Ser or Cys;

(aa) both (y) and (z);

(bb) an α chain comprising the amino acid sequence of SEQ ID NO: 73, wherein:

(i) X at position 168 of SEQ ID NO: 73 is Thr or Cys;

(ii) X at position 232 of SEQ ID NO: 73 is Ser, Ala, Val, Leu, Ile, Pro, Phe, Met, or Trp;

(iii) X at position 234 of SEQ ID NO: 73 is Met, Ala, Val, Leu, Ile, Pro, Phe, or Trp; and (iv) X at position 235 of SEQ ID NO: 73 is Gly, Ala, Val, Leu, Ile, Pro, Phe, Met, or Trp;

(cc) a β chain comprising the amino acid sequence of SEQ ID NO: 74, wherein X at position 173 of SEQ ID NO: 74 is Ser or Cys;

(dd) both (bb) and (cc);

(ee) SEQ ID NO: 75;

(ff) SEQ ID NO: 76;

(gg) SEQ ID NO: 77;

(hh) SEQ ID NO: 78;

(ii) both (ee) and (ff);

(jj) both (gg) and (hh);

(kk) an α chain comprising the amino acid sequence of SEQ ID NO: 79, wherein:

(i) X at position 175 of SEQ ID NO: 79 is Thr or Cys;

(ii) X at position 239 of SEQ ID NO: 79 is Ser, Ala, Val, Leu, Ile, Pro, Phe, Met, or Trp;

(iii) X at position 241 of SEQ ID NO: 79 is Met, Ala, Val, Leu, Ile, Pro, Phe, or Trp; and (iv) X at position 242 of SEQ ID NO: 79 is Gly, Ala, Val, Leu, Ile, Pro, Phe, Met, or Trp;

(ll) a β chain comprising the amino acid sequence of SEQ ID NO: 80, wherein X at position 190 of SEQ ID NO: 80 is Ser or Cys;

(mm) both (kk) and (ll);

(nn) an α chain comprising the amino acid sequence of SEQ ID NO: 81, wherein:

(i) X at position 159 of SEQ ID NO: 81 is Thr or Cys;

(ii) X at position 223 of SEQ ID NO: 81 is Ser, Ala, Val, Leu, Ile, Pro, Phe, Met, or Trp;

(iii) X at position 225 of SEQ ID NO: 81 is Met, Ala, Val, Leu, Ile, Pro, Phe, or Trp; and (iv) X at position 226 of SEQ ID NO: 81 is Gly, Ala, Val, Leu, Ile, Pro, Phe, Met, or Trp;

(oo) a β chain comprising the amino acid sequence of SEQ ID NO: 82, wherein X at position 172 of SEQ ID NO: 82 is Ser or Cys;

(pp) both (nn) and (oo);

(qq) SEQ ID NO: 83;

(rr) SEQ ID NO: 84;

(ss) SEQ ID NO: 85;

(tt) SEQ ID NO: 86;

(uu) both (qq) and (rr); or (vv) both (ss) and (tt).

11. An isolated or purified nucleic acid comprising a nucleotide sequence encoding a polypeptide, wherein the polypeptide comprises a functional portion of the TCR of claim 1, and wherein the functional portion comprises:

(a) the alpha chain complementarity determining region (CDR)1 amino acid sequence of SEQ ID NO: 1, the alpha chain CDR2 amino acid sequence of SEQ ID NO: 2, the alpha chain CDR3 amino acid sequence of SEQ ID NO: 3, the beta chain CDR1 amino acid sequence of SEQ ID NO: 4, the beta chain CDR2 amino acid sequence of SEQ ID NO: 5, and the beta chain CDR3 amino acid sequence of SEQ ID NO: 6;

(b) the alpha chain CDR1 amino acid sequence of SEQ ID NO: 11, the alpha chain CDR2 amino acid sequence of SEQ ID NO: 12, the alpha chain CDR3 amino acid sequence of SEQ ID NO: 13, the beta chain CDR1 amino acid sequence of SEQ ID NO: 14, the beta chain CDR2 amino acid sequence of SEQ ID NO: 15, and the beta chain CDR3 amino acid sequence of SEQ ID NO: 16;

(c) the alpha chain CDR1 amino acid sequence of SEQ ID NO: 21, the alpha chain CDR2 amino acid sequence of SEQ ID NO: 22, the alpha chain CDR3 amino acid sequence of SEQ ID NO: 23, the beta chain CDR1 amino acid sequence of SEQ ID NO: 24, the beta chain CDR2 amino acid sequence of SEQ ID NO: 25, and the beta chain CDR3 amino acid sequence of SEQ ID NO: 26; or (d) the alpha chain CDR1 amino acid sequence of SEQ ID NO: 31, the alpha chain CDR2 amino acid sequence of SEQ ID NO: 32, the alpha chain CDR3 amino acid sequence of SEQ ID NO: 33, the beta chain CDR1 amino acid sequence of SEQ ID NO: 34, the beta chain CDR2 amino acid sequence of SEQ ID NO: 35, and the beta chain CDR3 amino acid sequence of SEQ ID NO: 36.

12. The isolated or purified nucleic acid according to claim 11, wherein the functional portion comprises the amino acid sequence(s) of:

(i) SEQ ID NO: 7, (ii) SEQ ID NO: 8, (iii) SEQ ID NO: 9, (iv) SEQ ID NO: 10, (v) SEQ ID NO: 17, (vi) SEQ ID NO: 18, (vii) SEQ ID NO: 19, (viii) SEQ ID NO: 20, (ix) SEQ ID NO: 27, (x) SEQ ID NO: 28, (xi) SEQ ID NO: 29, (xii) SEQ ID NO: 30, (xiii) SEQ ID NO: 37, (xiv) SEQ ID NO: 38, (xv) SEQ ID NO: 39, (xvi) SEQ ID NO: 40, (xvii) both of SEQ ID NOs: 7 and 8, (xviii) both of SEQ ID NOs: 9 and 10, (xix) both of SEQ ID NOs: 17 and 18, (xx) both of SEQ ID NOs: 19 and 20, (xxi) both of SEQ ID NOs: 27 and 28, (xxii) both of SEQ ID NOs: 29 and 30, (xxiii) both of SEQ ID NOs: 37 and 38, or (xxiv) both of SEQ ID NOs: 39 and 40.

13. The isolated or purified nucleic acid of claim 11, wherein the polypeptide further comprises:

(a) the amino acid sequence of SEQ ID NO: 49, wherein:

(i) X at position 48 of SEQ ID NO: 49 is Thr or Cys;

(ii) X at position 112 of SEQ ID NO: 49 is Ser, Ala, Val, Leu, Ile, Pro, Phe, Met, or Trp;

(iii) X at position 114 of SEQ ID NO: 49 is Met, Ala, Val, Leu, Ile, Pro, Phe, or Trp; and (iv) X at position 115 of SEQ ID NO: 49 is Gly, Ala, Val, Leu, Ile, Pro, Phe, Met, or Trp;

(b) the amino acid sequence of SEQ ID NO: 50, wherein X at position 57 of SEQ ID NO: 50 is Ser or Cys; or (c) both (a) and (b).

14. The isolated or purified nucleic acid of claim 11, wherein the polypeptide comprises:

(a) an α chain comprising the amino acid sequence of SEQ ID NO: 55, wherein:

(i) X at position 184 of SEQ ID NO: 55 is Thr or Cys;

(ii) X at position 248 of SEQ ID NO: 55 is Ser, Ala, Val, Leu, Ile, Pro, Phe, Met, or Trp;

(iii) X at position 250 of SEQ ID NO: 55 is Met, Ala, Val, Leu, Ile, Pro, Phe, or Trp; and (iv) X at position 251 of SEQ ID NO: 55 is Gly, Ala, Val, Leu, Ile, Pro, Phe, Met, or Trp;

(b) a β chain comprising the amino acid sequence of SEQ ID NO: 56, wherein X at position 199 of SEQ ID NO: 56 is Ser or Cys;

(c) both (a) and (b);

(d) an α chain comprising the amino acid sequence of SEQ ID NO: 57, wherein:

(i) X at position 165 of SEQ ID NO: 57 is Thr or Cys;

(ii) X at position 229 of SEQ ID NO: 57 is Ser, Ala, Val, Leu, Ile, Pro, Phe, Met, or Trp;

(iii) X at position 231 of SEQ ID NO: 57 is Met, Ala, Val, Leu, Ile, Pro, Phe, or Trp; and (iv) X at position 232 of SEQ ID NO: 57 is Gly, Ala, Val, Leu, Ile, Pro, Phe, Met, or Trp;

(e) a β chain comprising the amino acid sequence of SEQ ID NO: 58, wherein X at position 175 of SEQ ID NO: 58 is Ser or Cys;

(f) both (d) and (e);

(g) SEQ ID NO: 59;

(h) SEQ ID NO: 60;

(i) SEQ ID NO: 61;

(j) SEQ ID NO: 62;

(k) both (g) and (h);

(l) both (i) and (j);

(m) an α chain comprising the amino acid sequence of SEQ ID NO: 63, wherein:

(i) X at position 182 of SEQ ID NO: 63 is Thr or Cys;

(ii) X at position 246 of SEQ ID NO: 63 is Ser, Ala, Val, Leu, Ile, Pro, Phe, Met, or Trp;

(iii) X at position 248 of SEQ ID NO: 63 is Met, Ala, Val, Leu, Ile, Pro, Phe, or Trp; and (iv) X at position 249 of SEQ ID NO: 63 is Gly, Ala, Val, Leu, Ile, Pro, Phe, Met, or Trp;

(n) a β chain comprising the amino acid sequence of SEQ ID NO: 64, wherein X at position 197 of SEQ ID NO: 64 is Ser or Cys;

(o) both (m) and (n);

(p) an α chain comprising the amino acid sequence of SEQ ID NO: 65, wherein:

(i) X at position 164 of SEQ ID NO: 65 is Thr or Cys;

(ii) X at position 228 of SEQ ID NO: 65 is Ser, Ala, Val, Leu, Ile, Pro, Phe, Met, or Trp;

(iii) X at position 230 of SEQ ID NO: 65 is Met, Ala, Val, Leu, Ile, Pro, Phe, or Trp; and (iv) X at position 231 of SEQ ID NO: 65 is Gly, Ala, Val, Leu, Ile, Pro, Phe, Met, or Trp;

(q) a β chain comprising the amino acid sequence of SEQ ID NO: 66, wherein X at position 173 of SEQ ID NO: 66 is Ser or Cys;

(r) both (p) and (q);

(s) SEQ ID NO: 67;

(t) SEQ ID NO: 68;

(u) SEQ ID NO: 69;

(v) SEQ ID NO: 70;

(w) both (s) and (t);

(x) both (u) and (v);

(y) an α chain comprising the amino acid sequence of SEQ ID NO: 71, wherein:

(i) X at position 187 of SEQ ID NO: 71 is Thr or Cys;

(ii) X at position 251 of SEQ ID NO: 71 is Ser, Ala, Val, Leu, Ile, Pro, Phe, Met, or Trp;

(iii) X at position 253 of SEQ ID NO: 71 is Met, Ala, Val, Leu, Ile, Pro, Phe, or Trp; and (iv) X at position 254 of SEQ ID NO: 71 is Gly, Ala, Val, Leu, Ile, Pro, Phe, Met, or Trp;

(z) a β chain comprising the amino acid sequence of SEQ ID NO: 72, wherein X at position 191 of SEQ ID NO: 72 is Ser or Cys;

(aa) both (y) and (z);

(bb) an α chain comprising the amino acid sequence of SEQ ID NO: 73, wherein:

(i) X at position 168 of SEQ ID NO: 73 is Thr or Cys;

(ii) X at position 232 of SEQ ID NO: 73 is Ser, Ala, Val, Leu, Ile, Pro, Phe, Met, or Trp;

(iii) X at position 234 of SEQ ID NO: 73 is Met, Ala, Val, Leu, Ile, Pro, Phe, or Trp; and (iv) X at position 235 of SEQ ID NO: 73 is Gly, Ala, Val, Leu, Ile, Pro, Phe, Met, or Trp;

(cc) a β chain comprising the amino acid sequence of SEQ ID NO: 74, wherein X at position 173 of SEQ ID NO: 74 is Ser or Cys;

(dd) both (bb) and (cc);

(ee) SEQ ID NO: 75;

(ff) SEQ ID NO: 76;

(gg) SEQ ID NO: 77;

(hh) SEQ ID NO: 78;

(ii) both (ee) and (ff);

(jj) both (gg) and (hh);

(kk) an α chain comprising the amino acid sequence of SEQ ID NO: 79, wherein:

(i) X at position 175 of SEQ ID NO: 79 is Thr or Cys;

(ii) X at position 239 of SEQ ID NO: 79 is Ser, Ala, Val, Leu, Ile, Pro, Phe, Met, or Trp;

(iii) X at position 241 of SEQ ID NO: 79 is Met, Ala, Val, Leu, Ile, Pro, Phe, or Trp; and (iv) X at position 242 of SEQ ID NO: 79 is Gly, Ala, Val, Leu, Ile, Pro, Phe, Met, or Trp;

(ll) a β chain comprising the amino acid sequence of SEQ ID NO: 80, wherein X at position 190 of SEQ ID NO: 80 is Ser or Cys;

(mm) both (kk) and (ll);

(nn) an α chain comprising the amino acid sequence of SEQ ID NO: 81, wherein:

(i) X at position 159 of SEQ ID NO: 81 is Thr or Cys;

(ii) X at position 223 of SEQ ID NO: 81 is Ser, Ala, Val, Leu, Ile, Pro, Phe, Met, or Trp;

(iii) X at position 225 of SEQ ID NO: 81 is Met, Ala, Val, Leu, Ile, Pro, Phe, or Trp; and (iv) X at position 226 of SEQ ID NO: 81 is Gly, Ala, Val, Leu, Ile, Pro, Phe, Met, or Trp;

(oo) a β chain comprising the amino acid sequence of SEQ ID NO: 82, wherein X at position 172 of SEQ ID NO: 82 is Ser or Cys;

(pp) both (nn) and (oo);

(qq) SEQ ID NO: 83;

(rr) SEQ ID NO: 84;

(ss) SEQ ID NO: 85;

(tt) SEQ ID NO: 86;

(uu) both (qq) and (rr); or (vv) both (ss) and (tt).

15. A recombinant expression vector comprising the nucleic acid according to claim 1.

16. The recombinant expression vector according to claim 15, which is a transposon or a lentiviral vector.

17. A method of producing a host cell expressing a TCR that has antigenic specificity for the peptide of MTEYKLVVVGADGVGKSALTIQLI (SEQ ID NO: 88), the method comprising contacting a cell with the vector according to claim 15 under conditions that allow introduction of the vector into the cell.

18. An isolated or purified host cell comprising the nucleic acid according to claim 1.

19. The host cell according to claim 18, wherein the cell is a human lymphocyte.

20. The host cell according to claim 18, wherein the cell is selected from the group consisting of a T cell, a natural killer T (NKT) cell, an invariant natural killer T (iNKT) cell, and a natural killer (NK) cell.

21. An isolated or purified population of cells comprising the host cell according to claim 18.

22. A pharmaceutical composition comprising (a) the population of cells according to claim 21 and (b) a pharmaceutically acceptable carrier.

23. A method of inducing an immune response against cancer in a mammal, the method comprising administering to the mammal the population of cells according to claim 21 in an amount effective to induce the immune response against cancer in the mammal.

24. A method of treating cancer in a mammal, the method comprising administering to the mammal the population of cells according to claim 21 in an amount effective to treat cancer in the mammal.

25. The method of claim 24, wherein the cancer expresses a mutated human RAS amino acid sequence with a substitution of glycine at position 12 with aspartic acid, wherein the mutated human RAS amino acid sequence is a mutated human Kirsten rat sarcoma viral oncogene homolog (KRAS), a mutated human Harvey rat sarcoma viral oncogene homolog (HRAS), or a mutated human Neuroblastoma rat sarcoma viral oncogene homolog (NRAS) amino acid sequence, and wherein position 12 is defined by reference to the wild-type human KRAS, wild-type human HRAS, or wild-type human NRAS protein, respectively.

26. The method of claim 25, wherein the mutated human RAS amino acid sequence is a mutated human Kirsten rat sarcoma viral oncogene homolog (KRAS) amino acid sequence.

27. The method of claim 25, wherein the mutated human RAS amino acid sequence is a mutated human neuroblastoma rat sarcoma viral oncogene homolog (NRAS) amino acid sequence.

28. The method of claim 25, wherein the mutated human RAS amino acid sequence is a mutated human Harvey rat sarcoma viral oncogene homolog (HRAS) amino acid sequence.

29. The method according to claim 24, wherein the cancer is pancreatic, colorectal, lung, endometrial, ovarian, or prostate cancer.

30. A method of producing a TCR, the method comprising culturing the host cell according to claim 18 so that the TCR is produced.

31. A method of detecting the presence of cancer in mammal, the method comprising:

(a) contacting a sample comprising cells of the cancer with an isolated or purified TCR encoded by the nucleic acid according to claim 1, thereby forming a complex; and (b) detecting the complex, wherein detection of the complex is indicative of the presence of cancer in the mammal.

32. An isolated or purified nucleic acid comprising a nucleotide sequence encoding a protein, wherein the protein comprises:

(a) a first polypeptide chain comprising the amino acid sequences of SEQ ID NOs: 1-3 and a second polypeptide chain comprising the amino acid sequences of SEQ ID NOs: 4-6;

(b) a first polypeptide chain comprising the amino acid sequences of SEQ ID NOs: 11-13 and a second polypeptide chain comprising the amino acid sequences of SEQ ID NOs: 14-16;

(c) a first polypeptide chain comprising the amino acid sequences of SEQ ID NOs: 21-23 and a second polypeptide chain comprising the amino acid sequences of SEQ ID NOs: 24-26; or (d) a first polypeptide chain comprising the amino acid sequences of SEQ ID NOs: 31-33 and a second polypeptide chain comprising the amino acid sequences of SEQ ID NOs: 34-36.

33. The isolated or purified nucleic acid according to claim 32, wherein:

(i) the first polypeptide chain comprises the amino acid sequence of SEQ ID NO: 7 and the second polypeptide chain comprises the amino acid sequence of SEQ ID NO: 8;

(ii) the first polypeptide chain comprises the amino acid sequence of SEQ ID NO: 9 and the second polypeptide chain comprises the amino acid sequence of SEQ ID NO: 10;

(iii) the first polypeptide chain comprises the amino acid sequence of SEQ ID NO: 17 and the second polypeptide chain comprises the amino acid sequence of SEQ ID NO: 18;

(iv) the first polypeptide chain comprises the amino acid sequence of SEQ ID NO: 19 and the second polypeptide chain comprises the amino acid sequence of SEQ ID NO: 20;

(v) the first polypeptide chain comprises the amino acid sequence of SEQ ID NO: 27 and the second polypeptide chain comprises the amino acid sequence of SEQ ID NO: 28;

(vi) the first polypeptide chain comprises the amino acid sequence of SEQ ID NO: 29 and the second polypeptide chain comprises the amino acid sequence of SEQ ID NO: 30;

(vii) the first polypeptide chain comprises the amino acid sequence of SEQ ID NO: 37 and the second polypeptide chain comprises the amino acid sequence of SEQ ID NO: 38; or (viii) the first polypeptide chain comprises the amino acid sequence of SEQ ID NO: 39 and the second polypeptide chain comprises the amino acid sequence of SEQ ID NO: 40.

34. The isolated or purified nucleic acid of claim 32, wherein:

(a) the first polypeptide chain further comprises the amino acid sequence of SEQ ID NO: 49, wherein:
    (i) X at position 48 of SEQ ID NO: 49 is Thr or Cys;
    (ii) X at position 112 of SEQ ID NO: 49 is Ser, Ala, Val, Leu, Ile, Pro, Phe, Met, or Trp;
    (iii) X at position 114 of SEQ ID NO: 49 is Met, Ala, Val, Leu, Ile, Pro, Phe, or Trp; and
    (iv) X at position 115 of SEQ ID NO: 49 is Gly, Ala, Val, Leu, Ile, Pro, Phe, Met, or Trp;

(b) the second polypeptide chain further comprises the amino acid sequence of SEQ ID NO: 50, wherein X at position 57 of SEQ ID NO: 50 is Ser or Cys; or (c) both (a) and (b).

35. The isolated or purified nucleic acid of claim 32, wherein:

(a) the first polypeptide chain comprises the amino acid sequence of SEQ ID NO: 55, wherein:
    (i) X at position 184 of SEQ ID NO: 55 is Thr or Cys;
    (ii) X at position 248 of SEQ ID NO: 55 is Ser, Ala, Val, Leu, Ile, Pro, Phe, Met, or Trp;
    (iii) X at position 250 of SEQ ID NO: 55 is Met, Ala, Val, Leu, Ile, Pro, Phe, or Trp; and
    (iv) X at position 251 of SEQ ID NO: 55 is Gly, Ala, Val, Leu, Ile, Pro, Phe, Met, or Trp;

(b) the second polypeptide chain comprises the amino acid sequence of SEQ ID NO: 56, wherein X at position 199 of SEQ ID NO: 56 is Ser or Cys;

(c) both (a) and (b);

(d) the first polypeptide chain comprises the amino acid sequence of SEQ ID NO: 57, wherein:
    (i) X at position 165 of SEQ ID NO: 57 is Thr or Cys;
    (ii) X at position 229 of SEQ ID NO: 57 is Ser, Ala, Val, Leu, Ile, Pro, Phe, Met, or Trp;
    (iii) X at position 231 of SEQ ID NO: 57 is Met, Ala, Val, Leu, Ile, Pro, Phe, or Trp; and
    (iv) X at position 232 of SEQ ID NO: 57 is Gly, Ala, Val, Leu, Ile, Pro, Phe, Met, or Trp;

(e) the second polypeptide chain comprises the amino acid sequence of SEQ ID NO: 58, wherein X at position 175 of SEQ ID NO: 58 is Ser or Cys;

(f) both (d) and (e);

(g) the first polypeptide chain comprises the amino acid sequence of SEQ ID NO: 59;

(h) the second polypeptide chain comprises the amino acid sequence of SEQ ID NO: 60;
    (i) the first polypeptide chain comprises the amino acid sequence of SEQ ID NO: 61;

(j) the second polypeptide chain comprises the amino acid sequence of SEQ ID NO: 62;

(k) both (g) and (h);

(l) both (i) and (j);

(m) the first polypeptide chain comprises the amino acid sequence of SEQ ID NO: 63, wherein:
    (i) X at position 182 of SEQ ID NO: 63 is Thr or Cys;
    (ii) X at position 246 of SEQ ID NO: 63 is Ser, Ala, Val, Leu, Ile, Pro, Phe, Met, or Trp;
    (iii) X at position 248 of SEQ ID NO: 63 is Met, Ala, Val, Leu, Ile, Pro, Phe, or Trp; and
    (iv) X at position 249 of SEQ ID NO: 63 is Gly, Ala, Val, Leu, Ile, Pro, Phe, Met, or Trp;

(n) the second polypeptide chain comprises the amino acid sequence of SEQ ID NO: 64, wherein X at position 197 of SEQ ID NO: 64 is Ser or Cys;

(o) both (m) and (n);

(p) the first polypeptide chain comprises the amino acid sequence of SEQ ID NO: 65, wherein:
    (i) X at position 164 of SEQ ID NO: 65 is Thr or Cys;
    (ii) X at position 228 of SEQ ID NO: 65 is Ser, Ala, Val, Leu, Ile, Pro, Phe, Met, or Trp;
    (iii) X at position 230 of SEQ ID NO: 65 is Met, Ala, Val, Leu, Ile, Pro, Phe, or Trp; and
    (iv) X at position 231 of SEQ ID NO: 65 is Gly, Ala, Val, Leu, Ile, Pro, Phe, Met, or Trp;

(q) the second polypeptide chain comprises the amino acid sequence of SEQ ID NO: 66, wherein X at position 173 of SEQ ID NO: 66 is Ser or Cys;

(r) both (p) and (q);

(s) the first polypeptide chain comprises the amino acid sequence of SEQ ID NO: 67;

(t) the second polypeptide chain comprises the amino acid sequence of SEQ ID NO: 68;

(u) the first polypeptide chain comprises the amino acid sequence of SEQ ID NO: 69;

(v) the second polypeptide chain comprises the amino acid sequence of SEQ ID NO: 70;

(w) both (s) and (t);

(x) both (u) and (v);

(y) the first polypeptide chain comprises the amino acid sequence of SEQ ID NO: 71, wherein:
    (i) X at position 187 of SEQ ID NO: 71 is Thr or Cys;
    (ii) X at position 251 of SEQ ID NO: 71 is Ser, Ala, Val, Leu, Ile, Pro, Phe, Met, or Trp;
    (iii) X at position 253 of SEQ ID NO: 71 is Met, Ala, Val, Leu, Ile, Pro, Phe, or Trp; and
    (iv) X at position 254 of SEQ ID NO: 71 is Gly, Ala, Val, Leu, Ile, Pro, Phe, Met, or Trp;

(z) the second polypeptide chain comprises the amino acid sequence of SEQ ID NO: 72, wherein X at position 191 of SEQ ID NO: 72 is Ser or Cys;

(aa) both (y) and (z);

(bb) the first polypeptide chain comprises the amino acid sequence of SEQ ID NO: 73, wherein:
    (i) X at position 168 of SEQ ID NO: 73 is Thr or Cys;
    (ii) X at position 232 of SEQ ID NO: 73 is Ser, Ala, Val, Leu, Ile, Pro, Phe, Met, or Trp;
    (iii) X at position 234 of SEQ ID NO: 73 is Met, Ala, Val, Leu, Ile, Pro, Phe, or Trp; and
    (iv) X at position 235 of SEQ ID NO: 73 is Gly, Ala, Val, Leu, Ile, Pro, Phe, Met, or Trp;

(cc) the second polypeptide chain comprises the amino acid sequence of SEQ ID NO: 74, wherein X at position 173 of SEQ ID NO: 74 is Ser or Cys;

(dd) both (bb) and (cc);

(ee) the first polypeptide chain comprises the amino acid sequence of SEQ ID NO: 75;

(ff) the second polypeptide chain comprises the amino acid sequence of SEQ ID NO: 76;

(gg) the first polypeptide chain comprises the amino acid sequence of SEQ ID NO: 77;

(hh) the second polypeptide chain comprises the amino acid sequence of SEQ ID NO: 78;

(ii) both (ee) and (ff);

(jj) both (gg) and (hh);

(kk) the first polypeptide chain comprises the amino acid sequence of SEQ ID NO: 79, wherein:
    (i) X at position 175 of SEQ ID NO: 79 is Thr or Cys;

(ii) X at position 239 of SEQ ID NO: 79 is Ser, Ala, Val, Leu, Ile, Pro, Phe, Met, or Trp;

(iii) X at position 241 of SEQ ID NO: 79 is Met, Ala, Val, Leu, Ile, Pro, Phe, or Trp; and (iv) X at position 242 of SEQ ID NO: 79 is Gly, Ala, Val, Leu, Ile, Pro, Phe, Met, or Trp;

(ll) the second polypeptide chain comprises the amino acid sequence of SEQ ID NO: 80, wherein X at position 190 of SEQ ID NO: 80 is Ser or Cys;

(mm) both (kk) and (ll);

(nn) the first polypeptide chain comprises the amino acid sequence of SEQ ID NO: 81, wherein:

(i) X at position 159 of SEQ ID NO: 81 is Thr or Cys;

(ii) X at position 223 of SEQ ID NO: 81 is Ser, Ala, Val, Leu, Ile, Pro, Phe, Met, or Trp;

(iii) X at position 225 of SEQ ID NO: 81 is Met, Ala, Val, Leu, Ile, Pro, Phe, or Trp; and (iv) X at position 226 of SEQ ID NO: 81 is Gly, Ala, Val, Leu, Ile, Pro, Phe, Met, or Trp;

(oo) the second polypeptide chain comprises the amino acid sequence of SEQ ID NO: 82, wherein X at position 172 of SEQ ID NO: 82 is Ser or Cys;

(pp) both (nn) and (oo);

(qq) the first polypeptide chain comprises the amino acid sequence of SEQ ID NO: 83;

(rr) the second polypeptide chain comprises the amino acid sequence of SEQ ID NO: 84;

(ss) the first polypeptide chain comprises the amino acid sequence of SEQ ID NO: 85;

(tt) the second polypeptide chain comprises the amino acid sequence of SEQ ID NO: 86;

(uu) both (qq) and (rr); or (vv) both (ss) and (tt).

36. An isolated or purified nucleic acid comprising, from 5' to 3', a first nucleotide sequence and a second nucleotide sequence, wherein the first and second nucleotide sequence, respectively, encode the amino sequences of SEQ ID NOs: 7 and 8; 8 and 7; 9 and 10; 10 and 9; 17 and 18; 18 and 17; 19 and 20; 20 and 19; 27 and 28; 28 and 27; 29 and 30; 30 and 29; 37 and 38; 38 and 37; 39 and 40; 40 and 39; 55 and 56; 56 and 55; 57 and 58; 58 and 57; 59 and 60; 60 and 59; 61 and 62; 62 and 61; 63 and 64; 64 and 63; 65 and 66; 66 and 65; 67 and 68; 68 and 67; 69 and 70; 70 and 69; 71 and 72; 72 and 71; 73 and 74; 74 and 73; 75 and 76; 76 and 75; 77 and 78; 78 and 77; 79 and 80; 80 and 79; 81 and 82; 82 and 81; 83 and 84; 84 and 83; 85 and 86; or 86 and 85.

37. The isolated or purified nucleic acid according to claim 36, further comprising a third nucleotide sequence interposed between the first and second nucleotide sequence, wherein the third nucleotide sequence encodes a cleavable linker peptide.

38. The isolated or purified nucleic acid according to claim 37, wherein the cleavable linker peptide comprises the amino acid sequence of

```
                                    (SEQ ID NO: 87)
RAKRSGSGATNFSLLKQAGDVEENPGP.
```

\* \* \* \* \*

SEQUENCE LISTING

```
<160> NUMBER OF SEQ ID NOS: 99

<210> SEQ ID NO 1
<211> LENGTH: 7
<212> TYPE: PRT
<213> ORGANISM: Homo sapiens

<400> SEQUENCE: 1

Thr Ser Asp Gln Ser Tyr Gly
1               5

<210> SEQ ID NO 2
<211> LENGTH: 8
<212> TYPE: PRT
<213> ORGANISM: Homo sapiens

<400> SEQUENCE: 2

Gln Gly Ser Tyr Asp Glu Gln Asn
```

-continued

```
1               5

<210> SEQ ID NO 3
<211> LENGTH: 16
<212> TYPE: PRT
<213> ORGANISM: Homo sapiens

<400> SEQUENCE: 3

Cys Ala Met Arg Glu Gly Pro Arg Gly Gly Gly Asn Lys Leu Thr Phe
1               5                   10                  15

<210> SEQ ID NO 4
<211> LENGTH: 6
<212> TYPE: PRT
<213> ORGANISM: Homo sapiens

<400> SEQUENCE: 4

Asp Phe Gln Ala Thr Thr
1               5

<210> SEQ ID NO 5
<211> LENGTH: 7
<212> TYPE: PRT
<213> ORGANISM: Homo sapiens

<400> SEQUENCE: 5

Ser Asn Glu Gly Ser Lys Ala
1               5

<210> SEQ ID NO 6
<211> LENGTH: 15
<212> TYPE: PRT
<213> ORGANISM: Homo sapiens

<400> SEQUENCE: 6

Cys Ser Ala Asn Pro Ile Ala Ala Asn Ser Tyr Asn Glu Gln Phe
1               5                   10                  15

<210> SEQ ID NO 7
<211> LENGTH: 117
<212> TYPE: PRT
<213> ORGANISM: Homo sapiens

<400> SEQUENCE: 7

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
            20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
    50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Arg Gly Gly Gly Asn Lys Leu Thr Phe Gly Thr Gly Thr Gln
                100                 105                 110

Leu Lys Val Glu Leu
        115
```

<210> SEQ ID NO 8
<211> LENGTH: 118
<212> TYPE: PRT
<213> ORGANISM: Homo sapiens

<400> SEQUENCE: 8

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
            35                  40                  45

Thr Ser Asn Glu Gly Ser Lys Ala Thr Tyr Glu Gln Gly Val Glu Lys
            50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Asn Pro Ile Ala Ala Asn Ser Tyr Asn Glu Gln Phe Phe Gly Pro Gly
                100                 105                 110

Thr Arg Leu Thr Val Leu
        115

<210> SEQ ID NO 9
<211> LENGTH: 136
<212> TYPE: PRT
<213> ORGANISM: Homo sapiens

<400> SEQUENCE: 9

Met Ser Leu Ser Ser Leu Leu Lys Val Val Thr Ala Ser Leu Trp Leu
1               5                   10                  15

Pro Gly Ile Ala Gln Lys Ile Thr Gln Thr Gln Pro Gly Met Phe Val
            20                  25                  30

Gln Glu Lys Glu Ala Val Thr Leu Asp Cys Thr Tyr Asp Thr Ser Asp
        35                  40                  45

Gln Ser Tyr Gly Leu Phe Trp Tyr Lys Gln Pro Ser Ser Gly Glu Met
    50                  55                  60

Ile Phe Leu Ile Tyr Gln Gly Ser Tyr Asp Glu Gln Asn Ala Thr Glu
65                  70                  75                  80

Gly Arg Tyr Ser Leu Asn Phe Gln Lys Ala Arg Lys Ser Ala Asn Leu
                85                  90                  95

Val Ile Ser Ala Ser Gln Leu Gly Asp Ser Ala Met Tyr Phe Cys Ala
                100                 105                 110

Met Arg Glu Gly Pro Arg Gly Gly Gly Asn Lys Leu Thr Phe Gly Thr
            115                 120                 125

Gly Thr Gln Leu Lys Val Glu Leu
        130                 135

<210> SEQ ID NO 10
<211> LENGTH: 142
<212> TYPE: PRT
<213> ORGANISM: Homo sapiens

<400> SEQUENCE: 10

Met Ala Leu Leu Leu Leu Leu Leu Gly Pro Gly Ile Ser Leu Leu Leu
1               5                   10                  15

Pro Gly Ser Leu Gly Ser Gly Leu Gly Ala Val Val Ser Gln His Pro
            20                  25                  30

-continued

```
Ser Trp Val Ile Cys Lys Ser Gly Thr Ser Val Lys Ile Glu Cys Arg
        35                  40                  45

Ser Leu Asp Phe Gln Ala Thr Thr Met Phe Trp Tyr Arg Gln Phe Pro
    50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
            100                 105                 110

Ser Ser Phe Tyr Ile Cys Ser Ala Asn Pro Ile Ala Ala Asn Ser Tyr
        115                 120                 125

Asn Glu Gln Phe Phe Gly Pro Gly Thr Arg Leu Thr Val Leu
    130                 135                 140

<210> SEQ ID NO 11
<211> LENGTH: 6
<212> TYPE: PRT
<213> ORGANISM: Homo sapiens

<400> SEQUENCE: 11

Asp Ser Ala Ser Asn Tyr
1               5

<210> SEQ ID NO 12
<211> LENGTH: 7
<212> TYPE: PRT
<213> ORGANISM: Homo sapiens

<400> SEQUENCE: 12

Ile Arg Ser Asn Val Gly Glu
1               5

<210> SEQ ID NO 13
<211> LENGTH: 16
<212> TYPE: PRT
<213> ORGANISM: Homo sapiens

<400> SEQUENCE: 13

Cys Ala Ala Thr Ser Thr Asp Arg Gly Ser Thr Leu Gly Arg Leu Tyr
1               5                   10                  15

<210> SEQ ID NO 14
<211> LENGTH: 6
<212> TYPE: PRT
<213> ORGANISM: Homo sapiens

<400> SEQUENCE: 14

Asp Phe Gln Ala Thr Thr
1               5

<210> SEQ ID NO 15
<211> LENGTH: 7
<212> TYPE: PRT
<213> ORGANISM: Homo sapiens

<400> SEQUENCE: 15

Ser Asn Glu Gly Ser Lys Ala
1               5

<210> SEQ ID NO 16
```

-continued

```
<211> LENGTH: 13
<212> TYPE: PRT
<213> ORGANISM: Homo sapiens

<400> SEQUENCE: 16

Cys Ser Ala Arg Asp Pro Ala Thr Asn Glu Lys Leu Phe
1               5                   10

<210> SEQ ID NO 17
<211> LENGTH: 116
<212> TYPE: PRT
<213> ORGANISM: Homo sapiens

<400> SEQUENCE: 17

Gly Glu Asn Val Glu Gln His Pro Ser Thr Leu Ser Val Gln Glu Gly
1               5                   10                  15

Asp Ser Ala Val Ile Lys Cys Thr Tyr Ser Asp Ser Ala Ser Asn Tyr
                20                  25                  30

Phe Pro Trp Tyr Lys Gln Glu Leu Gly Lys Gly Pro Gln Leu Ile Ile
            35                  40                  45

Asp Ile Arg Ser Asn Val Gly Glu Lys Lys Asp Gln Arg Ile Ala Val
        50                  55                  60

Thr Leu Asn Lys Thr Ala Lys His Phe Ser Leu His Ile Thr Glu Thr
65                  70                  75                  80

Gln Pro Glu Asp Ser Ala Val Tyr Phe Cys Ala Ala Thr Ser Thr Asp
                85                  90                  95

Arg Gly Ser Thr Leu Gly Arg Leu Tyr Phe Gly Arg Gly Thr Gln Leu
                100                 105                 110

Thr Val Trp Pro
            115

<210> SEQ ID NO 18
<211> LENGTH: 116
<212> TYPE: PRT
<213> ORGANISM: Homo sapiens

<400> SEQUENCE: 18

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
                20                  25                  30

Met Phe Trp Tyr Arg Gln Phe Pro Lys Gln Ser Leu Met Leu Met Ala
            35                  40                  45

Thr Ser Asn Glu Gly Ser Lys Ala Thr Tyr Glu Gln Gly Val Glu Lys
        50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Asp Pro Ala Thr Asn Glu Lys Leu Phe Phe Gly Ser Gly Thr Gln
                100                 105                 110

Leu Ser Val Leu
            115

<210> SEQ ID NO 19
<211> LENGTH: 134
<212> TYPE: PRT
<213> ORGANISM: Homo sapiens
```

```
<400> SEQUENCE: 19

Met Thr Ser Ile Arg Ala Val Phe Ile Phe Leu Trp Leu Gln Leu Asp
1               5                   10                  15

Val Asn Gly Glu Asn Val Glu Gln His Pro Ser Thr Leu Ser Val Gln
                20                  25                  30

Glu Gly Asp Ser Ala Val Ile Lys Cys Thr Tyr Ser Asp Ser Ala Ser
            35                  40                  45

Asn Tyr Phe Pro Trp Tyr Lys Gln Glu Leu Gly Lys Gly Pro Gln Leu
        50                  55                  60

Ile Ile Asp Ile Arg Ser Asn Val Gly Glu Lys Lys Asp Gln Arg Ile
65                  70                  75                  80

Ala Val Thr Leu Asn Lys Thr Ala Lys His Phe Ser Leu His Ile Thr
                85                  90                  95

Glu Thr Gln Pro Glu Asp Ser Ala Val Tyr Phe Cys Ala Ala Thr Ser
            100                 105                 110

Thr Asp Arg Gly Ser Thr Leu Gly Arg Leu Tyr Phe Gly Arg Gly Thr
            115                 120                 125

Gln Leu Thr Val Trp Pro
    130

<210> SEQ ID NO 20
<211> LENGTH: 140
<212> TYPE: PRT
<213> ORGANISM: Homo sapiens

<400> SEQUENCE: 20

Met Ala Leu Leu Leu Leu Leu Leu Gly Pro Gly Ile Ser Leu Leu Leu
1               5                   10                  15

Pro Gly Ser Leu Gly Ser Gly Leu Gly Ala Val Val Ser Gln His Pro
                20                  25                  30

Ser Trp Val Ile Cys Lys Ser Gly Thr Ser Val Lys Ile Glu Cys Arg
            35                  40                  45

Ser Leu Asp Phe Gln Ala Thr Thr Met Phe Trp Tyr Arg Gln Phe Pro
        50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
            100                 105                 110

Ser Ser Phe Tyr Ile Cys Ser Ala Arg Asp Pro Ala Thr Asn Glu Lys
            115                 120                 125

Leu Phe Phe Gly Ser Gly Thr Gln Leu Ser Val Leu
    130                 135                 140

<210> SEQ ID NO 21
<211> LENGTH: 7
<212> TYPE: PRT
<213> ORGANISM: Homo sapiens

<400> SEQUENCE: 21

Thr Arg Asp Thr Thr Tyr Tyr
1               5

<210> SEQ ID NO 22
<211> LENGTH: 8
<212> TYPE: PRT
```

<213> ORGANISM: Homo sapiens

<400> SEQUENCE: 22

Arg Asn Ser Phe Asp Glu Gln Asn
1               5

<210> SEQ ID NO 23
<211> LENGTH: 19
<212> TYPE: PRT
<213> ORGANISM: Homo sapiens

<400> SEQUENCE: 23

Cys Ala Leu Ser Glu Ala Gly Ala Phe Ser Gly Gly Ser Asn Tyr Lys
1               5                   10                  15

Leu Thr Phe

<210> SEQ ID NO 24
<211> LENGTH: 5
<212> TYPE: PRT
<213> ORGANISM: Homo sapiens

<400> SEQUENCE: 24

Ser Gly His Ala Thr
1               5

<210> SEQ ID NO 25
<211> LENGTH: 6
<212> TYPE: PRT
<213> ORGANISM: Homo sapiens

<400> SEQUENCE: 25

Phe Gln Asn Asn Gly Val
1               5

<210> SEQ ID NO 26
<211> LENGTH: 15
<212> TYPE: PRT
<213> ORGANISM: Homo sapiens

<400> SEQUENCE: 26

Cys Ala Ser Ser Leu Ala Leu Gly Gln Gly Asp Thr Glu Ala Phe
1               5                   10                  15

<210> SEQ ID NO 27
<211> LENGTH: 120
<212> TYPE: PRT
<213> ORGANISM: Homo sapiens

<400> SEQUENCE: 27

Ala Gln Lys Val Thr Gln Ala Gln Thr Glu Ile Ser Val Val Glu Lys
1               5                   10                  15

Glu Asp Val Thr Leu Asp Cys Val Tyr Glu Thr Arg Asp Thr Thr Tyr
                20                  25                  30

Tyr Leu Phe Trp Tyr Lys Gln Pro Pro Ser Gly Glu Leu Val Phe Leu
            35                  40                  45

Ile Arg Arg Asn Ser Phe Asp Glu Gln Asn Glu Ile Ser Gly Arg Tyr
        50                  55                  60

Ser Trp Asn Phe Gln Lys Ser Thr Ser Ser Phe Asn Phe Thr Ile Thr
65                  70                  75                  80

Ala Ser Gln Val Val Asp Ser Ala Val Tyr Phe Cys Ala Leu Ser Glu
                85                  90                  95

-continued

```
Ala Gly Ala Phe Ser Gly Gly Ser Asn Tyr Lys Leu Thr Phe Gly Lys
            100                 105                 110

Gly Thr Leu Leu Thr Val Asn Pro
        115                 120

<210> SEQ ID NO 28
<211> LENGTH: 116
<212> TYPE: PRT
<213> ORGANISM: Homo sapiens

<400> SEQUENCE: 28

Glu Ala Gly Val Ala Gln Ser Pro Arg Tyr Lys Ile Ile Glu Lys Arg
1               5                   10                  15

Gln Ser Val Ala Phe Trp Cys Asn Pro Ile Ser Gly His Ala Thr Leu
            20                  25                  30

Tyr Trp Tyr Gln Gln Ile Leu Gly Gln Gly Pro Lys Leu Leu Ile Gln
        35                  40                  45

Phe Gln Asn Asn Gly Val Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Lys Leu Glu Asp Ser Ala Val Tyr Leu Cys Ala Ser Ser Leu
                85                  90                  95

Ala Leu Gly Gln Gly Asp Thr Glu Ala Phe Phe Gly Gln Gly Thr Arg
            100                 105                 110

Leu Thr Val Val
        115

<210> SEQ ID NO 29
<211> LENGTH: 139
<212> TYPE: PRT
<213> ORGANISM: Homo sapiens

<400> SEQUENCE: 29

Met Leu Thr Ala Ser Leu Leu Arg Ala Val Ile Ala Ser Ile Cys Val
1               5                   10                  15

Ser Ser Met Ala Gln Lys Val Thr Gln Ala Gln Thr Glu Ile Ser Val
            20                  25                  30

Val Glu Lys Glu Asp Val Thr Leu Asp Cys Val Tyr Glu Thr Arg Asp
        35                  40                  45

Thr Thr Tyr Tyr Leu Phe Trp Tyr Lys Gln Pro Pro Ser Gly Glu Leu
    50                  55                  60

Val Phe Leu Ile Arg Arg Asn Ser Phe Asp Glu Gln Asn Glu Ile Ser
65                  70                  75                  80

Gly Arg Tyr Ser Trp Asn Phe Gln Lys Ser Thr Ser Ser Phe Asn Phe
                85                  90                  95

Thr Ile Thr Ala Ser Gln Val Val Asp Ser Ala Val Tyr Phe Cys Ala
            100                 105                 110

Leu Ser Glu Ala Gly Ala Phe Ser Gly Gly Ser Asn Tyr Lys Leu Thr
        115                 120                 125

Phe Gly Lys Gly Thr Leu Leu Thr Val Asn Pro
    130                 135

<210> SEQ ID NO 30
<211> LENGTH: 134
<212> TYPE: PRT
<213> ORGANISM: Homo sapiens
```

-continued

```
<400> SEQUENCE: 30

Met Ala Thr Arg Leu Leu Cys Trp Ala Ala Leu Cys Leu Leu Gly Ala
1               5                   10                  15

Leu Thr Glu Ala Gly Val Ala Gln Ser Pro Arg Tyr Lys Ile Ile Glu
            20                  25                  30

Lys Arg Gln Ser Val Ala Phe Trp Cys Asn Pro Ile Ser Gly His Ala
        35                  40                  45

Thr Leu Tyr Trp Tyr Gln Gln Ile Leu Gly Gln Gly Pro Lys Leu Leu
    50                  55                  60

Ile Gln Phe Gln Asn Asn Gly Val Val Asp Asp Ser Gln Leu Pro Lys
65                  70                  75                  80

Asp Arg Phe Ser Ala Glu Arg Leu Lys Gly Val Asp Ser Thr Leu Lys
                85                  90                  95

Ile Gln Pro Ala Lys Leu Glu Asp Ser Ala Val Tyr Leu Cys Ala Ser
            100                 105                 110

Ser Leu Ala Leu Gly Gln Gly Asp Thr Glu Ala Phe Phe Gly Gln Gly
        115                 120                 125

Thr Arg Leu Thr Val Val
    130

<210> SEQ ID NO 31
<211> LENGTH: 6
<212> TYPE: PRT
<213> ORGANISM: Homo sapiens

<400> SEQUENCE: 31

Thr Ser Gly Phe Asn Gly
1               5

<210> SEQ ID NO 32
<211> LENGTH: 6
<212> TYPE: PRT
<213> ORGANISM: Homo sapiens

<400> SEQUENCE: 32

Asn Val Leu Asp Gly Leu
1               5

<210> SEQ ID NO 33
<211> LENGTH: 14
<212> TYPE: PRT
<213> ORGANISM: Homo sapiens

<400> SEQUENCE: 33

Cys Ala Val Phe Ser Ser Gly Ser Ala Arg Gln Leu Thr Phe
1               5                   10

<210> SEQ ID NO 34
<211> LENGTH: 5
<212> TYPE: PRT
<213> ORGANISM: Homo sapiens

<400> SEQUENCE: 34

Leu Gly His Asn Ala
1               5

<210> SEQ ID NO 35
<211> LENGTH: 6
<212> TYPE: PRT
<213> ORGANISM: Homo sapiens
```

```
<400> SEQUENCE: 35

Tyr Asn Phe Lys Glu Gln
1               5

<210> SEQ ID NO 36
<211> LENGTH: 15
<212> TYPE: PRT
<213> ORGANISM: Homo sapiens

<400> SEQUENCE: 36

Cys Ala Ser Ser Gln Ala Trp Gly Gly Ala Asp Gly Glu Leu Phe
1               5                   10                  15

<210> SEQ ID NO 37
<211> LENGTH: 111
<212> TYPE: PRT
<213> ORGANISM: Homo sapiens

<400> SEQUENCE: 37

Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
                20                  25                  30

Phe Trp Tyr Gln Gln His Ala Gly Glu Ala Pro Thr Phe Leu Ser Tyr
            35                  40                  45

Asn Val Leu Asp Gly Leu Glu Glu Lys Gly Arg Phe Ser Ser Phe Leu
    50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Val Phe Ser Ser Gly Ser Ala
                85                  90                  95

Arg Gln Leu Thr Phe Gly Ser Gly Thr Gln Leu Thr Val Leu Pro
                100                 105                 110

<210> SEQ ID NO 38
<211> LENGTH: 115
<212> TYPE: PRT
<213> ORGANISM: Homo sapiens

<400> SEQUENCE: 38

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
                20                  25                  30

Tyr Trp Tyr Lys Gln Ser Ala Lys Lys Pro Leu Glu Leu Met Phe Val
            35                  40                  45

Tyr Asn Phe Lys Glu Gln Thr Glu Asn Asn Ser Val Pro Ser Arg Phe
    50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys Ala Ser Ser Gln Ala
                85                  90                  95

Trp Gly Gly Ala Asp Gly Glu Leu Phe Phe Gly Glu Gly Ser Arg Leu
                100                 105                 110

Thr Val Leu
        115

<210> SEQ ID NO 39
```

```
<211> LENGTH: 127
<212> TYPE: PRT
<213> ORGANISM: Homo sapiens

<400> SEQUENCE: 39

Met Trp Gly Val Phe Leu Leu Tyr Val Ser Met Lys Met Gly Thr Thr
1               5                   10                  15

Gly Gln Asn Ile Asp Gln Pro Thr Glu Met Thr Ala Thr Glu Gly Ala
            20                  25                  30

Ile Val Gln Ile Asn Cys Thr Tyr Gln Thr Ser Gly Phe Asn Gly Leu
            35                  40                  45

Phe Trp Tyr Gln Gln His Ala Gly Glu Ala Pro Thr Phe Leu Ser Tyr
    50                  55                  60

Asn Val Leu Asp Gly Leu Glu Glu Lys Gly Arg Phe Ser Ser Phe Leu
65                  70                  75                  80

Ser Arg Ser Lys Gly Tyr Ser Tyr Leu Leu Leu Lys Glu Leu Gln Met
                85                  90                  95

Lys Asp Ser Ala Ser Tyr Leu Cys Ala Val Phe Ser Ser Gly Ser Ala
            100                 105                 110

Arg Gln Leu Thr Phe Gly Ser Gly Thr Gln Leu Thr Val Leu Pro
            115                 120                 125

<210> SEQ ID NO 40
<211> LENGTH: 133
<212> TYPE: PRT
<213> ORGANISM: Homo sapiens

<400> SEQUENCE: 40

Met Ala Cys Arg Leu Leu Cys Cys Ala Val Leu Cys Leu Leu Gly Ala
1               5                   10                  15

Pro Met Glu Thr Gly Val Thr Gln Thr Pro Arg His Leu Val Met Gly
            20                  25                  30

Met Thr Asn Lys Lys Ser Leu Lys Cys Glu Gln His Leu Gly His Asn
            35                  40                  45

Ala Met Tyr Trp Tyr Lys Gln Ser Ala Lys Lys Pro Leu Glu Leu Met
    50                  55                  60

Phe Val Tyr Asn Phe Lys Glu Gln Thr Glu Asn Asn Ser Val Pro Ser
65                  70                  75                  80

Arg Phe Ser Pro Glu Cys Pro Asn Ser Ser His Leu Phe Leu His Leu
                85                  90                  95

His Thr Leu Gln Pro Glu Asp Ser Ala Leu Tyr Leu Cys Ala Ser Ser
            100                 105                 110

Gln Ala Trp Gly Gly Ala Asp Gly Glu Leu Phe Phe Gly Glu Gly Ser
            115                 120                 125

Arg Leu Thr Val Leu
        130

<210> SEQ ID NO 41
<211> LENGTH: 189
<212> TYPE: PRT
<213> ORGANISM: Homo sapiens

<400> SEQUENCE: 41

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30
```

-continued

```
Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
                180                 185
```

```
<210> SEQ ID NO 42
<211> LENGTH: 188
<212> TYPE: PRT
<213> ORGANISM: Homo sapiens

<400> SEQUENCE: 42
```

```
Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Glu Thr
        130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
                180                 185
```

```
<210> SEQ ID NO 43
<211> LENGTH: 189
<212> TYPE: PRT
<213> ORGANISM: Homo sapiens
```

<400> SEQUENCE: 43

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 44
<211> LENGTH: 189
<212> TYPE: PRT
<213> ORGANISM: Homo sapiens

<400> SEQUENCE: 44

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Ser Lys Ser Phe Ala Asp Ile Asn Leu Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Pro Thr Arg Thr Val Asp Thr Lys
        115                 120                 125

Gln Ala His Glu Leu Ala Lys Ser Tyr Gly Ile Pro Phe Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                165                 170                 175

-continued

```
Gly Thr Gln Gly Cys Met Gly Leu Pro Cys Val Val Met
            180                 185

<210> SEQ ID NO 45
<211> LENGTH: 189
<212> TYPE: PRT
<213> ORGANISM: Homo sapiens

<400> SEQUENCE: 45

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
        130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185

<210> SEQ ID NO 46
<211> LENGTH: 188
<212> TYPE: PRT
<213> ORGANISM: Homo sapiens

<400> SEQUENCE: 46

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125
```

```
Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 47
<211> LENGTH: 189
<212> TYPE: PRT
<213> ORGANISM: Homo sapiens

<400> SEQUENCE: 47

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
                100                 105                 110

Leu Val Gly Asn Lys Cys Asp Leu Ala Ala Arg Thr Val Glu Ser Arg
            115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 48
<211> LENGTH: 189
<212> TYPE: PRT
<213> ORGANISM: Homo sapiens

<400> SEQUENCE: 48

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80
```

-continued

Val Phe Ala Ile Asn Asn Ser Lys Ser Phe Ala Asp Ile Asn Leu Tyr
              85                  90                  95

Arg Glu Gln Ile Lys Arg Val Lys Asp Ser Asp Asp Val Pro Met Val
              100                 105                 110

Leu Val Gly Asn Lys Cys Asp Leu Pro Thr Arg Thr Val Asp Thr Lys
              115                 120                 125

Gln Ala His Glu Leu Ala Lys Ser Tyr Gly Ile Pro Phe Ile Glu Thr
          130                 135                 140

Ser Ala Lys Thr Arg Gln Gly Val Glu Asp Ala Phe Tyr Thr Leu Val
145                 150                 155                 160

Arg Glu Ile Arg Gln Tyr Arg Met Lys Lys Leu Asn Ser Ser Asp Asp
                  165                 170                 175

Gly Thr Gln Gly Cys Met Gly Leu Pro Cys Val Val Met
              180                 185

<210> SEQ ID NO 49
<211> LENGTH: 137
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (48)..(48)
<223> OTHER INFORMATION: X is Thr or Cys
<220> FEATURE:
<221> NAME/KEY: MISC_FEATURE
<222> LOCATION: (112)..(112)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (114)..(114)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (115)..(115)
<223> OTHER INFORMATION: X is Gly, Ala, Val, Leu, Ile, Pro, Phe, Met, or
      Trp

<400> SEQUENCE: 49

Asn Ile Gln Asn Pro Glu Pro Ala Val Tyr Gln Leu Lys Asp Pro Arg
1                 5                   10                  15

Ser Gln Asp Ser Thr Leu Cys Leu Phe Thr Asp Phe Asp Ser Gln Ile
              20                  25                  30

Asn Val Pro Lys Thr Met Glu Ser Gly Thr Phe Ile Thr Asp Lys Xaa
              35                  40                  45

Val Leu Asp Met Lys Ala Met Asp Ser Lys Ser Asn Gly Ala Ile Ala
          50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                  85                  90                  95

Glu Lys Ser Phe Glu Thr Asp Met Asn Leu Asn Phe Gln Asn Leu Xaa
              100                 105                 110

Val Xaa Xaa Leu Arg Ile Leu Leu Leu Lys Val Ala Gly Phe Asn Leu
          115                 120                 125

Leu Met Thr Leu Arg Leu Trp Ser Ser
          130                 135

<210> SEQ ID NO 50

-continued

```
<211> LENGTH: 173
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (57)..(57)
<223> OTHER INFORMATION: X is Ser or Cys

<400> SEQUENCE: 50

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Xaa Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
            115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 51
<211> LENGTH: 137
<212> TYPE: PRT
<213> ORGANISM: Artificial Sequence
<220> FEATURE:
<223> OTHER INFORMATION: Synthetic

<400> SEQUENCE: 51

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Cys
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Leu
            100                 105                 110

Val Ile Val Leu Arg Ile Leu Leu Leu Lys Val Ala Gly Phe Asn Leu
            115                 120                 125
```

-continued

```
Leu Met Thr Leu Arg Leu Trp Ser Ser
    130             135

<210> SEQ ID NO 52
<211> LENGTH: 173
<212> TYPE: PRT
<213> ORGANISM: Artificial Sequence
<220> FEATURE:
<223> OTHER INFORMATION: Synthetic

<400> SEQUENCE: 52

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Cys Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 53
<211> LENGTH: 137
<212> TYPE: PRT
<213> ORGANISM: Mus musculus

<400> SEQUENCE: 53

Asn Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
```

```
        130                 135

<210> SEQ ID NO 54
<211> LENGTH: 173
<212> TYPE: PRT
<213> ORGANISM: Mus musculus

<400> SEQUENCE: 54

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170

<210> SEQ ID NO 55
<211> LENGTH: 273
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (184)..(184)
<223> OTHER INFORMATION: X is Thr or Cys
<220> FEATURE:
<221> NAME/KEY: MISC_FEATURE
<222> LOCATION: (248)..(248)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (250)..(250)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (251)..(251)
<223> OTHER INFORMATION: X is Gly, Ala, Val, Leu, Ile, Pro, Phe, Met, or
     Trp

<400> SEQUENCE: 55

Met Ser Leu Ser Ser Leu Leu Lys Val Val Thr Ala Ser Leu Trp Leu
1               5                   10                  15

Pro Gly Ile Ala Gln Lys Ile Thr Gln Thr Gln Pro Gly Met Phe Val
            20                  25                  30

Gln Glu Lys Glu Ala Val Thr Leu Asp Cys Thr Tyr Asp Thr Ser Asp
            35                  40                  45
```

-continued

```
Gln Ser Tyr Gly Leu Phe Trp Tyr Lys Gln Pro Ser Ser Gly Glu Met
    50                  55                  60

Ile Phe Leu Ile Tyr Gln Gly Ser Tyr Asp Glu Gln Asn Ala Thr Glu
65                  70                  75                  80

Gly Arg Tyr Ser Leu Asn Phe Gln Lys Ala Arg Lys Ser Ala Asn Leu
                85                  90                  95

Val Ile Ser Ala Ser Gln Leu Gly Asp Ser Ala Met Tyr Phe Cys Ala
                100                 105                 110

Met Arg Glu Gly Pro Arg Gly Gly Gly Asn Lys Leu Thr Phe Gly Thr
            115                 120                 125

Gly Thr Gln Leu Lys Val Glu Leu Asn Ile Gln Asn Pro Glu Pro Ala
    130                 135                 140

Val Tyr Gln Leu Lys Asp Pro Arg Ser Gln Asp Ser Thr Leu Cys Leu
145                 150                 155                 160

Phe Thr Asp Phe Asp Ser Gln Ile Asn Val Pro Lys Thr Met Glu Ser
                165                 170                 175

Gly Thr Phe Ile Thr Asp Lys Xaa Val Leu Asp Met Lys Ala Met Asp
                180                 185                 190

Ser Lys Ser Asn Gly Ala Ile Ala Trp Ser Asn Gln Thr Ser Phe Thr
            195                 200                 205

Cys Gln Asp Ile Phe Lys Glu Thr Asn Ala Thr Tyr Pro Ser Ser Asp
    210                 215                 220

Val Pro Cys Asp Ala Thr Leu Thr Glu Lys Ser Phe Glu Thr Asp Met
225                 230                 235                 240

Asn Leu Asn Phe Gln Asn Leu Xaa Val Xaa Xaa Leu Arg Ile Leu Leu
                245                 250                 255

Leu Lys Val Ala Gly Phe Asn Leu Leu Met Thr Leu Arg Leu Trp Ser
            260                 265                 270

Ser
```

```
<210> SEQ ID NO 56
<211> LENGTH: 315
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (199)..(199)
<223> OTHER INFORMATION: X is is Ser or Cys

<400> SEQUENCE: 56
```

```
Met Ala Leu Leu Leu Leu Leu Leu Gly Pro Gly Ile Ser Leu Leu Leu
1               5                   10                  15

Pro Gly Ser Leu Gly Ser Gly Leu Gly Ala Val Val Ser Gln His Pro
                20                  25                  30

Ser Trp Val Ile Cys Lys Ser Gly Thr Ser Val Lys Ile Glu Cys Arg
            35                  40                  45

Ser Leu Asp Phe Gln Ala Thr Thr Met Phe Trp Tyr Arg Gln Phe Pro
    50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
                100                 105                 110
```

-continued

```
Ser Ser Phe Tyr Ile Cys Ser Ala Asn Pro Ile Ala Ala Asn Ser Tyr
        115                 120                 125

Asn Glu Gln Phe Phe Gly Pro Gly Thr Arg Leu Thr Val Leu Glu Asp
    130                 135                 140

Leu Arg Asn Val Thr Pro Pro Lys Val Ser Leu Phe Glu Pro Ser Lys
145                 150                 155                 160

Ala Glu Ile Ala Asn Lys Gln Lys Ala Thr Leu Val Cys Leu Ala Arg
                165                 170                 175

Gly Phe Phe Pro Asp His Val Glu Leu Ser Trp Trp Val Asn Gly Lys
                180                 185                 190

Glu Val His Ser Gly Val Xaa Thr Asp Pro Gln Ala Tyr Lys Glu Ser
        195                 200                 205

Asn Tyr Ser Tyr Cys Leu Ser Ser Arg Leu Arg Val Ser Ala Thr Phe
        210                 215                 220

Trp His Asn Pro Arg Asn His Phe Arg Cys Gln Val Gln Phe His Gly
225                 230                 235                 240

Leu Ser Glu Glu Asp Lys Trp Pro Glu Gly Ser Pro Lys Pro Val Thr
                245                 250                 255

Gln Asn Ile Ser Ala Glu Ala Trp Gly Arg Ala Asp Cys Gly Ile Thr
                260                 265                 270

Ser Ala Ser Tyr Gln Gln Gly Val Leu Ser Ala Thr Ile Leu Tyr Glu
        275                 280                 285

Ile Leu Leu Gly Lys Ala Thr Leu Tyr Ala Val Leu Val Ser Thr Leu
        290                 295                 300

Val Val Met Ala Met Val Lys Arg Lys Asn Ser
305                 310                 315
```

```
<210> SEQ ID NO 57
<211> LENGTH: 254
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (165)..(165)
<223> OTHER INFORMATION: X is Thr or Cys
<220> FEATURE:
<221> NAME/KEY: MISC_FEATURE
<222> LOCATION: (229)..(229)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (231)..(231)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (232)..(232)
<223> OTHER INFORMATION: X is Gly, Ala, Val, Leu, Ile, Pro, Phe, Met, or
     Trp

<400> SEQUENCE: 57

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
                20                  25                  30

Gly Leu Phe Trp Tyr Lys Gln Pro Ser Ser Gly Glu Met Ile Phe Leu
        35                  40                  45

Ile Tyr Gln Gly Ser Tyr Asp Glu Gln Asn Ala Thr Glu Gly Arg Tyr
    50                  55                  60
```

-continued

```
Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Arg Gly Gly Gly Asn Lys Leu Thr Phe Gly Thr Gly Thr Gln
            100                 105                 110

Leu Lys Val Glu Leu Asn Ile Gln Asn Pro Glu Pro Ala Val Tyr Gln
            115                 120                 125

Leu Lys Asp Pro Arg Ser Gln Asp Ser Thr Leu Cys Leu Phe Thr Asp
        130                 135                 140

Phe Asp Ser Gln Ile Asn Val Pro Lys Thr Met Glu Ser Gly Thr Phe
145                 150                 155                 160

Ile Thr Asp Lys Xaa Val Leu Asp Met Lys Ala Met Asp Ser Lys Ser
                165                 170                 175

Asn Gly Ala Ile Ala Trp Ser Asn Gln Thr Ser Phe Thr Cys Gln Asp
            180                 185                 190

Ile Phe Lys Glu Thr Asn Ala Thr Tyr Pro Ser Ser Asp Val Pro Cys
            195                 200                 205

Asp Ala Thr Leu Thr Glu Lys Ser Phe Glu Thr Asp Met Asn Leu Asn
        210                 215                 220

Phe Gln Asn Leu Xaa Val Xaa Xaa Leu Arg Ile Leu Leu Leu Lys Val
225                 230                 235                 240

Ala Gly Phe Asn Leu Leu Met Thr Leu Arg Leu Trp Ser Ser
            245                 250
```

```
<210> SEQ ID NO 58
<211> LENGTH: 291
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (175)..(175)
<223> OTHER INFORMATION: X is Ser or Cys

<400> SEQUENCE: 58
```

```
Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
                20                  25                  30

Met Phe Trp Tyr Arg Gln Phe Pro Lys Gln Ser Leu Met Leu Met Ala
            35                  40                  45

Thr Ser Asn Glu Gly Ser Lys Ala Thr Tyr Glu Gln Gly Val Glu Lys
        50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Asn Pro Ile Ala Ala Asn Ser Tyr Asn Glu Gln Phe Phe Gly Pro Gly
            100                 105                 110

Thr Arg Leu Thr Val Leu Glu Asp Leu Arg Asn Val Thr Pro Pro Lys
            115                 120                 125

Val Ser Leu Phe Glu Pro Ser Lys Ala Glu Ile Ala Asn Lys Gln Lys
        130                 135                 140

Ala Thr Leu Val Cys Leu Ala Arg Gly Phe Phe Pro Asp His Val Glu
```

```
145              150              155              160

Leu Ser Trp Trp Val Asn Gly Lys Glu Val His Ser Gly Val Xaa Thr
             165              170              175

Asp Pro Gln Ala Tyr Lys Glu Ser Asn Tyr Ser Tyr Cys Leu Ser Ser
             180              185              190

Arg Leu Arg Val Ser Ala Thr Phe Trp His Asn Pro Arg Asn His Phe
             195              200              205

Arg Cys Gln Val Gln Phe His Gly Leu Ser Glu Glu Asp Lys Trp Pro
    210              215              220

Glu Gly Ser Pro Lys Pro Val Thr Gln Asn Ile Ser Ala Glu Ala Trp
225              230              235              240

Gly Arg Ala Asp Cys Gly Ile Thr Ser Ala Ser Tyr Gln Gln Gly Val
             245              250              255

Leu Ser Ala Thr Ile Leu Tyr Glu Ile Leu Leu Gly Lys Ala Thr Leu
             260              265              270

Tyr Ala Val Leu Val Ser Thr Leu Val Val Met Ala Met Val Lys Arg
             275              280              285

Lys Asn Ser
    290

<210> SEQ ID NO 59
<211> LENGTH: 273
<212> TYPE: PRT
<213> ORGANISM: Artificial Sequence
<220> FEATURE:
<223> OTHER INFORMATION: Synthetic

<400> SEQUENCE: 59

Met Ser Leu Ser Ser Leu Leu Lys Val Val Thr Ala Ser Leu Trp Leu
1               5               10              15

Pro Gly Ile Ala Gln Lys Ile Thr Gln Thr Gln Pro Gly Met Phe Val
             20              25              30

Gln Glu Lys Glu Ala Val Thr Leu Asp Cys Thr Tyr Asp Thr Ser Asp
    35              40              45

Gln Ser Tyr Gly Leu Phe Trp Tyr Lys Gln Pro Ser Ser Gly Glu Met
    50              55              60

Ile Phe Leu Ile Tyr Gln Gly Ser Tyr Asp Glu Gln Asn Ala Thr Glu
65              70              75              80

Gly Arg Tyr Ser Leu Asn Phe Gln Lys Ala Arg Lys Ser Ala Asn Leu
             85              90              95

Val Ile Ser Ala Ser Gln Leu Gly Asp Ser Ala Met Tyr Phe Cys Ala
             100             105             110

Met Arg Glu Gly Pro Arg Gly Gly Gly Asn Lys Leu Thr Phe Gly Thr
             115             120             125

Gly Thr Gln Leu Lys Val Glu Leu Asn Ile Gln Asn Pro Glu Pro Ala
    130             135             140

Val Tyr Gln Leu Lys Asp Pro Arg Ser Gln Asp Ser Thr Leu Cys Leu
145             150             155             160

Phe Thr Asp Phe Asp Ser Gln Ile Asn Val Pro Lys Thr Met Glu Ser
             165             170             175

Gly Thr Phe Ile Thr Asp Lys Cys Val Leu Asp Met Lys Ala Met Asp
             180             185             190

Ser Lys Ser Asn Gly Ala Ile Ala Trp Ser Asn Gln Thr Ser Phe Thr
             195             200             205

Cys Gln Asp Ile Phe Lys Glu Thr Asn Ala Thr Tyr Pro Ser Ser Asp
```

```
          210               215               220

Val Pro Cys Asp Ala Thr Leu Thr Glu Lys Ser Phe Glu Thr Asp Met
225               230               235               240

Asn Leu Asn Phe Gln Asn Leu Leu Val Ile Val Leu Arg Ile Leu Leu
              245               250               255

Leu Lys Val Ala Gly Phe Asn Leu Leu Met Thr Leu Arg Leu Trp Ser
              260               265               270

Ser

<210> SEQ ID NO 60
<211> LENGTH: 315
<212> TYPE: PRT
<213> ORGANISM: Artificial Sequence
<220> FEATURE:
<223> OTHER INFORMATION: Synthetic

<400> SEQUENCE: 60

Met Ala Leu Leu Leu Leu Leu Leu Gly Pro Gly Ile Ser Leu Leu Leu
1                 5                 10                15

Pro Gly Ser Leu Gly Ser Gly Leu Gly Ala Val Val Ser Gln His Pro
              20                25                30

Ser Trp Val Ile Cys Lys Ser Gly Thr Ser Val Lys Ile Glu Cys Arg
          35                40                45

Ser Leu Asp Phe Gln Ala Thr Thr Met Phe Trp Tyr Arg Gln Phe Pro
      50                55                60

Lys Gln Ser Leu Met Leu Met Ala Thr Ser Asn Glu Gly Ser Lys Ala
65                70                75                80

Thr Tyr Glu Gln Gly Val Glu Lys Asp Lys Phe Leu Ile Asn His Ala
              85                90                95

Ser Leu Thr Leu Ser Thr Leu Thr Val Thr Ser Ala His Pro Glu Asp
              100               105               110

Ser Ser Phe Tyr Ile Cys Ser Ala Asn Pro Ile Ala Ala Asn Ser Tyr
          115               120               125

Asn Glu Gln Phe Phe Gly Pro Gly Thr Arg Leu Thr Val Leu Glu Asp
      130               135               140

Leu Arg Asn Val Thr Pro Pro Lys Val Ser Leu Phe Glu Pro Ser Lys
145               150               155               160

Ala Glu Ile Ala Asn Lys Gln Lys Ala Thr Leu Val Cys Leu Ala Arg
              165               170               175

Gly Phe Phe Pro Asp His Val Glu Leu Ser Trp Trp Val Asn Gly Lys
              180               185               190

Glu Val His Ser Gly Val Cys Thr Asp Pro Gln Ala Tyr Lys Glu Ser
          195               200               205

Asn Tyr Ser Tyr Cys Leu Ser Ser Arg Leu Arg Val Ser Ala Thr Phe
      210               215               220

Trp His Asn Pro Arg Asn His Phe Arg Cys Gln Val Gln Phe His Gly
225               230               235               240

Leu Ser Glu Glu Asp Lys Trp Pro Glu Gly Ser Pro Lys Pro Val Thr
              245               250               255

Gln Asn Ile Ser Ala Glu Ala Trp Gly Arg Ala Asp Cys Gly Ile Thr
          260               265               270

Ser Ala Ser Tyr Gln Gln Gly Val Leu Ser Ala Thr Ile Leu Tyr Glu
          275               280               285

Ile Leu Leu Gly Lys Ala Thr Leu Tyr Ala Val Leu Val Ser Thr Leu
      290               295               300
```

```
Val Val Met Ala Met Val Lys Arg Lys Asn Ser
305             310             315
```

```
<210> SEQ ID NO 61
<211> LENGTH: 254
<212> TYPE: PRT
<213> ORGANISM: Artificial Sequence
<220> FEATURE:
<223> OTHER INFORMATION: Synthetic

<400> SEQUENCE: 61

Ala Gln Lys Ile Thr Gln Thr Gln Pro Gly Met Phe Val Gln Glu Lys
1               5                   10                  15

Glu Ala Val Thr Leu Asp Cys Thr Tyr Asp Thr Ser Asp Gln Ser Tyr
                20                  25                  30

Gly Leu Phe Trp Tyr Lys Gln Pro Ser Ser Gly Glu Met Ile Phe Leu
            35                  40                  45

Ile Tyr Gln Gly Ser Tyr Asp Glu Gln Asn Ala Thr Glu Gly Arg Tyr
        50                  55                  60

Ser Leu Asn Phe Gln Lys Ala Arg Lys Ser Ala Asn Leu Val Ile Ser
65                  70                  75                  80

Ala Ser Gln Leu Gly Asp Ser Ala Met Tyr Phe Cys Ala Met Arg Glu
                85                  90                  95

Gly Pro Arg Gly Gly Gly Asn Lys Leu Thr Phe Gly Thr Gly Thr Gln
            100                 105                 110

Leu Lys Val Glu Leu Asn Ile Gln Asn Pro Glu Pro Ala Val Tyr Gln
            115                 120                 125

Leu Lys Asp Pro Arg Ser Gln Asp Ser Thr Leu Cys Leu Phe Thr Asp
        130                 135                 140

Phe Asp Ser Gln Ile Asn Val Pro Lys Thr Met Glu Ser Gly Thr Phe
145                 150                 155                 160

Ile Thr Asp Lys Cys Val Leu Asp Met Lys Ala Met Asp Ser Lys Ser
            165                 170                 175

Asn Gly Ala Ile Ala Trp Ser Asn Gln Thr Ser Phe Thr Cys Gln Asp
            180                 185                 190

Ile Phe Lys Glu Thr Asn Ala Thr Tyr Pro Ser Ser Asp Val Pro Cys
            195                 200                 205

Asp Ala Thr Leu Thr Glu Lys Ser Phe Glu Thr Asp Met Asn Leu Asn
        210                 215                 220

Phe Gln Asn Leu Leu Val Ile Val Leu Arg Ile Leu Leu Leu Lys Val
225                 230                 235                 240

Ala Gly Phe Asn Leu Leu Met Thr Leu Arg Leu Trp Ser Ser
                245                 250
```

```
<210> SEQ ID NO 62
<211> LENGTH: 291
<212> TYPE: PRT
<213> ORGANISM: Artificial Sequence
<220> FEATURE:
<223> OTHER INFORMATION: Synthetic

<400> SEQUENCE: 62

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
                20                  25                  30

Met Phe Trp Tyr Arg Gln Phe Pro Lys Gln Ser Leu Met Leu Met Ala
```

-continued

```
            35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Asn Pro Ile Ala Ala Asn Ser Tyr Asn Glu Gln Phe Phe Gly Pro Gly
                100                 105                 110

Thr Arg Leu Thr Val Leu Glu Asp Leu Arg Asn Val Thr Pro Pro Lys
                115                 120                 125

Val Ser Leu Phe Glu Pro Ser Lys Ala Glu Ile Ala Asn Lys Gln Lys
    130                 135                 140

Ala Thr Leu Val Cys Leu Ala Arg Gly Phe Phe Pro Asp His Val Glu
145                 150                 155                 160

Leu Ser Trp Trp Val Asn Gly Lys Glu Val His Ser Gly Val Cys Thr
                165                 170                 175

Asp Pro Gln Ala Tyr Lys Glu Ser Asn Tyr Ser Tyr Cys Leu Ser Ser
                180                 185                 190

Arg Leu Arg Val Ser Ala Thr Phe Trp His Asn Pro Arg Asn His Phe
                195                 200                 205

Arg Cys Gln Val Gln Phe His Gly Leu Ser Glu Glu Asp Lys Trp Pro
    210                 215                 220

Glu Gly Ser Pro Lys Pro Val Thr Gln Asn Ile Ser Ala Glu Ala Trp
225                 230                 235                 240

Gly Arg Ala Asp Cys Gly Ile Thr Ser Ala Ser Tyr Gln Gln Gly Val
                245                 250                 255

Leu Ser Ala Thr Ile Leu Tyr Glu Ile Leu Leu Gly Lys Ala Thr Leu
                260                 265                 270

Tyr Ala Val Leu Val Ser Thr Leu Val Val Met Ala Met Val Lys Arg
    275                 280                 285

Lys Asn Ser
    290

<210> SEQ ID NO 63
<211> LENGTH: 271
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (182)..(182)
<223> OTHER INFORMATION: X is Thr or Cys
<220> FEATURE:
<221> NAME/KEY: MISC_FEATURE
<222> LOCATION: (246)..(246)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (248)..(248)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (249)..(249)
<223> OTHER INFORMATION: X is Gly, Ala, Val, Leu, Ile, Pro, Phe, Met, or
     Trp

<400> SEQUENCE: 63

Met Thr Ser Ile Arg Ala Val Phe Ile Phe Leu Trp Leu Gln Leu Asp
```

```
1               5                   10                  15

Val Asn Gly Glu Asn Val Glu Gln His Pro Ser Thr Leu Ser Val Gln
            20                  25                  30

Glu Gly Asp Ser Ala Val Ile Lys Cys Thr Tyr Ser Asp Ser Ala Ser
            35                  40                  45

Asn Tyr Phe Pro Trp Tyr Lys Gln Glu Leu Gly Lys Gly Pro Gln Leu
    50                  55                  60

Ile Ile Asp Ile Arg Ser Asn Val Gly Glu Lys Lys Asp Gln Arg Ile
65                  70                  75                  80

Ala Val Thr Leu Asn Lys Thr Ala Lys His Phe Ser Leu His Ile Thr
                85                  90                  95

Glu Thr Gln Pro Glu Asp Ser Ala Val Tyr Phe Cys Ala Ala Thr Ser
            100                 105                 110

Thr Asp Arg Gly Ser Thr Leu Gly Arg Leu Tyr Phe Gly Arg Gly Thr
            115                 120                 125

Gln Leu Thr Val Trp Pro Asn Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Xaa Val Leu Asp Met Lys Ala Met Asp Ser Lys
            180                 185                 190

Ser Asn Gly Ala Ile Ala Trp Ser Asn Gln Thr Ser Phe Thr Cys Gln
            195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Xaa Val Xaa Xaa Leu Arg Ile Leu Leu Leu Lys
                245                 250                 255

Val Ala Gly Phe Asn Leu Leu Met Thr Leu Arg Leu Trp Ser Ser
            260                 265                 270
```

<210> SEQ ID NO 64
<211> LENGTH: 313
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (197)..(197)
<223> OTHER INFORMATION: X is Ser or Cys

<400> SEQUENCE: 64

```
Met Ala Leu Leu Leu Leu Leu Leu Gly Pro Gly Ile Ser Leu Leu Leu
1               5                   10                  15

Pro Gly Ser Leu Gly Ser Gly Leu Gly Ala Val Val Ser Gln His Pro
            20                  25                  30

Ser Trp Val Ile Cys Lys Ser Gly Thr Ser Val Lys Ile Glu Cys Arg
        35                  40                  45

Ser Leu Asp Phe Gln Ala Thr Thr Met Phe Trp Tyr Arg Gln Phe Pro
    50                  55                  60

Lys Gln Ser Leu Met Leu Met Ala Thr Ser Asn Glu Gly Ser Lys Ala
65                  70                  75                  80
```

```
Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
           100                 105                 110

Ser Ser Phe Tyr Ile Cys Ser Ala Arg Asp Pro Ala Thr Asn Glu Lys
           115                 120                 125

Leu Phe Phe Gly Ser Gly Thr Gln Leu Ser Val Leu Glu Asp Leu Arg
       130                 135                 140

Asn Val Thr Pro Pro Lys Val Ser Leu Phe Glu Pro Ser Lys Ala Glu
145                 150                 155                 160

Ile Ala Asn Lys Gln Lys Ala Thr Leu Val Cys Leu Ala Arg Gly Phe
               165                 170                 175

Phe Pro Asp His Val Glu Leu Ser Trp Trp Val Asn Gly Lys Glu Val
           180                 185                 190

His Ser Gly Val Xaa Thr Asp Pro Gln Ala Tyr Lys Glu Ser Asn Tyr
           195                 200                 205

Ser Tyr Cys Leu Ser Ser Arg Leu Arg Val Ser Ala Thr Phe Trp His
       210                 215                 220

Asn Pro Arg Asn His Phe Arg Cys Gln Val Gln Phe His Gly Leu Ser
225                 230                 235                 240

Glu Glu Asp Lys Trp Pro Glu Gly Ser Pro Lys Pro Val Thr Gln Asn
               245                 250                 255

Ile Ser Ala Glu Ala Trp Gly Arg Ala Asp Cys Gly Ile Thr Ser Ala
               260                 265                 270

Ser Tyr Gln Gln Gly Val Leu Ser Ala Thr Ile Leu Tyr Glu Ile Leu
           275                 280                 285

Leu Gly Lys Ala Thr Leu Tyr Ala Val Leu Val Ser Thr Leu Val Val
       290                 295                 300

Met Ala Met Val Lys Arg Lys Asn Ser
305                 310
```

```
<210> SEQ ID NO 65
<211> LENGTH: 253
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (164)..(164)
<223> OTHER INFORMATION: X is Thr or Cys
<220> FEATURE:
<221> NAME/KEY: MISC_FEATURE
<222> LOCATION: (228)..(228)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (230)..(230)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (231)..(231)
<223> OTHER INFORMATION: X is Gly, Ala, Val, Leu, Ile, Pro, Phe, Met, or
     Trp

<400> SEQUENCE: 65

Gly Glu Asn Val Glu Gln His Pro Ser Thr Leu Ser Val Gln Glu Gly
1               5                   10                  15

Asp Ser Ala Val Ile Lys Cys Thr Tyr Ser Asp Ser Ala Ser Asn Tyr
           20                  25                  30
```

-continued

```
Phe Pro Trp Tyr Lys Gln Glu Leu Gly Lys Gly Pro Gln Leu Ile Ile
        35                  40                  45

Asp Ile Arg Ser Asn Val Gly Glu Lys Lys Asp Gln Arg Ile Ala Val
    50                  55                  60

Thr Leu Asn Lys Thr Ala Lys His Phe Ser Leu His Ile Thr Glu Thr
65                  70                  75                  80

Gln Pro Glu Asp Ser Ala Val Tyr Phe Cys Ala Ala Thr Ser Thr Asp
                85                  90                  95

Arg Gly Ser Thr Leu Gly Arg Leu Tyr Phe Gly Arg Gly Thr Gln Leu
            100                 105                 110

Thr Val Trp Pro Asn Ile Gln Asn Pro Glu Pro Ala Val Tyr Gln Leu
            115                 120                 125

Lys Asp Pro Arg Ser Gln Asp Ser Thr Leu Cys Leu Phe Thr Asp Phe
    130                 135                 140

Asp Ser Gln Ile Asn Val Pro Lys Thr Met Glu Ser Gly Thr Phe Ile
145                 150                 155                 160

Thr Asp Lys Xaa Val Leu Asp Met Lys Ala Met Asp Ser Lys Ser Asn
                165                 170                 175

Gly Ala Ile Ala Trp Ser Asn Gln Thr Ser Phe Thr Cys Gln Asp Ile
            180                 185                 190

Phe Lys Glu Thr Asn Ala Thr Tyr Pro Ser Ser Asp Val Pro Cys Asp
            195                 200                 205

Ala Thr Leu Thr Glu Lys Ser Phe Glu Thr Asp Met Asn Leu Asn Phe
    210                 215                 220

Gln Asn Leu Xaa Val Xaa Xaa Leu Arg Ile Leu Leu Leu Lys Val Ala
225                 230                 235                 240

Gly Phe Asn Leu Leu Met Thr Leu Arg Leu Trp Ser Ser
            245                 250
```

```
<210> SEQ ID NO 66
<211> LENGTH: 289
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (173)..(173)
<223> OTHER INFORMATION: X is Ser or Cys

<400> SEQUENCE: 66
```

```
Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Asp Pro Ala Thr Asn Glu Lys Leu Phe Phe Gly Ser Gly Thr Gln
            100                 105                 110

Leu Ser Val Leu Glu Asp Leu Arg Asn Val Thr Pro Pro Lys Val Ser
            115                 120                 125
```

```
Leu Phe Glu Pro Ser Lys Ala Glu Ile Ala Asn Lys Gln Lys Ala Thr
    130                 135                 140

Leu Val Cys Leu Ala Arg Gly Phe Phe Pro Asp His Val Glu Leu Ser
145                 150                 155                 160

Trp Trp Val Asn Gly Lys Glu Val His Ser Gly Val Xaa Thr Asp Pro
                165                 170                 175

Gln Ala Tyr Lys Glu Ser Asn Tyr Ser Tyr Cys Leu Ser Ser Arg Leu
            180                 185                 190

Arg Val Ser Ala Thr Phe Trp His Asn Pro Arg Asn His Phe Arg Cys
            195                 200                 205

Gln Val Gln Phe His Gly Leu Ser Glu Glu Asp Lys Trp Pro Glu Gly
    210                 215                 220

Ser Pro Lys Pro Val Thr Gln Asn Ile Ser Ala Glu Ala Trp Gly Arg
225                 230                 235                 240

Ala Asp Cys Gly Ile Thr Ser Ala Ser Tyr Gln Gln Gly Val Leu Ser
            245                 250                 255

Ala Thr Ile Leu Tyr Glu Ile Leu Leu Gly Lys Ala Thr Leu Tyr Ala
            260                 265                 270

Val Leu Val Ser Thr Leu Val Val Met Ala Met Val Lys Arg Lys Asn
            275                 280                 285

Ser
```

```
<210> SEQ ID NO 67
<211> LENGTH: 271
<212> TYPE: PRT
<213> ORGANISM: Artificial Sequence
<220> FEATURE:
<223> OTHER INFORMATION: Synthetic

<400> SEQUENCE: 67

Met Thr Ser Ile Arg Ala Val Phe Ile Phe Leu Trp Leu Gln Leu Asp
1               5                   10                  15

Val Asn Gly Glu Asn Val Glu Gln His Pro Ser Thr Leu Ser Val Gln
                20                  25                  30

Glu Gly Asp Ser Ala Val Ile Lys Cys Thr Tyr Ser Asp Ser Ala Ser
            35                  40                  45

Asn Tyr Phe Pro Trp Tyr Lys Gln Glu Leu Gly Lys Gly Pro Gln Leu
    50                  55                  60

Ile Ile Asp Ile Arg Ser Asn Val Gly Glu Lys Lys Asp Gln Arg Ile
65                  70                  75                  80

Ala Val Thr Leu Asn Lys Thr Ala Lys His Phe Ser Leu His Ile Thr
                85                  90                  95

Glu Thr Gln Pro Glu Asp Ser Ala Val Tyr Phe Cys Ala Ala Thr Ser
                100                 105                 110

Thr Asp Arg Gly Ser Thr Leu Gly Arg Leu Tyr Phe Gly Arg Gly Thr
            115                 120                 125

Gln Leu Thr Val Trp Pro Asn Ile Gln Asn Pro Glu Pro Ala Val Tyr
    130                 135                 140

Gln Leu Lys Asp Pro Arg Ser Gln Asp Ser Thr Leu Cys Leu Phe Thr
145                 150                 155                 160

Asp Phe Asp Ser Gln Ile Asn Val Pro Lys Thr Met Glu Ser Gly Thr
                165                 170                 175

Phe Ile Thr Asp Lys Cys Val Leu Asp Met Lys Ala Met Asp Ser Lys
                180                 185                 190
```

```
Ser Asn Gly Ala Ile Ala Trp Ser Asn Gln Thr Ser Phe Thr Cys Gln
        195                 200                 205

Asp Ile Phe Lys Glu Thr Asn Ala Thr Tyr Pro Ser Ser Asp Val Pro
    210                 215                 220

Cys Asp Ala Thr Leu Thr Glu Lys Ser Phe Glu Thr Asp Met Asn Leu
225                 230                 235                 240

Asn Phe Gln Asn Leu Leu Val Ile Val Leu Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 68
<211> LENGTH: 313
<212> TYPE: PRT
<213> ORGANISM: Artificial Sequence
<220> FEATURE:
<223> OTHER INFORMATION: Synthetic

<400> SEQUENCE: 68

Met Ala Leu Leu Leu Leu Leu Leu Gly Pro Gly Ile Ser Leu Leu Leu
1                   5                   10                  15

Pro Gly Ser Leu Gly Ser Gly Leu Gly Ala Val Val Ser Gln His Pro
                20                  25                  30

Ser Trp Val Ile Cys Lys Ser Gly Thr Ser Val Lys Ile Glu Cys Arg
            35                  40                  45

Ser Leu Asp Phe Gln Ala Thr Thr Met Phe Trp Tyr Arg Gln Phe Pro
    50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
                85                  90                  95

Ser Leu Thr Leu Ser Thr Leu Thr Val Thr Ser Ala His Pro Glu Asp
            100                 105                 110

Ser Ser Phe Tyr Ile Cys Ser Ala Arg Asp Pro Ala Thr Asn Glu Lys
        115                 120                 125

Leu Phe Phe Gly Ser Gly Thr Gln Leu Ser Val Leu Glu Asp Leu Arg
    130                 135                 140

Asn Val Thr Pro Pro Lys Val Ser Leu Phe Glu Pro Ser Lys Ala Glu
145                 150                 155                 160

Ile Ala Asn Lys Gln Lys Ala Thr Leu Val Cys Leu Ala Arg Gly Phe
                165                 170                 175

Phe Pro Asp His Val Glu Leu Ser Trp Trp Val Asn Gly Lys Glu Val
            180                 185                 190

His Ser Gly Val Cys Thr Asp Pro Gln Ala Tyr Lys Glu Ser Asn Tyr
        195                 200                 205

Ser Tyr Cys Leu Ser Ser Arg Leu Arg Val Ser Ala Thr Phe Trp His
    210                 215                 220

Asn Pro Arg Asn His Phe Arg Cys Gln Val Gln Phe His Gly Leu Ser
225                 230                 235                 240

Glu Glu Asp Lys Trp Pro Glu Gly Ser Pro Lys Pro Val Thr Gln Asn
                245                 250                 255

Ile Ser Ala Glu Ala Trp Gly Arg Ala Asp Cys Gly Ile Thr Ser Ala
            260                 265                 270

Ser Tyr Gln Gln Gly Val Leu Ser Ala Thr Ile Leu Tyr Glu Ile Leu
        275                 280                 285
```

```
Leu Gly Lys Ala Thr Leu Tyr Ala Val Leu Val Ser Thr Leu Val Val
    290                 295                 300

Met Ala Met Val Lys Arg Lys Asn Ser
305                 310

<210> SEQ ID NO 69
<211> LENGTH: 253
<212> TYPE: PRT
<213> ORGANISM: Artificial Sequence
<220> FEATURE:
<223> OTHER INFORMATION: Synthetic

<400> SEQUENCE: 69

Gly Glu Asn Val Glu Gln His Pro Ser Thr Leu Ser Val Gln Glu Gly
1               5                   10                  15

Asp Ser Ala Val Ile Lys Cys Thr Tyr Ser Asp Ser Ala Ser Asn Tyr
            20                  25                  30

Phe Pro Trp Tyr Lys Gln Glu Leu Gly Lys Gly Pro Gln Leu Ile Ile
        35                  40                  45

Asp Ile Arg Ser Asn Val Gly Glu Lys Lys Asp Gln Arg Ile Ala Val
    50                  55                  60

Thr Leu Asn Lys Thr Ala Lys His Phe Ser Leu His Ile Thr Glu Thr
65                  70                  75                  80

Gln Pro Glu Asp Ser Ala Val Tyr Phe Cys Ala Ala Thr Ser Thr Asp
            85                  90                  95

Arg Gly Ser Thr Leu Gly Arg Leu Tyr Phe Gly Arg Gly Thr Gln Leu
            100                 105                 110

Thr Val Trp Pro Asn Ile Gln Asn Pro Glu Pro Ala Val Tyr Gln Leu
        115                 120                 125

Lys Asp Pro Arg Ser Gln Asp Ser Thr Leu Cys Leu Phe Thr Asp Phe
    130                 135                 140

Asp Ser Gln Ile Asn Val Pro Lys Thr Met Glu Ser Gly Thr Phe Ile
145                 150                 155                 160

Thr Asp Lys Cys Val Leu Asp Met Lys Ala Met Asp Ser Lys Ser Asn
            165                 170                 175

Gly Ala Ile Ala Trp Ser Asn Gln Thr Ser Phe Thr Cys Gln Asp Ile
            180                 185                 190

Phe Lys Glu Thr Asn Ala Thr Tyr Pro Ser Ser Asp Val Pro Cys Asp
        195                 200                 205

Ala Thr Leu Thr Glu Lys Ser Phe Glu Thr Asp Met Asn Leu Asn Phe
    210                 215                 220

Gln Asn Leu Leu Val Ile Val Leu Arg Ile Leu Leu Leu Lys Val Ala
225                 230                 235                 240

Gly Phe Asn Leu Leu Met Thr Leu Arg Leu Trp Ser Ser
            245                 250

<210> SEQ ID NO 70
<211> LENGTH: 289
<212> TYPE: PRT
<213> ORGANISM: Artificial Sequence
<220> FEATURE:
<223> OTHER INFORMATION: Synthetic

<400> SEQUENCE: 70

Gly Ala Val Val Ser Gln His Pro Ser Trp Val Ile Cys Lys Ser Gly
1               5                   10                  15

Thr Ser Val Lys Ile Glu Cys Arg Ser Leu Asp Phe Gln Ala Thr Thr
            20                  25                  30
```

-continued

```
Met Phe Trp Tyr Arg Gln Phe Pro Lys Gln Ser Leu Met Leu Met Ala
        35                  40                  45

Thr Ser Asn Glu Gly Ser Lys Ala Thr Tyr Glu Gln Gly Val Glu Lys
    50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Arg Asp Pro Ala Thr Asn Glu Lys Leu Phe Phe Gly Ser Gly Thr Gln
            100                 105                 110

Leu Ser Val Leu Glu Asp Leu Arg Asn Val Thr Pro Pro Lys Val Ser
            115                 120                 125

Leu Phe Glu Pro Ser Lys Ala Glu Ile Ala Asn Lys Gln Lys Ala Thr
        130                 135                 140

Leu Val Cys Leu Ala Arg Gly Phe Phe Pro Asp His Val Glu Leu Ser
145                 150                 155                 160

Trp Trp Val Asn Gly Lys Glu Val His Ser Gly Val Cys Thr Asp Pro
                165                 170                 175

Gln Ala Tyr Lys Glu Ser Asn Tyr Ser Tyr Cys Leu Ser Ser Arg Leu
            180                 185                 190

Arg Val Ser Ala Thr Phe Trp His Asn Pro Arg Asn His Phe Arg Cys
            195                 200                 205

Gln Val Gln Phe His Gly Leu Ser Glu Glu Asp Lys Trp Pro Glu Gly
        210                 215                 220

Ser Pro Lys Pro Val Thr Gln Asn Ile Ser Ala Glu Ala Trp Gly Arg
225                 230                 235                 240

Ala Asp Cys Gly Ile Thr Ser Ala Ser Tyr Gln Gln Gly Val Leu Ser
                245                 250                 255

Ala Thr Ile Leu Tyr Glu Ile Leu Leu Gly Lys Ala Thr Leu Tyr Ala
                260                 265                 270

Val Leu Val Ser Thr Leu Val Val Met Ala Met Val Lys Arg Lys Asn
            275                 280                 285

Ser
```

```
<210> SEQ ID NO 71
<211> LENGTH: 276
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (187)..(187)
<223> OTHER INFORMATION: X is Thr or Cys
<220> FEATURE:
<221> NAME/KEY: MISC_FEATURE
<222> LOCATION: (251)..(251)
<223> OTHER INFORMATION: X is Ser, Ala, Val, Leu, Ile, Pro, Phe, Met, or
     Trp
<220> FEATURE:
<221> NAME/KEY: MISC_FEATURE
<222> LOCATION: (253)..(253)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (254)..(254)
<223> OTHER INFORMATION: X is Gly, Ala, Val, Leu, Ile, Pro, Phe, Met, or
     Trp

<400> SEQUENCE: 71
```

-continued

```
Met Leu Thr Ala Ser Leu Leu Arg Ala Val Ile Ala Ser Ile Cys Val
1               5                   10                  15

Ser Ser Met Ala Gln Lys Val Thr Gln Ala Gln Thr Glu Ile Ser Val
            20                  25                  30

Val Glu Lys Glu Asp Val Thr Leu Asp Cys Val Tyr Glu Thr Arg Asp
        35                  40                  45

Thr Thr Tyr Tyr Leu Phe Trp Tyr Lys Gln Pro Pro Ser Gly Glu Leu
    50                  55                  60

Val Phe Leu Ile Arg Arg Asn Ser Phe Asp Glu Gln Asn Glu Ile Ser
65                  70                  75                  80

Gly Arg Tyr Ser Trp Asn Phe Gln Lys Ser Thr Ser Ser Phe Asn Phe
                85                  90                  95

Thr Ile Thr Ala Ser Gln Val Val Asp Ser Ala Val Tyr Phe Cys Ala
            100                 105                 110

Leu Ser Glu Ala Gly Ala Phe Ser Gly Gly Ser Asn Tyr Lys Leu Thr
        115                 120                 125

Phe Gly Lys Gly Thr Leu Leu Thr Val Asn Pro Asn Ile Gln Asn Pro
    130                 135                 140

Glu Pro Ala Val Tyr Gln Leu Lys Asp Pro Arg Ser Gln Asp Ser Thr
145                 150                 155                 160

Leu Cys Leu Phe Thr Asp Phe Asp Ser Gln Ile Asn Val Pro Lys Thr
            165                 170                 175

Met Glu Ser Gly Thr Phe Ile Thr Asp Lys Xaa Val Leu Asp Met Lys
        180                 185                 190

Ala Met Asp Ser Lys Ser Asn Gly Ala Ile Ala Trp Ser Asn Gln Thr
        195                 200                 205

Ser Phe Thr Cys Gln Asp Ile Phe Lys Glu Thr Asn Ala Thr Tyr Pro
    210                 215                 220

Ser Ser Asp Val Pro Cys Asp Ala Thr Leu Thr Glu Lys Ser Phe Glu
225                 230                 235                 240

Thr Asp Met Asn Leu Asn Phe Gln Asn Leu Xaa Val Xaa Xaa Leu Arg
            245                 250                 255

Ile Leu Leu Leu Lys Val Ala Gly Phe Asn Leu Leu Met Thr Leu Arg
            260                 265                 270

Leu Trp Ser Ser
        275
```

<210> SEQ ID NO 72
<211> LENGTH: 307
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (191)..(191)
<223> OTHER INFORMATION: X is Ser or Cys

<400> SEQUENCE: 72

```
Met Ala Thr Arg Leu Leu Cys Trp Ala Ala Leu Cys Leu Leu Gly Ala
1               5                   10                  15

Leu Thr Glu Ala Gly Val Ala Gln Ser Pro Arg Tyr Lys Ile Ile Glu
            20                  25                  30

Lys Arg Gln Ser Val Ala Phe Trp Cys Asn Pro Ile Ser Gly His Ala
        35                  40                  45

Thr Leu Tyr Trp Tyr Gln Gln Ile Leu Gly Gln Gly Pro Lys Leu Leu
    50                  55                  60
```

-continued

```
Ile Gln Phe Gln Asn Asn Gly Val Val Asp Asp Ser Gln Leu Pro Lys
65                  70                  75                  80

Asp Arg Phe Ser Ala Glu Arg Leu Lys Gly Val Asp Ser Thr Leu Lys
                85                  90                  95

Ile Gln Pro Ala Lys Leu Glu Asp Ser Ala Val Tyr Leu Cys Ala Ser
                100                 105                 110

Ser Leu Ala Leu Gly Gln Gly Asp Thr Glu Ala Phe Phe Gly Gln Gly
            115                 120                 125

Thr Arg Leu Thr Val Val Glu Asp Leu Arg Asn Val Thr Pro Pro Lys
        130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Xaa Thr
                180                 185                 190

Asp Pro Gln Ala Tyr Lys Glu Ser Asn Tyr Ser Tyr Cys Leu Ser Ser
            195                 200                 205

Arg Leu Arg Val Ser Ala Thr Phe Trp His Asn Pro Arg Asn His Phe
        210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr Gln Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Thr Leu Val Val Met Ala Met Val Lys Arg
        290                 295                 300

Lys Asn Ser
305
```

```
<210> SEQ ID NO 73
<211> LENGTH: 257
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (168)..(168)
<223> OTHER INFORMATION: X is Thr or Cys
<220> FEATURE:
<221> NAME/KEY: MISC_FEATURE
<222> LOCATION: (232)..(232)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (234)..(234)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (235)..(235)
<223> OTHER INFORMATION: X is Gly, Ala, Val, Leu, Ile, Pro, Phe, Met, or
      Trp

<400> SEQUENCE: 73

Ala Gln Lys Val Thr Gln Ala Gln Thr Glu Ile Ser Val Val Glu Lys
1               5                   10                  15
```

-continued

```
Glu Asp Val Thr Leu Asp Cys Val Tyr Glu Thr Arg Asp Thr Thr Tyr
         20              25              30

Tyr Leu Phe Trp Tyr Lys Gln Pro Pro Ser Gly Glu Leu Val Phe Leu
         35              40              45

Ile Arg Arg Asn Ser Phe Asp Glu Gln Asn Glu Ile Ser Gly Arg Tyr
    50              55              60

Ser Trp Asn Phe Gln Lys Ser Thr Ser Ser Phe Asn Phe Thr Ile Thr
65              70              75              80

Ala Ser Gln Val Val Asp Ser Ala Val Tyr Phe Cys Ala Leu Ser Glu
              85              90              95

Ala Gly Ala Phe Ser Gly Gly Ser Asn Tyr Lys Leu Thr Phe Gly Lys
         100             105             110

Gly Thr Leu Leu Thr Val Asn Pro Asn Ile Gln Asn Pro Glu Pro Ala
         115             120             125

Val Tyr Gln Leu Lys Asp Pro Arg Ser Gln Asp Ser Thr Leu Cys Leu
    130             135             140

Phe Thr Asp Phe Asp Ser Gln Ile Asn Val Pro Lys Thr Met Glu Ser
145             150             155             160

Gly Thr Phe Ile Thr Asp Lys Xaa Val Leu Asp Met Lys Ala Met Asp
              165             170             175

Ser Lys Ser Asn Gly Ala Ile Ala Trp Ser Asn Gln Thr Ser Phe Thr
         180             185             190

Cys Gln Asp Ile Phe Lys Glu Thr Asn Ala Thr Tyr Pro Ser Ser Asp
         195             200             205

Val Pro Cys Asp Ala Thr Leu Thr Glu Lys Ser Phe Glu Thr Asp Met
    210             215             220

Asn Leu Asn Phe Gln Asn Leu Xaa Val Xaa Xaa Leu Arg Ile Leu Leu
225             230             235             240

Leu Lys Val Ala Gly Phe Asn Leu Leu Met Thr Leu Arg Leu Trp Ser
              245             250             255

Ser
```

```
<210> SEQ ID NO 74
<211> LENGTH: 289
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (173)..(173)
<223> OTHER INFORMATION: X is Ser or Cys

<400> SEQUENCE: 74
```

```
Glu Ala Gly Val Ala Gln Ser Pro Arg Tyr Lys Ile Ile Glu Lys Arg
1               5               10              15

Gln Ser Val Ala Phe Trp Cys Asn Pro Ile Ser Gly His Ala Thr Leu
         20              25              30

Tyr Trp Tyr Gln Gln Ile Leu Gly Gln Gly Pro Lys Leu Leu Ile Gln
         35              40              45

Phe Gln Asn Asn Gly Val Val Asp Asp Ser Gln Leu Pro Lys Asp Arg
         50              55              60

Phe Ser Ala Glu Arg Leu Lys Gly Val Asp Ser Thr Leu Lys Ile Gln
65              70              75              80

Pro Ala Lys Leu Glu Asp Ser Ala Val Tyr Leu Cys Ala Ser Ser Leu
              85              90              95
```

```
Ala Leu Gly Gln Gly Asp Thr Glu Ala Phe Phe Gly Gln Gly Thr Arg
            100                 105                 110

Leu Thr Val Val Glu Asp Leu Arg Asn Val Thr Pro Pro Lys Val Ser
            115                 120                 125

Leu Phe Glu Pro Ser Lys Ala Glu Ile Ala Asn Lys Gln Lys Ala Thr
            130                 135                 140

Leu Val Cys Leu Ala Arg Gly Phe Phe Pro Asp His Val Glu Leu Ser
145                 150                 155                 160

Trp Trp Val Asn Gly Lys Glu Val His Ser Gly Val Xaa Thr Asp Pro
                165                 170                 175

Gln Ala Tyr Lys Glu Ser Asn Tyr Ser Tyr Cys Leu Ser Ser Arg Leu
                180                 185                 190

Arg Val Ser Ala Thr Phe Trp His Asn Pro Arg Asn His Phe Arg Cys
                195                 200                 205

Gln Val Gln Phe His Gly Leu Ser Glu Glu Asp Lys Trp Pro Glu Gly
            210                 215                 220

Ser Pro Lys Pro Val Thr Gln Asn Ile Ser Ala Glu Ala Trp Gly Arg
225                 230                 235                 240

Ala Asp Cys Gly Ile Thr Ser Ala Ser Tyr Gln Gln Gly Val Leu Ser
                245                 250                 255

Ala Thr Ile Leu Tyr Glu Ile Leu Leu Gly Lys Ala Thr Leu Tyr Ala
                260                 265                 270

Val Leu Val Ser Thr Leu Val Val Met Ala Met Val Lys Arg Lys Asn
            275                 280                 285

Ser
```

```
<210> SEQ ID NO 75
<211> LENGTH: 276
<212> TYPE: PRT
<213> ORGANISM: Artificial Sequence
<220> FEATURE:
<223> OTHER INFORMATION: Synthetic

<400> SEQUENCE: 75

Met Leu Thr Ala Ser Leu Leu Arg Ala Val Ile Ala Ser Ile Cys Val
1                   5                   10                  15

Ser Ser Met Ala Gln Lys Val Thr Gln Ala Gln Thr Glu Ile Ser Val
                20                  25                  30

Val Glu Lys Glu Asp Val Thr Leu Asp Cys Val Tyr Glu Thr Arg Asp
            35                  40                  45

Thr Thr Tyr Tyr Leu Phe Trp Tyr Lys Gln Pro Pro Ser Gly Glu Leu
        50                  55                  60

Val Phe Leu Ile Arg Arg Asn Ser Phe Asp Glu Gln Asn Glu Ile Ser
65                  70                  75                  80

Gly Arg Tyr Ser Trp Asn Phe Gln Lys Ser Thr Ser Ser Phe Asn Phe
                85                  90                  95

Thr Ile Thr Ala Ser Gln Val Val Asp Ser Ala Val Tyr Phe Cys Ala
            100                 105                 110

Leu Ser Glu Ala Gly Ala Phe Ser Gly Gly Ser Asn Tyr Lys Leu Thr
            115                 120                 125

Phe Gly Lys Gly Thr Leu Leu Thr Val Asn Pro Asn Ile Gln Asn Pro
        130                 135                 140

Glu Pro Ala Val Tyr Gln Leu Lys Asp Pro Arg Ser Gln Asp Ser Thr
145                 150                 155                 160
```

Leu Cys Leu Phe Thr Asp Phe Asp Ser Gln Ile Asn Val Pro Lys Thr
                165             170             175

Met Glu Ser Gly Thr Phe Ile Thr Asp Lys Cys Val Leu Asp Met Lys
            180             185             190

Ala Met Asp Ser Lys Ser Asn Gly Ala Ile Ala Trp Ser Asn Gln Thr
            195             200             205

Ser Phe Thr Cys Gln Asp Ile Phe Lys Glu Thr Asn Ala Thr Tyr Pro
        210             215             220

Ser Ser Asp Val Pro Cys Asp Ala Thr Leu Thr Glu Lys Ser Phe Glu
225             230             235             240

Thr Asp Met Asn Leu Asn Phe Gln Asn Leu Leu Val Ile Val Leu Arg
                245             250             255

Ile Leu Leu Leu Lys Val Ala Gly Phe Asn Leu Leu Met Thr Leu Arg
                260             265             270

Leu Trp Ser Ser
            275

<210> SEQ ID NO 76
<211> LENGTH: 307
<212> TYPE: PRT
<213> ORGANISM: Artificial Sequence
<220> FEATURE:
<223> OTHER INFORMATION: Synthetic

<400> SEQUENCE: 76

Met Ala Thr Arg Leu Leu Cys Trp Ala Ala Leu Cys Leu Leu Gly Ala
1               5               10              15

Leu Thr Glu Ala Gly Val Ala Gln Ser Pro Arg Tyr Lys Ile Ile Glu
            20              25              30

Lys Arg Gln Ser Val Ala Phe Trp Cys Asn Pro Ile Ser Gly His Ala
        35              40              45

Thr Leu Tyr Trp Tyr Gln Gln Ile Leu Gly Gln Gly Pro Lys Leu Leu
        50              55              60

Ile Gln Phe Gln Asn Asn Gly Val Val Asp Asp Ser Gln Leu Pro Lys
65              70              75              80

Asp Arg Phe Ser Ala Glu Arg Leu Lys Gly Val Asp Ser Thr Leu Lys
            85              90              95

Ile Gln Pro Ala Lys Leu Glu Asp Ser Ala Val Tyr Leu Cys Ala Ser
            100             105             110

Ser Leu Ala Leu Gly Gln Gly Asp Thr Glu Ala Phe Phe Gly Gln Gly
        115             120             125

Thr Arg Leu Thr Val Val Glu Asp Leu Arg Asn Val Thr Pro Pro Lys
        130             135             140

Val Ser Leu Phe Glu Pro Ser Lys Ala Glu Ile Ala Asn Lys Gln Lys
145             150             155             160

Ala Thr Leu Val Cys Leu Ala Arg Gly Phe Phe Pro Asp His Val Glu
            165             170             175

Leu Ser Trp Trp Val Asn Gly Lys Glu Val His Ser Gly Val Cys Thr
            180             185             190

Asp Pro Gln Ala Tyr Lys Glu Ser Asn Tyr Ser Tyr Cys Leu Ser Ser
        195             200             205

Arg Leu Arg Val Ser Ala Thr Phe Trp His Asn Pro Arg Asn His Phe
        210             215             220

Arg Cys Gln Val Gln Phe His Gly Leu Ser Glu Glu Asp Lys Trp Pro
225             230             235             240

```
Glu Gly Ser Pro Lys Pro Val Thr Gln Asn Ile Ser Ala Glu Ala Trp
            245             250             255

Gly Arg Ala Asp Cys Gly Ile Thr Ser Ala Ser Tyr Gln Gln Gly Val
            260             265             270

Leu Ser Ala Thr Ile Leu Tyr Glu Ile Leu Leu Gly Lys Ala Thr Leu
            275             280             285

Tyr Ala Val Leu Val Ser Thr Leu Val Val Met Ala Met Val Lys Arg
            290             295             300

Lys Asn Ser
305

<210> SEQ ID NO 77
<211> LENGTH: 257
<212> TYPE: PRT
<213> ORGANISM: Artificial Sequence
<220> FEATURE:
<223> OTHER INFORMATION: Synthetic

<400> SEQUENCE: 77

Ala Gln Lys Val Thr Gln Ala Gln Thr Glu Ile Ser Val Val Glu Lys
1               5               10              15

Glu Asp Val Thr Leu Asp Cys Val Tyr Glu Thr Arg Asp Thr Thr Tyr
            20              25              30

Tyr Leu Phe Trp Tyr Lys Gln Pro Pro Ser Gly Glu Leu Val Phe Leu
            35              40              45

Ile Arg Arg Asn Ser Phe Asp Glu Gln Asn Glu Ile Ser Gly Arg Tyr
            50              55              60

Ser Trp Asn Phe Gln Lys Ser Thr Ser Ser Phe Asn Phe Thr Ile Thr
65              70              75              80

Ala Ser Gln Val Val Asp Ser Ala Val Tyr Phe Cys Ala Leu Ser Glu
            85              90              95

Ala Gly Ala Phe Ser Gly Gly Ser Asn Tyr Lys Leu Thr Phe Gly Lys
            100             105             110

Gly Thr Leu Leu Thr Val Asn Pro Asn Ile Gln Asn Pro Glu Pro Ala
            115             120             125

Val Tyr Gln Leu Lys Asp Pro Arg Ser Gln Asp Ser Thr Leu Cys Leu
            130             135             140

Phe Thr Asp Phe Asp Ser Gln Ile Asn Val Pro Lys Thr Met Glu Ser
145             150             155             160

Gly Thr Phe Ile Thr Asp Lys Cys Val Leu Asp Met Lys Ala Met Asp
            165             170             175

Ser Lys Ser Asn Gly Ala Ile Ala Trp Ser Asn Gln Thr Ser Phe Thr
            180             185             190

Cys Gln Asp Ile Phe Lys Glu Thr Asn Ala Thr Tyr Pro Ser Ser Asp
            195             200             205

Val Pro Cys Asp Ala Thr Leu Thr Glu Lys Ser Phe Glu Thr Asp Met
            210             215             220

Asn Leu Asn Phe Gln Asn Leu Leu Val Ile Val Leu Arg Ile Leu Leu
225             230             235             240

Leu Lys Val Ala Gly Phe Asn Leu Leu Met Thr Leu Arg Leu Trp Ser
            245             250             255

Ser

<210> SEQ ID NO 78
<211> LENGTH: 289
<212> TYPE: PRT
```

-continued

```
<213> ORGANISM: Artificial Sequence
<220> FEATURE:
<223> OTHER INFORMATION: Synthetic

<400> SEQUENCE: 78

Glu Ala Gly Val Ala Gln Ser Pro Arg Tyr Lys Ile Ile Glu Lys Arg
1               5                   10                  15

Gln Ser Val Ala Phe Trp Cys Asn Pro Ile Ser Gly His Ala Thr Leu
            20                  25                  30

Tyr Trp Tyr Gln Gln Ile Leu Gly Gln Gly Pro Lys Leu Leu Ile Gln
        35                  40                  45

Phe Gln Asn Asn Gly Val Val Asp Asp Ser Gln Leu Pro Lys Asp Arg
    50                  55                  60

Phe Ser Ala Glu Arg Leu Lys Gly Val Asp Ser Thr Leu Lys Ile Gln
65                  70                  75                  80

Pro Ala Lys Leu Glu Asp Ser Ala Val Tyr Leu Cys Ala Ser Ser Leu
                85                  90                  95

Ala Leu Gly Gln Gly Asp Thr Glu Ala Phe Phe Gly Gln Gly Thr Arg
            100                 105                 110

Leu Thr Val Val Glu Asp Leu Arg Asn Val Thr Pro Pro Lys Val Ser
            115                 120                 125

Leu Phe Glu Pro Ser Lys Ala Glu Ile Ala Asn Lys Gln Lys Ala Thr
    130                 135                 140

Leu Val Cys Leu Ala Arg Gly Phe Phe Pro Asp His Val Glu Leu Ser
145                 150                 155                 160

Trp Trp Val Asn Gly Lys Glu Val His Ser Gly Val Cys Thr Asp Pro
                165                 170                 175

Gln Ala Tyr Lys Glu Ser Asn Tyr Ser Tyr Cys Leu Ser Ser Arg Leu
            180                 185                 190

Arg Val Ser Ala Thr Phe Trp His Asn Pro Arg Asn His Phe Arg Cys
            195                 200                 205

Gln Val Gln Phe His Gly Leu Ser Glu Glu Asp Lys Trp Pro Glu Gly
    210                 215                 220

Ser Pro Lys Pro Val Thr Gln Asn Ile Ser Ala Glu Ala Trp Gly Arg
225                 230                 235                 240

Ala Asp Cys Gly Ile Thr Ser Ala Ser Tyr Gln Gln Gly Val Leu Ser
                245                 250                 255

Ala Thr Ile Leu Tyr Glu Ile Leu Leu Gly Lys Ala Thr Leu Tyr Ala
            260                 265                 270

Val Leu Val Ser Thr Leu Val Val Met Ala Met Val Lys Arg Lys Asn
            275                 280                 285

Ser

<210> SEQ ID NO 79
<211> LENGTH: 264
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (175)..(175)
<223> OTHER INFORMATION: X is Thr or Cys
<220> FEATURE:
<221> NAME/KEY: MISC_FEATURE
<222> LOCATION: (239)..(239)
<223> OTHER INFORMATION: X is Ser, Ala, Val, Leu, Ile, Pro, Phe, Met, or
      Trp
<220> FEATURE:
```

```
<221> NAME/KEY: MISC_FEATURE
<222> LOCATION: (241)..(241)
<223> OTHER INFORMATION: X is Met, Ala, Val, Leu, Ile, Pro, Phe, or Trp
<220> FEATURE:
<221> NAME/KEY: MISC_FEATURE
<222> LOCATION: (242)..(242)
<223> OTHER INFORMATION: X is Gly, Ala, Val, Leu, Ile, Pro, Phe, Met, or
      Trp

<400> SEQUENCE: 79

Met Trp Gly Val Phe Leu Leu Tyr Val Ser Met Lys Met Gly Thr Thr
1               5                   10                  15

Gly Gln Asn Ile Asp Gln Pro Thr Glu Met Thr Ala Thr Glu Gly Ala
                20                  25                  30

Ile Val Gln Ile Asn Cys Thr Tyr Gln Thr Ser Gly Phe Asn Gly Leu
            35                  40                  45

Phe Trp Tyr Gln Gln His Ala Gly Glu Ala Pro Thr Phe Leu Ser Tyr
        50                  55                  60

Asn Val Leu Asp Gly Leu Glu Glu Lys Gly Arg Phe Ser Ser Phe Leu
65                  70                  75                  80

Ser Arg Ser Lys Gly Tyr Ser Tyr Leu Leu Leu Lys Glu Leu Gln Met
                85                  90                  95

Lys Asp Ser Ala Ser Tyr Leu Cys Ala Val Phe Ser Ser Gly Ser Ala
            100                 105                 110

Arg Gln Leu Thr Phe Gly Ser Gly Thr Gln Leu Thr Val Leu Pro Asn
            115                 120                 125

Ile Gln Asn Pro Glu Pro Ala Val Tyr Gln Leu Lys Asp Pro Arg Ser
        130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Xaa Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
            195                 200                 205

Ala Thr Tyr Pro Ser Ser Asp Val Pro Cys Asp Ala Thr Leu Thr Glu
        210                 215                 220

Lys Ser Phe Glu Thr Asp Met Asn Leu Asn Phe Gln Asn Leu Xaa Val
225                 230                 235                 240

Xaa Xaa Leu Arg Ile Leu Leu Leu Lys Val Ala Gly Phe Asn Leu Leu
            245                 250                 255

Met Thr Leu Arg Leu Trp Ser Ser
            260

<210> SEQ ID NO 80
<211> LENGTH: 306
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (190)..(190)
<223> OTHER INFORMATION: X is Ser or Cys

<400> SEQUENCE: 80

Met Ala Cys Arg Leu Leu Cys Cys Ala Val Leu Cys Leu Leu Gly Ala
1               5                   10                  15
```

-continued

```
Pro Met Glu Thr Gly Val Thr Gln Thr Pro Arg His Leu Val Met Gly
            20                  25                  30

Met Thr Asn Lys Lys Ser Leu Lys Cys Glu Gln His Leu Gly His Asn
        35                  40                  45

Ala Met Tyr Trp Tyr Lys Gln Ser Ala Lys Lys Pro Leu Glu Leu Met
    50                  55                  60

Phe Val Tyr Asn Phe Lys Glu Gln Thr Glu Asn Asn Ser Val Pro Ser
65                  70                  75                  80

Arg Phe Ser Pro Glu Cys Pro Asn Ser Ser His Leu Phe Leu His Leu
            85                  90                  95

His Thr Leu Gln Pro Glu Asp Ser Ala Leu Tyr Leu Cys Ala Ser Ser
            100                 105                 110

Gln Ala Trp Gly Gly Ala Asp Gly Glu Leu Phe Phe Gly Glu Gly Ser
        115                 120                 125

Arg Leu Thr Val Leu Glu Asp Leu Arg Asn Val Thr Pro Pro Lys Val
        130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
            165                 170                 175

Ser Trp Trp Val Asn Gly Lys Glu Val His Ser Gly Val Xaa Thr Asp
            180                 185                 190

Pro Gln Ala Tyr Lys Glu Ser Asn Tyr Ser Tyr Cys Leu Ser Ser Arg
        195                 200                 205

Leu Arg Val Ser Ala Thr Phe Trp His Asn Pro Arg Asn His Phe Arg
        210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
    290                 295                 300

Asn Ser
305
```

```
<210> SEQ ID NO 81
<211> LENGTH: 248
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (159)..(159)
<223> OTHER INFORMATION: X is Thr or Cys
<220> FEATURE:
<221> NAME/KEY: MISC_FEATURE
<222> LOCATION: (223)..(223)
<223> OTHER INFORMATION: X is Ser, Ala, Val, Leu, Ile, Pro, Phe, Met, or
      Trp
<220> FEATURE:
<221> NAME/KEY: MISC_FEATURE
<222> LOCATION: (225)..(225)
<223> OTHER INFORMATION: X is Met, Ala, Val, Leu, Ile, Pro, Phe, or Trp
<220> FEATURE:
<221> NAME/KEY: MISC_FEATURE
```

<222> LOCATION: (226)..(226)
<223> OTHER INFORMATION: X is Gly, Ala, Val, Leu, Ile, Pro, Phe, Met, or
      Trp

<400> SEQUENCE: 81

Gly Gln Asn Ile Asp Gln Pro Thr Glu Met Thr Ala Thr Glu Gly Ala
1               5                   10                  15

Ile Val Gln Ile Asn Cys Thr Tyr Gln Thr Ser Gly Phe Asn Gly Leu
                20                  25                  30

Phe Trp Tyr Gln Gln His Ala Gly Glu Ala Pro Thr Phe Leu Ser Tyr
            35                  40                  45

Asn Val Leu Asp Gly Leu Glu Glu Lys Gly Arg Phe Ser Ser Phe Leu
        50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Val Phe Ser Ser Gly Ser Ala
                85                  90                  95

Arg Gln Leu Thr Phe Gly Ser Gly Thr Gln Leu Thr Val Leu Pro Asn
            100                 105                 110

Ile Gln Asn Pro Glu Pro Ala Val Tyr Gln Leu Lys Asp Pro Arg Ser
            115                 120                 125

Gln Asp Ser Thr Leu Cys Leu Phe Thr Asp Phe Asp Ser Gln Ile Asn
    130                 135                 140

Val Pro Lys Thr Met Glu Ser Gly Thr Phe Ile Thr Asp Lys Xaa Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
            195                 200                 205

Lys Ser Phe Glu Thr Asp Met Asn Leu Asn Phe Gln Asn Leu Xaa Val
    210                 215                 220

Xaa Xaa Leu Arg Ile Leu Leu Leu Lys Val Ala Gly Phe Asn Leu Leu
225                 230                 235                 240

Met Thr Leu Arg Leu Trp Ser Ser
                245

<210> SEQ ID NO 82
<211> LENGTH: 288
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (172)..(172)
<223> OTHER INFORMATION: X is Ser or Cys

<400> SEQUENCE: 82

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
                20                  25                  30

Tyr Trp Tyr Lys Gln Ser Ala Lys Lys Pro Leu Glu Leu Met Phe Val
            35                  40                  45

Tyr Asn Phe Lys Glu Gln Thr Glu Asn Asn Ser Val Pro Ser Arg Phe
        50                  55                  60

```
Ser Pro Glu Cys Pro Asn Ser Ser His Leu Phe Leu His Leu His Thr
65                  70                  75                  80

Leu Gln Pro Glu Asp Ser Ala Leu Tyr Leu Cys Ala Ser Ser Gln Ala
                85                  90                  95

Trp Gly Gly Ala Asp Gly Glu Leu Phe Phe Gly Glu Gly Ser Arg Leu
                100                 105                 110

Thr Val Leu Glu Asp Leu Arg Asn Val Thr Pro Pro Lys Val Ser Leu
                115                 120                 125

Phe Glu Pro Ser Lys Ala Glu Ile Ala Asn Lys Gln Lys Ala Thr Leu
    130                 135                 140

Val Cys Leu Ala Arg Gly Phe Phe Pro Asp His Val Glu Leu Ser Trp
145                 150                 155                 160

Trp Val Asn Gly Lys Glu Val His Ser Gly Val Xaa Thr Asp Pro Gln
                165                 170                 175

Ala Tyr Lys Glu Ser Asn Tyr Ser Tyr Cys Leu Ser Ser Arg Leu Arg
                180                 185                 190

Val Ser Ala Thr Phe Trp His Asn Pro Arg Asn His Phe Arg Cys Gln
                195                 200                 205

Val Gln Phe His Gly Leu Ser Glu Glu Asp Lys Trp Pro Glu Gly Ser
    210                 215                 220

Pro Lys Pro Val Thr Gln Asn Ile Ser Ala Glu Ala Trp Gly Arg Ala
225                 230                 235                 240

Asp Cys Gly Ile Thr Ser Ala Ser Tyr Gln Gln Gly Val Leu Ser Ala
                245                 250                 255

Thr Ile Leu Tyr Glu Ile Leu Leu Gly Lys Ala Thr Leu Tyr Ala Val
                260                 265                 270

Leu Val Ser Thr Leu Val Val Met Ala Met Val Lys Arg Lys Asn Ser
                275                 280                 285

<210> SEQ ID NO 83
<211> LENGTH: 264
<212> TYPE: PRT
<213> ORGANISM: Artificial Sequence
<220> FEATURE:
<223> OTHER INFORMATION: Synthetic

<400> SEQUENCE: 83

Met Trp Gly Val Phe Leu Leu Tyr Val Ser Met Lys Met Gly Thr Thr
1                   5                   10                  15

Gly Gln Asn Ile Asp Gln Pro Thr Glu Met Thr Ala Thr Glu Gly Ala
                20                  25                  30

Ile Val Gln Ile Asn Cys Thr Tyr Gln Thr Ser Gly Phe Asn Gly Leu
                35                  40                  45

Phe Trp Tyr Gln Gln His Ala Gly Glu Ala Pro Thr Phe Leu Ser Tyr
    50                  55                  60

Asn Val Leu Asp Gly Leu Glu Glu Lys Gly Arg Phe Ser Ser Phe Leu
65                  70                  75                  80

Ser Arg Ser Lys Gly Tyr Ser Tyr Leu Leu Leu Lys Glu Leu Gln Met
                85                  90                  95

Lys Asp Ser Ala Ser Tyr Leu Cys Ala Val Phe Ser Ser Gly Ser Ala
                100                 105                 110

Arg Gln Leu Thr Phe Gly Ser Gly Thr Gln Leu Thr Val Leu Pro Asn
    115                 120                 125

Ile Gln Asn Pro Glu Pro Ala Val Tyr Gln Leu Lys Asp Pro Arg Ser
    130                 135                 140
```

-continued

```
Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Cys Val
                165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
                195                 200                 205

Ala Thr Tyr Pro Ser Ser Asp Val Pro Cys Asp Ala Thr Leu Thr Glu
            210                 215                 220

Lys Ser Phe Glu Thr Asp Met Asn Leu Asn Phe Gln Asn Leu Leu Val
225                 230                 235                 240

Ile Val Leu Arg Ile Leu Leu Leu Lys Val Ala Gly Phe Asn Leu Leu
                245                 250                 255

Met Thr Leu Arg Leu Trp Ser Ser
                260

<210> SEQ ID NO 84
<211> LENGTH: 306
<212> TYPE: PRT
<213> ORGANISM: Artificial Sequence
<220> FEATURE:
<223> OTHER INFORMATION: Synthetic

<400> SEQUENCE: 84

Met Ala Cys Arg Leu Leu Cys Cys Ala Val Leu Cys Leu Leu Gly Ala
1               5                   10                  15

Pro Met Glu Thr Gly Val Thr Gln Thr Pro Arg His Leu Val Met Gly
            20                  25                  30

Met Thr Asn Lys Lys Ser Leu Lys Cys Glu Gln His Leu Gly His Asn
            35                  40                  45

Ala Met Tyr Trp Tyr Lys Gln Ser Ala Lys Lys Pro Leu Glu Leu Met
    50                  55                  60

Phe Val Tyr Asn Phe Lys Glu Gln Thr Glu Asn Asn Ser Val Pro Ser
65                  70                  75                  80

Arg Phe Ser Pro Glu Cys Pro Asn Ser Ser His Leu Phe Leu His Leu
            85                  90                  95

His Thr Leu Gln Pro Glu Asp Ser Ala Leu Tyr Leu Cys Ala Ser Ser
            100                 105                 110

Gln Ala Trp Gly Gly Ala Asp Gly Glu Leu Phe Phe Gly Glu Gly Ser
            115                 120                 125

Arg Leu Thr Val Leu Glu Asp Leu Arg Asn Val Thr Pro Pro Lys Val
            130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Cys Thr Asp
                180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
            210                 215                 220

Cys Gln Val Gln Phe His Gly Leu Ser Glu Glu Asp Lys Trp Pro Glu
225                 230                 235                 240
```

-continued

```
Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Thr Leu Val Val Met Ala Met Val Lys Arg Lys
        290                 295                 300

Asn Ser
305

<210> SEQ ID NO 85
<211> LENGTH: 248
<212> TYPE: PRT
<213> ORGANISM: Artificial Sequence
<220> FEATURE:
<223> OTHER INFORMATION: Synthetic

<400> SEQUENCE: 85

Gly Gln Asn Ile Asp Gln Pro Thr Glu Met Thr Ala Thr Glu Gly Ala
1                 5                   10                  15

Ile Val Gln Ile Asn Cys Thr Tyr Gln Thr Ser Gly Phe Asn Gly Leu
                20                  25                  30

Phe Trp Tyr Gln Gln His Ala Gly Glu Ala Pro Thr Phe Leu Ser Tyr
        35                  40                  45

Asn Val Leu Asp Gly Leu Glu Glu Lys Gly Arg Phe Ser Ser Phe Leu
        50                  55                  60

Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Val Phe Ser Ser Gly Ser Ala
                85                  90                  95

Arg Gln Leu Thr Phe Gly Ser Gly Thr Gln Leu Thr Val Leu Pro Asn
            100                 105                 110

Ile Gln Asn Pro Glu Pro Ala Val Tyr Gln Leu Lys Asp Pro Arg Ser
        115                 120                 125

Gln Asp Ser Thr Leu Cys Leu Phe Thr Asp Phe Asp Ser Gln Ile Asn
        130                 135                 140

Val Pro Lys Thr Met Glu Ser Gly Thr Phe Ile Thr Asp Lys Cys Val
145                 150                 155                 160

Leu Asp Met Lys Ala Met Asp Ser Lys Ser Asn Gly Ala Ile Ala Trp
                165                 170                 175

Ser Asn Gln Thr Ser Phe Thr Cys Gln Asp Ile Phe Lys Glu Thr Asn
            180                 185                 190

Ala Thr Tyr Pro Ser Ser Asp Val Pro Cys Asp Ala Thr Leu Thr Glu
            195                 200                 205

Lys Ser Phe Glu Thr Asp Met Asn Leu Asn Phe Gln Asn Leu Leu Val
        210                 215                 220

Ile Val Leu Arg Ile Leu Leu Leu Lys Val Ala Gly Phe Asn Leu Leu
225                 230                 235                 240

Met Thr Leu Arg Leu Trp Ser Ser
                245

<210> SEQ ID NO 86
<211> LENGTH: 288
<212> TYPE: PRT
<213> ORGANISM: Artificial Sequence
```

```
<220> FEATURE:
<223> OTHER INFORMATION: Synthetic

<400> SEQUENCE: 86

Glu Thr Gly Val Thr Gln Thr Pro Arg His Leu Val Met Gly Met Thr
1               5                   10                  15

Asn Lys Lys Ser Leu Lys Cys Glu Gln His Leu Gly His Asn Ala Met
            20                  25                  30

Tyr Trp Tyr Lys Gln Ser Ala Lys Lys Pro Leu Glu Leu Met Phe Val
        35                  40                  45

Tyr Asn Phe Lys Glu Gln Thr Glu Asn Asn Ser Val Pro Ser Arg Phe
    50                  55                  60

Ser Pro Glu Cys Pro Asn Ser Ser His Leu Phe Leu His Leu His Thr
65                  70                  75                  80

Leu Gln Pro Glu Asp Ser Ala Leu Tyr Leu Cys Ala Ser Ser Gln Ala
                85                  90                  95

Trp Gly Gly Ala Asp Gly Glu Leu Phe Phe Gly Glu Gly Ser Arg Leu
            100                 105                 110

Thr Val Leu Glu Asp Leu Arg Asn Val Thr Pro Pro Lys Val Ser Leu
        115                 120                 125

Phe Glu Pro Ser Lys Ala Glu Ile Ala Asn Lys Gln Lys Ala Thr Leu
    130                 135                 140

Val Cys Leu Ala Arg Gly Phe Phe Pro Asp His Val Glu Leu Ser Trp
145                 150                 155                 160

Trp Val Asn Gly Lys Glu Val His Ser Gly Val Cys Thr Asp Pro Gln
                165                 170                 175

Ala Tyr Lys Glu Ser Asn Tyr Ser Tyr Cys Leu Ser Ser Arg Leu Arg
            180                 185                 190

Val Ser Ala Thr Phe Trp His Asn Pro Arg Asn His Phe Arg Cys Gln
        195                 200                 205

Val Gln Phe His Gly Leu Ser Glu Glu Asp Lys Trp Pro Glu Gly Ser
    210                 215                 220

Pro Lys Pro Val Thr Gln Asn Ile Ser Ala Glu Ala Trp Gly Arg Ala
225                 230                 235                 240

Asp Cys Gly Ile Thr Ser Ala Ser Tyr Gln Gln Gly Val Leu Ser Ala
                245                 250                 255

Thr Ile Leu Tyr Glu Ile Leu Leu Gly Lys Ala Thr Leu Tyr Ala Val
            260                 265                 270

Leu Val Ser Thr Leu Val Val Met Ala Met Val Lys Arg Lys Asn Ser
        275                 280                 285

<210> SEQ ID NO 87
<211> LENGTH: 27
<212> TYPE: PRT
<213> ORGANISM: Artificial Sequence
<220> FEATURE:
<223> OTHER INFORMATION: Synthetic

<400> SEQUENCE: 87

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 88
<211> LENGTH: 24
<212> TYPE: PRT
```

-continued

<213> ORGANISM: Homo sapiens

<400> SEQUENCE: 88

```
Met Thr Glu Tyr Lys Leu Val Val Val Gly Ala Asp Gly Val Gly Lys
1               5                   10                  15

Ser Ala Leu Thr Ile Gln Leu Ile
            20
```

<210> SEQ ID NO 89
<211> LENGTH: 24
<212> TYPE: PRT
<213> ORGANISM: Homo sapiens

<400> SEQUENCE: 89

```
Met Thr Glu Tyr Lys Leu Val Val Val Gly Ala Gly Gly Val Gly Lys
1               5                   10                  15

Ser Ala Leu Thr Ile Gln Leu Ile
            20
```

<210> SEQ ID NO 90
<211> LENGTH: 23
<212> TYPE: PRT
<213> ORGANISM: Homo sapiens

<400> SEQUENCE: 90

```
Thr Glu Tyr Lys Leu Val Val Val Gly Ala Gly Gly Val Gly Lys Ser
1               5                   10                  15

Ala Leu Thr Ile Gln Leu Ile
            20
```

<210> SEQ ID NO 91
<211> LENGTH: 615
<212> TYPE: PRT
<213> ORGANISM: Artificial Sequence
<220> FEATURE:
<223> OTHER INFORMATION: Synthetic

<400> SEQUENCE: 91

```
Met Ala Leu Leu Leu Leu Leu Leu Gly Pro Gly Ile Ser Leu Leu Leu
1               5                   10                  15

Pro Gly Ser Leu Gly Ser Gly Leu Gly Ala Val Val Ser Gln His Pro
            20                  25                  30

Ser Trp Val Ile Cys Lys Ser Gly Thr Ser Val Lys Ile Glu Cys Arg
        35                  40                  45

Ser Leu Asp Phe Gln Ala Thr Thr Met Phe Trp Tyr Arg Gln Phe Pro
    50                  55                  60

Lys Gln Ser Leu Met Leu Met Ala Thr Ser Asn Glu Gly Ser Lys Ala
65                  70                  75                  80

Thr Tyr Glu Gln Gly Val Glu Lys Asp Lys Phe Leu Ile Asn His Ala
            85                  90                  95

Ser Leu Thr Leu Ser Thr Leu Thr Val Thr Ser Ala His Pro Glu Asp
            100                 105                 110

Ser Ser Phe Tyr Ile Cys Ser Ala Asn Pro Ile Ala Ala Asn Ser Tyr
        115                 120                 125

Asn Glu Gln Phe Phe Gly Pro Gly Thr Arg Leu Thr Val Leu Glu Asp
    130                 135                 140

Leu Arg Asn Val Thr Pro Pro Lys Val Ser Leu Phe Glu Pro Ser Lys
145                 150                 155                 160

Ala Glu Ile Ala Asn Lys Gln Lys Ala Thr Leu Val Cys Leu Ala Arg
```

-continued

```
                165             170             175

Gly Phe Phe Pro Asp His Val Glu Leu Ser Trp Trp Val Asn Gly Lys
            180             185             190

Glu Val His Ser Gly Val Cys Thr Asp Pro Gln Ala Tyr Lys Glu Ser
        195             200             205

Asn Tyr Ser Tyr Cys Leu Ser Ser Arg Leu Arg Val Ser Ala Thr Phe
    210             215             220

Trp His Asn Pro Arg Asn His Phe Arg Cys Gln Val Gln Phe His Gly
225             230             235             240

Leu Ser Glu Glu Asp Lys Trp Pro Glu Gly Ser Pro Lys Pro Val Thr
            245             250             255

Gln Asn Ile Ser Ala Glu Ala Trp Gly Arg Ala Asp Cys Gly Ile Thr
            260             265             270

Ser Ala Ser Tyr Gln Gln Gly Val Leu Ser Ala Thr Ile Leu Tyr Glu
            275             280             285

Ile Leu Leu Gly Lys Ala Thr Leu Tyr Ala Val Leu Val Ser Thr Leu
            290             295             300

Val Val Met Ala Met Val Lys Arg Lys Asn Ser Arg Ala Lys Arg Ser
305             310             315             320

Gly Ser Gly Ala Thr Asn Phe Ser Leu Leu Lys Gln Ala Gly Asp Val
            325             330             335

Glu Glu Asn Pro Gly Pro Met Ser Leu Ser Ser Leu Leu Lys Val Val
            340             345             350

Thr Ala Ser Leu Trp Leu Pro Gly Ile Ala Gln Lys Ile Thr Gln Thr
            355             360             365

Gln Pro Gly Met Phe Val Gln Glu Lys Glu Ala Val Thr Leu Asp Cys
    370             375             380

Thr Tyr Asp Thr Ser Asp Gln Ser Tyr Gly Leu Phe Trp Tyr Lys Gln
385             390             395             400

Pro Ser Ser Gly Glu Met Ile Phe Leu Ile Tyr Gln Gly Ser Tyr Asp
            405             410             415

Glu Gln Asn Ala Thr Glu Gly Arg Tyr Ser Leu Asn Phe Gln Lys Ala
            420             425             430

Arg Lys Ser Ala Asn Leu Val Ile Ser Ala Ser Gln Leu Gly Asp Ser
            435             440             445

Ala Met Tyr Phe Cys Ala Met Arg Glu Gly Pro Arg Gly Gly Gly Asn
    450             455             460

Lys Leu Thr Phe Gly Thr Gly Thr Gln Leu Lys Val Glu Leu Asn Ile
465             470             475             480

Gln Asn Pro Glu Pro Ala Val Tyr Gln Leu Lys Asp Pro Arg Ser Gln
            485             490             495

Asp Ser Thr Leu Cys Leu Phe Thr Asp Phe Asp Ser Gln Ile Asn Val
            500             505             510

Pro Lys Thr Met Glu Ser Gly Thr Phe Ile Thr Asp Lys Cys Val Leu
            515             520             525

Asp Met Lys Ala Met Asp Ser Lys Ser Asn Gly Ala Ile Ala Trp Ser
    530             535             540

Asn Gln Thr Ser Phe Thr Cys Gln Asp Ile Phe Lys Glu Thr Asn Ala
545             550             555             560

Thr Tyr Pro Ser Ser Asp Val Pro Cys Asp Ala Thr Leu Thr Glu Lys
            565             570             575

Ser Phe Glu Thr Asp Met Asn Leu Asn Phe Gln Asn Leu Leu Val Ile
            580             585             590
```

-continued

```
Val Leu Arg Ile Leu Leu Leu Lys Val Ala Gly Phe Asn Leu Leu Met
        595             600             605

Thr Leu Arg Leu Trp Ser Ser
    610             615

<210> SEQ ID NO 92
<211> LENGTH: 611
<212> TYPE: PRT
<213> ORGANISM: Artificial Sequence
<220> FEATURE:
<223> OTHER INFORMATION: Synthetic

<400> SEQUENCE: 92

Met Ala Leu Leu Leu Leu Leu Leu Gly Pro Gly Ile Ser Leu Leu Leu
1               5               10              15

Pro Gly Ser Leu Gly Ser Gly Leu Gly Ala Val Val Ser Gln His Pro
            20              25              30

Ser Trp Val Ile Cys Lys Ser Gly Thr Ser Val Lys Ile Glu Cys Arg
        35              40              45

Ser Leu Asp Phe Gln Ala Thr Thr Met Phe Trp Tyr Arg Gln Phe Pro
    50              55              60

Lys Gln Ser Leu Met Leu Met Ala Thr Ser Asn Glu Gly Ser Lys Ala
65              70              75              80

Thr Tyr Glu Gln Gly Val Glu Lys Asp Lys Phe Leu Ile Asn His Ala
            85              90              95

Ser Leu Thr Leu Ser Thr Leu Thr Val Thr Ser Ala His Pro Glu Asp
            100             105             110

Ser Ser Phe Tyr Ile Cys Ser Ala Arg Asp Pro Ala Thr Asn Glu Lys
        115             120             125

Leu Phe Phe Gly Ser Gly Thr Gln Leu Ser Val Leu Glu Asp Leu Arg
    130             135             140

Asn Val Thr Pro Pro Lys Val Ser Leu Phe Glu Pro Ser Lys Ala Glu
145             150             155             160

Ile Ala Asn Lys Gln Lys Ala Thr Leu Val Cys Leu Ala Arg Gly Phe
            165             170             175

Phe Pro Asp His Val Glu Leu Ser Trp Trp Val Asn Gly Lys Glu Val
            180             185             190

His Ser Gly Val Cys Thr Asp Pro Gln Ala Tyr Lys Glu Ser Asn Tyr
            195             200             205

Ser Tyr Cys Leu Ser Ser Arg Leu Arg Val Ser Ala Thr Phe Trp His
    210             215             220

Asn Pro Arg Asn His Phe Arg Cys Gln Val Gln Phe His Gly Leu Ser
225             230             235             240

Glu Glu Asp Lys Trp Pro Glu Gly Ser Pro Lys Pro Val Thr Gln Asn
            245             250             255

Ile Ser Ala Glu Ala Trp Gly Arg Ala Asp Cys Gly Ile Thr Ser Ala
            260             265             270

Ser Tyr Gln Gln Gly Val Leu Ser Ala Thr Ile Leu Tyr Glu Ile Leu
    275             280             285

Leu Gly Lys Ala Thr Leu Tyr Ala Val Leu Val Ser Thr Leu Val Val
    290             295             300

Met Ala Met Val Lys Arg Lys Asn Ser Arg Ala Lys Arg Ser Gly Ser
305             310             315             320

Gly Ala Thr Asn Phe Ser Leu Leu Lys Gln Ala Gly Asp Val Glu Glu
            325             330             335
```

```
Asn Pro Gly Pro Met Thr Ser Ile Arg Ala Val Phe Ile Phe Leu Trp
        340                 345                 350

Leu Gln Leu Asp Val Asn Gly Glu Asn Val Glu Gln His Pro Ser Thr
        355                 360                 365

Leu Ser Val Gln Glu Gly Asp Ser Ala Val Ile Lys Cys Thr Tyr Ser
        370                 375                 380

Asp Ser Ala Ser Asn Tyr Phe Pro Trp Tyr Lys Gln Glu Leu Gly Lys
385                 390                 395                 400

Gly Pro Gln Leu Ile Ile Asp Ile Arg Ser Asn Val Gly Glu Lys Lys
                405                 410                 415

Asp Gln Arg Ile Ala Val Thr Leu Asn Lys Thr Ala Lys His Phe Ser
                420                 425                 430

Leu His Ile Thr Glu Thr Gln Pro Glu Asp Ser Ala Val Tyr Phe Cys
                435                 440                 445

Ala Ala Thr Ser Thr Asp Arg Gly Ser Thr Leu Gly Arg Leu Tyr Phe
        450                 455                 460

Gly Arg Gly Thr Gln Leu Thr Val Trp Pro Asn Ile Gln Asn Pro Glu
465                 470                 475                 480

Pro Ala Val Tyr Gln Leu Lys Asp Pro Arg Ser Gln Asp Ser Thr Leu
                485                 490                 495

Cys Leu Phe Thr Asp Phe Asp Ser Gln Ile Asn Val Pro Lys Thr Met
                500                 505                 510

Glu Ser Gly Thr Phe Ile Thr Asp Lys Cys Val Leu Asp Met Lys Ala
        515                 520                 525

Met Asp Ser Lys Ser Asn Gly Ala Ile Ala Trp Ser Asn Gln Thr Ser
        530                 535                 540

Phe Thr Cys Gln Asp Ile Phe Lys Glu Thr Asn Ala Thr Tyr Pro Ser
545                 550                 555                 560

Ser Asp Val Pro Cys Asp Ala Thr Leu Thr Glu Lys Ser Phe Glu Thr
                565                 570                 575

Asp Met Asn Leu Asn Phe Gln Asn Leu Leu Val Ile Val Leu Arg Ile
                580                 585                 590

Leu Leu Leu Lys Val Ala Gly Phe Asn Leu Leu Met Thr Leu Arg Leu
        595                 600                 605

Trp Ser Ser
    610

<210> SEQ ID NO 93
<211> LENGTH: 610
<212> TYPE: PRT
<213> ORGANISM: Artificial Sequence
<220> FEATURE:
<223> OTHER INFORMATION: Synthetic

<400> SEQUENCE: 93

Met Ala Thr Arg Leu Leu Cys Trp Ala Ala Leu Cys Leu Leu Gly Ala
1               5                   10                  15

Leu Thr Glu Ala Gly Val Ala Gln Ser Pro Arg Tyr Lys Ile Ile Glu
                20                  25                  30

Lys Arg Gln Ser Val Ala Phe Trp Cys Asn Pro Ile Ser Gly His Ala
        35                  40                  45

Thr Leu Tyr Trp Tyr Gln Gln Ile Leu Gly Gln Gly Pro Lys Leu Leu
        50                  55                  60

Ile Gln Phe Gln Asn Asn Gly Val Val Asp Asp Ser Gln Leu Pro Lys
65                  70                  75                  80
```

```
Asp Arg Phe Ser Ala Glu Arg Leu Lys Gly Val Asp Ser Thr Leu Lys
            85                  90                  95

Ile Gln Pro Ala Lys Leu Glu Asp Ser Ala Val Tyr Leu Cys Ala Ser
            100                 105                 110

Ser Leu Ala Leu Gly Gln Gly Asp Thr Glu Ala Phe Phe Gly Gln Gly
            115                 120                 125

Thr Arg Leu Thr Val Val Glu Asp Leu Arg Asn Val Thr Pro Pro Lys
    130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Cys Thr
                180                 185                 190

Asp Pro Gln Ala Tyr Lys Glu Ser Asn Tyr Ser Tyr Cys Leu Ser Ser
            195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
            245                 250                 255

Gly Arg Ala Asp Cys Gly Ile Thr Ser Ala Ser Tyr Gln Gln Gly Val
            260                 265                 270

Leu Ser Ala Thr Ile Leu Tyr Glu Ile Leu Leu Gly Lys Ala Thr Leu
            275                 280                 285

Tyr Ala Val Leu Val Ser Thr Leu Val Val Met Ala Met Val Lys Arg
    290                 295                 300

Lys Asn Ser Arg Ala Lys Arg Ser Gly Ser Gly Ala Thr Asn Phe Ser
305                 310                 315                 320

Leu Leu Lys Gln Ala Gly Asp Val Glu Glu Asn Pro Gly Pro Met Leu
            325                 330                 335

Thr Ala Ser Leu Leu Arg Ala Val Ile Ala Ser Ile Cys Val Ser Ser
            340                 345                 350

Met Ala Gln Lys Val Thr Gln Ala Gln Thr Glu Ile Ser Val Val Glu
            355                 360                 365

Lys Glu Asp Val Thr Leu Asp Cys Val Tyr Glu Thr Arg Asp Thr Thr
    370                 375                 380

Tyr Tyr Leu Phe Trp Tyr Lys Gln Pro Pro Ser Gly Glu Leu Val Phe
385                 390                 395                 400

Leu Ile Arg Arg Asn Ser Phe Asp Glu Gln Asn Glu Ile Ser Gly Arg
            405                 410                 415

Tyr Ser Trp Asn Phe Gln Lys Ser Thr Ser Ser Phe Asn Phe Thr Ile
            420                 425                 430

Thr Ala Ser Gln Val Val Asp Ser Ala Val Tyr Phe Cys Ala Leu Ser
            435                 440                 445

Glu Ala Gly Ala Phe Ser Gly Gly Ser Asn Tyr Lys Leu Thr Phe Gly
    450                 455                 460

Lys Gly Thr Leu Leu Thr Val Asn Pro Asn Ile Gln Asn Pro Glu Pro
465                 470                 475                 480

Ala Val Tyr Gln Leu Lys Asp Pro Arg Ser Gln Asp Ser Thr Leu Cys
            485                 490                 495
```

-continued

```
Leu Phe Thr Asp Phe Asp Ser Gln Ile Asn Val Pro Lys Thr Met Glu
        500             505             510

Ser Gly Thr Phe Ile Thr Asp Lys Cys Val Leu Asp Met Lys Ala Met
        515             520             525

Asp Ser Lys Ser Asn Gly Ala Ile Ala Trp Ser Asn Gln Thr Ser Phe
        530             535             540

Thr Cys Gln Asp Ile Phe Lys Glu Thr Asn Ala Thr Tyr Pro Ser Ser
545             550             555             560

Asp Val Pro Cys Asp Ala Thr Leu Thr Glu Lys Ser Phe Glu Thr Asp
            565             570             575

Met Asn Leu Asn Phe Gln Asn Leu Leu Val Ile Val Leu Arg Ile Leu
        580             585             590

Leu Leu Lys Val Ala Gly Phe Asn Leu Leu Met Thr Leu Arg Leu Trp
        595             600             605

Ser Ser
    610

<210> SEQ ID NO 94
<211> LENGTH: 597
<212> TYPE: PRT
<213> ORGANISM: Artificial Sequence
<220> FEATURE:
<223> OTHER INFORMATION: Synthetic

<400> SEQUENCE: 94

Met Ala Cys Arg Leu Leu Cys Cys Ala Val Leu Cys Leu Leu Gly Ala
1               5               10              15

Pro Met Glu Thr Gly Val Thr Gln Thr Pro Arg His Leu Val Met Gly
        20              25              30

Met Thr Asn Lys Lys Ser Leu Lys Cys Glu Gln His Leu Gly His Asn
        35              40              45

Ala Met Tyr Trp Tyr Lys Gln Ser Ala Lys Lys Pro Leu Glu Leu Met
        50              55              60

Phe Val Tyr Asn Phe Lys Glu Gln Thr Glu Asn Asn Ser Val Pro Ser
65              70              75              80

Arg Phe Ser Pro Glu Cys Pro Asn Ser Ser His Leu Phe Leu His Leu
            85              90              95

His Thr Leu Gln Pro Glu Asp Ser Ala Leu Tyr Leu Cys Ala Ser Ser
        100             105             110

Gln Ala Trp Gly Gly Ala Asp Gly Glu Leu Phe Phe Gly Glu Gly Ser
        115             120             125

Arg Leu Thr Val Leu Glu Asp Leu Arg Asn Val Thr Pro Pro Lys Val
        130             135             140

Ser Leu Phe Glu Pro Ser Lys Ala Glu Ile Ala Asn Lys Gln Lys Ala
145             150             155             160

Thr Leu Val Cys Leu Ala Arg Gly Phe Phe Pro Asp His Val Glu Leu
            165             170             175

Ser Trp Trp Val Asn Gly Lys Glu Val His Ser Gly Val Cys Thr Asp
            180             185             190

Pro Gln Ala Tyr Lys Glu Ser Asn Tyr Ser Tyr Cys Leu Ser Ser Arg
        195             200             205

Leu Arg Val Ser Ala Thr Phe Trp His Asn Pro Arg Asn His Phe Arg
        210             215             220

Cys Gln Val Gln Phe His Gly Leu Ser Glu Glu Asp Lys Trp Pro Glu
225             230             235             240
```

```
Gly Ser Pro Lys Pro Val Thr Gln Asn Ile Ser Ala Glu Ala Trp Gly
            245                 250                 255

Arg Ala Asp Cys Gly Ile Thr Ser Ala Ser Tyr Gln Gln Gly Val Leu
            260                 265                 270

Ser Ala Thr Ile Leu Tyr Glu Ile Leu Leu Gly Lys Ala Thr Leu Tyr
            275                 280                 285

Ala Val Leu Val Ser Thr Leu Val Val Met Ala Met Val Lys Arg Lys
            290                 295                 300

Asn Ser Arg Ala Lys Arg Ser Gly Ser Gly Ala Thr Asn Phe Ser Leu
305                 310                 315                 320

Leu Lys Gln Ala Gly Asp Val Glu Glu Asn Pro Gly Pro Met Trp Gly
            325                 330                 335

Val Phe Leu Leu Tyr Val Ser Met Lys Met Gly Thr Thr Gly Gln Asn
            340                 345                 350

Ile Asp Gln Pro Thr Glu Met Thr Ala Thr Glu Gly Ala Ile Val Gln
            355                 360                 365

Ile Asn Cys Thr Tyr Gln Thr Ser Gly Phe Asn Gly Leu Phe Trp Tyr
            370                 375                 380

Gln Gln His Ala Gly Glu Ala Pro Thr Phe Leu Ser Tyr Asn Val Leu
385                 390                 395                 400

Asp Gly Leu Glu Glu Lys Gly Arg Phe Ser Ser Phe Leu Ser Arg Ser
            405                 410                 415

Lys Gly Tyr Ser Tyr Leu Leu Leu Lys Glu Leu Gln Met Lys Asp Ser
            420                 425                 430

Ala Ser Tyr Leu Cys Ala Val Phe Ser Ser Gly Ser Ala Arg Gln Leu
            435                 440                 445

Thr Phe Gly Ser Gly Thr Gln Leu Thr Val Leu Pro Asn Ile Gln Asn
            450                 455                 460

Pro Glu Pro Ala Val Tyr Gln Leu Lys Asp Pro Arg Ser Gln Asp Ser
465                 470                 475                 480

Thr Leu Cys Leu Phe Thr Asp Phe Asp Ser Gln Ile Asn Val Pro Lys
            485                 490                 495

Thr Met Glu Ser Gly Thr Phe Ile Thr Asp Lys Cys Val Leu Asp Met
            500                 505                 510

Lys Ala Met Asp Ser Lys Ser Asn Gly Ala Ile Ala Trp Ser Asn Gln
            515                 520                 525

Thr Ser Phe Thr Cys Gln Asp Ile Phe Lys Glu Thr Asn Ala Thr Tyr
            530                 535                 540

Pro Ser Ser Asp Val Pro Cys Asp Ala Thr Leu Thr Glu Lys Ser Phe
545                 550                 555                 560

Glu Thr Asp Met Asn Leu Asn Phe Gln Asn Leu Leu Val Ile Val Leu
            565                 570                 575

Arg Ile Leu Leu Leu Lys Val Ala Gly Phe Asn Leu Leu Met Thr Leu
            580                 585                 590

Arg Leu Trp Ser Ser
            595

<210> SEQ ID NO 95
<211> LENGTH: 1848
<212> TYPE: DNA
<213> ORGANISM: Artificial Sequence
<220> FEATURE:
<223> OTHER INFORMATION: Synthetic

<400> SEQUENCE: 95
```

```
atggcactgc tgctgctgct gctgggacct ggaatcagcc tgctgctgcc aggctctctg      60
ggaagcggcc tgggagcagt ggtgagccag cacccatcct gggtcatctg caagtccggc     120
acctctgtga agatcgagtg tcggagcctg gacttccagg ccaccacaat gttctggtac     180
agacagtttc ccaagcagtc cctgatgctg atggccacat ctaatgaggg cagcaaggcc     240
acctatgagc agggcgtgga gaaggataag ttcctgatca accacgcctc cctgaccctg     300
tctaccctga cagtgacctc cgcccaccca gaggacagcc cctttttacat ctgctccgcc     360 aatcccatcg ccgccaactc ttataatgag cagttctttg gaccaggaac aaggctgacc     420
gtgctggagg acctgagaaa tgtgacaccc cctaaggtgt ctctgttcga gccaagcaag     480
gccgagatcg ccaacaagca gaaggccacc ctggtgtgcc tggccagggg cttctttccc     540
gatcacgtgg agctgtcttg gtgggtgaat ggcaaggagg tgcacagcgg cgtgtgcaca     600
gaccctcagg cctacaagga gagcaactac tcctattgtc tgtctagccg gctgagagtg     660
agcgccacct tttggcacaa ccctcggaat cacttcagat gccaggtgca gtttcacggc     720
ctgagcgagg aggataagtg gccagagggc tccccaaagc cagtgaccca gaatatctct     780
gccgaggcat ggggaagggc agactgtgga atcacaagcg cctcctatca gcagggcgtg     840
ctgtccgcca ccatcctgta cgagatcctg ctgggcaagg ccacactgta tgccgtgctg     900
gtgtctaccc tggtggtcat ggctatggtg aagagaaaga atagcagggc caagcggagc     960
ggaagcggag caacaaactt ctccctgctg aagcaggcag cgatgtggac ggagaaccct    1020
ggaccaatga gcctgtcctc tctgctgaag gtggtgaccg cctccctgtg gctgccagga    1080
atcgcacaga agatcacaca gacccagcct ggcatgtttg tgcaggagaa ggaggccgtg    1140
acactggact gcacatacga cacctctgat cagagctacg gcctgttctg gtataagcag    1200
cctagctccg gcgagatgat ctttctgatc taccagggca gctatgatga gcagaacgcc    1260
accgagggca ggtacagcct gaatttccag aaggcccgca gtccgccaa cctggtcatc    1320 tccgcctctc agctgggcga ctccgccatg tatttctgtg caatgaggga gggacccaga    1380
ggcggaggaa ataagctgac atttggcaca ggcacccagc tgaaggtgga gctgaacatc    1440
cagaatcccg agcctgccgt gtaccagctg aaggacccca gatcccagga ttctacactg    1500
tgcctgttca ccgactttga ttcccagatc aacgtgccta agacaatgga gtctggcaca    1560
ttcatcaccg acaagtgcgt gctggacatg aaggctatgg acagcaagtc caacggcgcc    1620
atcgcctgga gcaatcagac atccttcacc tgccaggata tctttaagga gacaaacgcc    1680
acctatccat ctagcgacgt gccctgtgat gccacactga ccgagaagag cttcgagaca    1740
gacatgaacc tgaattttca gaatctgctg gtcatcgtgc tgaggatcct gctgctgaag    1800
gtggccggct ttaacctgct gatgacactg cgcctgtggt cctcttga             1848
```

<210> SEQ ID NO 96
<211> LENGTH: 1836
<212> TYPE: DNA
<213> ORGANISM: Artificial Sequence
<220> FEATURE:
<223> OTHER INFORMATION: Synthetic

<400> SEQUENCE: 96

```
atggcactgc tgctgctgct gctgggacct ggaatcagcc tgctgctgcc aggctctctg      60
ggaagcggcc tgggagcagt ggtgagccag cacccatcct gggtcatctg caagtccggc     120
acctctgtga agatcgagtg taggtccctg gatttccagg ccaccacaat gttctggtac     180
cgccagtttc ccaagcagtc tctgatgctg atggccacat ctaacgaggg cagcaaggcc     240
```

```
acctatgagc agggcgtgga gaaggacaag ttcctgatca atcacgcctc cctgaccctg        300
tctaccctga cagtgacctc tgcccaccca gaggatagct cctttacat ctgcagcgcc        360 agggaccccg ccacaaacga gaagctgttc tttggctctg gcacccagct gagcgtgctg       420
gaggacctgc gcaacgtgac accccctaag gtgtccctgt tcgagccatc taaggccgag        480
atcgccaata agcagaaggc caccctggtg tgcctggccc ggggcttctt tcccgatcac        540
gtggagctgt cttggtgggt gaacggcaag gaggtgcaca cgcggcgtgtg cacagaccct       600 caggcctaca aggagagcaa ttactcctat tgtctgtcta gccggctgag agtgtccgcc        660 acctttggc acaaccccg gaatcacttc agatgccagg tgcagtttca cggcctgtct        720
gaggaggata gtggcctga gggcagccca aagccagtga cccagaacat ctccgccgag        780
gcatggggaa gggcagactg tggcatcaca tctgccagct atcagcaggg cgtgctgagc       840
gccaccatcc tgtacgagat cctgctgggc aaggccacac tgtatgccgt gctggtgtcc        900
accctggtgg tcatggctat ggtgaagcgg aagaactcta gggccaagcg gagcggatct       960
ggagccacaa atttcagcct gctgaagcag gcaggcgatg tggaggagaa ccctggacca       1020
atgacctcca tcagagccgt gttcatcttt ctgtggctgc agctggacgt gaacggcgag       1080
aatgtggagc agcacccctc tacactgagc gtgcaggagg gcgatagcgc cgtgatcaag       1140
tgcacctaca gcgactccgc ctctaattac tttccctggt ataagcagga gctgggcaag       1200
ggccctcagc tgatcatcga tatccggtcc aacgtgggcg agaagaagga ccagagaatc       1260
gccgtgacac tgaataagac cgccaagcac ttcagcctgc acatcacaga gacacagcct       1320
gaggattccg ccgtgtactt ttgtgccgcc acaagcaccg cagggggctc cacactgggc       1380
aggctgtatt tcggaagggg aacacagctg accgtgtggc ctaacatcca gaatcccgag       1440
cctgccgtgt accagctgaa ggaccccacgc tcccaggatt ctacactgtg cctgttcacc       1500
gactttgatt cccagatcaa cgtgcccaag acaatggagt ctggcacctt catcaccgac       1560
aagtgcgtgc tggacatgaa ggctatggac agcaagtcca acggcgccat cgcctggagc       1620
aatcagacat ccttcacctg ccaggatatc tttaaggaga caaatgccac ctatccatcc       1680
tctgacgtgc cctgtgatgc cacactgacc gagaagagct cgagacaga catgaacctg       1740 aatttttcaga acctgctggt catcgtgctg cggatcctgc tgctgaaggt ggccggcttc       1800
aatctgctga tgaccctgag actgtggagc tcctga                                  1836
```

```
<210> SEQ ID NO 97
<211> LENGTH: 1833
<212> TYPE: DNA
<213> ORGANISM: Artificial Sequence
<220> FEATURE:
<223> OTHER INFORMATION: Synthetic

<400> SEQUENCE: 97
```

```
atggccacca ggctgctgtg ctgggccgcc ctgtgcctgc tgggcgccct gacagaggca         60
ggagtggcac agagcccaag gtacaagatc atcgagaagc gccagagcgt ggccttctgg       120
tgcaacccaa tctccggaca cgccaccctg tactggtatc agcagatcct gggccagggc       180
cctaagctgc tgatccagtt ccagaacaat ggcgtggtgg acgattctca gctgccaaag       240
gatcggttta gcgccgagag actgaagggc gtggactcta ccctgaagat ccagccagcc       300
aagctggagg atagcgccgt gtatctgtgc gccagctccc tggccctggg acagggcgac       360
accgaggcct tctttggaca gggaaccagg ctgacagtgg tggaggatct gagaaacgtg       420
```

```
acacccccta aggtgtccct gttcgagcca tctaaggccg agatcgccaa taagcagaag      480
gccaccctgg tgtgcctggc ccggggcttc tttccagacc acgtggagct gtcttggtgg      540
gtgaacggca aggaggtgca cagcggcgtg tgcaccgatc ctcaggccta caaggagagc      600
aattactcct attgtctgtc tagcaggctg cgcgtgagcg ccacattttg gcacaacccc      660
aggaatcact tccgctgcca ggtgcagttt cacggcctgt ctgaggagga caagtggcct      720
gagggcagcc ctaagccagt gacccagaac atctccgccg aggcatgggg aagagcagat      780
tgtggcatca ccagcgcctc ctatcagcag ggcgtgctgt ccgccacaat cctgtacgag      840
atcctgctgg gcaaggccac cctgtatgcc gtgctggtgt ccacactggt ggtcatggct      900
atggtgaaga ggaagaactc tcgggccaag agatctggaa gcggagcaac caatttttcc      960
ctgctgaagc aggcaggcga cgtggaggag aatccaggac ctatgctgac agcctccctg     1020
ctgagggccg tgatcgcctc tatctgcgtg tcctctatgg cccagaaggt gacccaggcc     1080
cagacagaga tcagcgtggt gggagaaggag gacgtgaccc tggattgcgt gtacgagaca     1140
cgggacacca catactatct gttctggtat aagcagccac ccagcggcga gctggtgttc     1200
ctgatccgga gaaactcctt tgatgagcag aatgagatca gcggcagata tcctggaac      1260 tttcagaaga gcaccagcag cttcaacttc accatcacag ccagccaggt ggtggactcc     1320
gccgtgtact tctgtgcact gtccgaggca ggagcctttt ctggaggaag caactataag     1380
ctgacattcg gcaagggcac cctgctgaca gtgaacccca atatccagaa tccagagccc     1440
gccgtgtatc agctgaagga ccctcggtcc caggattcta ccctgtgcct gttcacagac     1500
tttgattccc agatcaacgt gcccaagaca atggagtctg gcacctttat cacagacaag     1560
tgcgtgctgg acatgaaggc tatggactcc aagtctaacg cgccatcgc ctggtctaat      1620 cagaccagct tcacatgcca ggacatcttt aaggagacaa atgccacata cccttctagc     1680
gacgtgccat gtgatgccac cctgacagag aagagcttcg agacagatat gaacctgaat     1740
tttcagaacc tgctggtcat cgtgctgagg atcctgctgc tgaaggtggc cggcttcaat     1800
ctgctgatga cactgcgcct gtggtcctct tga                                  1833
```

```
<210> SEQ ID NO 98
<211> LENGTH: 1794
<212> TYPE: DNA
<213> ORGANISM: Artificial Sequence
<220> FEATURE:
<223> OTHER INFORMATION: Synthetic

<400> SEQUENCE: 98
atggcatgcc ggctgctgtg ctgtgccgtg ctgtgcctgc tgggagcacc tatggagaca       60
ggagtgaccc agacacctag acacctggtc atgggcatga caaacaagaa gtctctgaag      120
tgcgagcagc acctgggcca caatgccatg tactggtata gcagagcgc caagaagcct       180 ctggagctga tgttcgtgta caactttaag gagcagaccg agaacaatag cgtgccatcc      240
aggttctctc agagtgccc caatagctcc cacctgtttc tgcacctgca cactgcag        300 cctgaggatt ccgccctgta cctgtgcgcc tctagccagg catgggagag agcagacgga      360
gagctgttct ttggagaggg cagccggctg accgtgctgg aggatctgag aaacgtgaca      420
ccccctaagg tgagcctgtt cgagccatcc aaggccgaga tcgccaataa gcagaaggcc      480
accctggtgt gcctggccag aggcttcttt cccgaccacg tggagctgtc ctggtgggtg      540
aacggcaagg aggtgcactc tggcgtgtgc accgatcctc aggcctacaa ggagagcaat      600
tactcctatt gtctgtcctc tcggctgaga gtgtccgcca cattttggca caacccccgg      660
```

-continued

```
aatcacttca gatgccaggt gcagtttcac ggcctgtccg aggaggacaa gtggcctgag      720
ggctctccaa agcccgtgac ccagaacatc agcgccgagg catggggaag ggcagattgt      780
ggaatcacct ctgccagcta tcagcagggc gtgctgagcg ccacaatcct gtacgagatc      840
ctgctgggca aggccaccct gtatgccgtg ctggtgtcta cactggtggt catggctatg      900
gtgaagagaa agaacagcag ggccaagcgg agcggatctg gagccaccaa tttctccctg      960
ctgaagcagg caggcgacgt ggaggagaac cctggaccaa tgtggggcgt gtttctgctg     1020
tacgtgtcca tgaagatggg caccacaggc cagaatatcg atcagccaac cgagatgacc     1080
gccacagagg gcgccatcgt gcagatcaac tgcacctacc agacatccgg cttcaatggc     1140
ctgttttggt atcagcagca cgcaggagag gcacccacat tcctgtctta taacgtgctg     1200
gacggcctgg aggagaaggg caggttcagc tcctttctga gccgctccaa gggctacagc     1260
tatctgctgc tgaaggagct gcagatgaag gattctgcca gctacctgtg cgccgtgttc     1320
tctagcggct ctgccaggca gctgaccttt ggcagcggca cccagctgac agtgctgcca     1380
aacatccaga atcccgagcc tgccgtgtat cagctgaagg accccgctc tcaggatagc      1440 accctgtgcc tgttcacaga ctttgatagc cagatcaacg tgcccaagac aatggagtcc     1500
ggcaccttca tcacagacaa gtgcgtgctg gacatgaagg ctatggactc caagtctaac     1560
ggcgccatcg cctggtccaa tcagacctct ttcacatgcc aggacatctt taaggagaca     1620
aatgccacat accttcctc tgacgtgcca tgtgatgcca ccctgacaga gaagagcttc      1680
gagacagata tgaacctgaa ttttcagaac ctgctggtca tcgtgctgag gatcctgctg     1740
ctgaaggtgg ccggctttaa tctgctgatg acactgcgcc tgtggagctc ctga          1794
```

```
<210> SEQ ID NO 99
<211> LENGTH: 4
<212> TYPE: PRT
<213> ORGANISM: Artificial Sequence
<220> FEATURE:
<223> OTHER INFORMATION: Synthetic

<400> SEQUENCE: 99

Ser Gly Ser Gly
1
```